United States Patent
Carmena et al.

(10) Patent No.: US 12,226,636 B2
(45) Date of Patent: Feb. 18, 2025

(54) IMPLANTS USING ULTRASONIC COMMUNICATION FOR MODULATING SPLENIC NERVE ACTIVITY

(71) Applicant: Iota Biosciences, Inc., Alameda, CA (US)

(72) Inventors: Jose M. Carmena, Alameda, CA (US); Michel M. Maharbiz, El Cerrito, CA (US); Ryan Neely, Mill Valley, CA (US); Joshua Kay, Oakland, CA (US)

(73) Assignee: IOTA BIOSCIENCES, INC., Alameda, CA (US)

( * ) Notice: Subject to any disclaimer, the term of this patent is extended or adjusted under 35 U.S.C. 154(b) by 0 days.

(21) Appl. No.: 18/475,136

(22) Filed: Sep. 26, 2023

(65) Prior Publication Data
US 2024/0017071 A1    Jan. 18, 2024

Related U.S. Application Data

(62) Division of application No. 16/389,816, filed on Apr. 19, 2019, now Pat. No. 11,890,474.
(Continued)

(51) Int. Cl.
*A61B 5/388* (2021.01)
*A61N 1/36* (2006.01)
(Continued)

(52) U.S. Cl.
CPC .......... *A61N 1/36117* (2013.01); *A61B 5/388* (2021.01); *A61N 1/3606* (2013.01);
(Continued)

(58) Field of Classification Search
CPC .............. A61N 1/36117; A61N 1/3606; A61N 1/36157; A61N 1/36171; A61N 1/36178;
(Continued)

(56) References Cited

U.S. PATENT DOCUMENTS

| 4,183,104 A | 1/1980 | Frey |
| 4,227,265 A | 10/1980 | Frey |

(Continued)

FOREIGN PATENT DOCUMENTS

| CN | 101048194 A | 10/2007 |
| CN | 101939048 A | 1/2011 |

(Continued)

OTHER PUBLICATIONS

U.S. Appl. No. 18/414, 173, Carmena et al., filed Jan. 16, 2024. (Copy not submitted herewith pursuant to the waiver of 37 C.F.R. § 1.98(a)(2)(iii) issued by the Office on Sep. 21, 2004).

(Continued)

*Primary Examiner* — Ankit D Tejani
*Assistant Examiner* — Joshua Brendon Solomon
(74) *Attorney, Agent, or Firm* — MORRISON & FOERSTER LLP

(57) ABSTRACT

Described herein are methods for monitoring or modulating an immune system in a subject; treating, reducing or monitoring inflammation; monitoring blood pressure; treating hypertension; or administering or adjusting a therapy for inflammation or hypertension in a patient by electrically stimulating the splenic nerve or detecting splenic nerve activity using an implanted medical device. Also described herein are implantable medical devices for performing such methods. The implanted medical device includes an ultrasonic transducer configured to receive ultrasonic waves and convert energy from the ultrasonic waves into an electrical energy that powers the device, two or more electrodes in electrical communication with the ultrasonic transducer that are configured to electrically stimulate a splenic nerve or detect a splenic nerve activity, and optionally a splenic nerve attachment member.

23 Claims, 12 Drawing Sheets

Related U.S. Application Data

(60) Provisional application No. 62/660,109, filed on Apr. 19, 2018.

(51) Int. Cl.
*A61N 1/372* (2006.01)
*A61N 1/378* (2006.01)

(52) U.S. Cl.
CPC ..... *A61N 1/36157* (2013.01); *A61N 1/36171* (2013.01); *A61N 1/36178* (2013.01); *A61N 1/37223* (2013.01); *A61N 1/3787* (2013.01)

(58) Field of Classification Search
CPC .............. A61N 1/37223; A61N 1/3787; A61N 1/0556; A61N 1/37217; A61N 1/37518; A61N 1/05; A61N 1/36053; A61N 1/36121; A61B 5/24; A61B 5/6877; A61B 5/6884; A61B 5/416; A61B 5/4836; A61B 5/686; H02J 2310/23; H02J 50/15
See application file for complete search history.

(56) References Cited

U.S. PATENT DOCUMENTS

| | | |
|---|---|---|
| 4,681,585 A | 7/1987 | Sayano |
| 5,095,905 A | 3/1992 | Klepinski |
| 5,193,539 A | 3/1993 | Schulman |
| 5,282,468 A | 2/1994 | Klepinski |
| 6,170,488 B1 | 1/2001 | Spillman, Jr. |
| 6,200,265 B1 | 3/2001 | Walsh |
| 6,802,811 B1 | 10/2004 | Slepian |
| 6,885,888 B2 | 4/2005 | Rezai |
| 7,024,248 B2 | 4/2006 | Penner |
| 7,283,874 B2 | 10/2007 | Penner |
| 7,418,292 B2 | 8/2008 | Shafer |
| 7,616,990 B2 | 11/2009 | Chavan |
| 7,617,001 B2 | 11/2009 | Penner |
| 7,634,318 B2 | 12/2009 | Tran |
| 7,756,587 B2 | 7/2010 | Penner |
| 7,757,565 B2 | 7/2010 | Chakrabartty |
| 7,769,442 B2 | 8/2010 | Shafer |
| 7,778,704 B2 | 8/2010 | Rezai |
| 7,794,499 B2 | 9/2010 | Navarro |
| 7,894,907 B2 | 2/2011 | Cowan |
| 7,899,542 B2 | 3/2011 | Cowan |
| 8,285,389 B2 | 10/2012 | Libbus et al. |
| 8,340,778 B2 | 12/2012 | Tran |
| 8,412,338 B2 | 4/2013 | Faltys |
| 8,478,428 B2 | 7/2013 | Cowley |
| 8,494,642 B2 | 7/2013 | Cowan |
| 8,494,643 B2 | 7/2013 | Cowan |
| 8,515,520 B2 | 8/2013 | Brunnett et al. |
| 8,515,544 B2 | 8/2013 | Daly |
| 8,577,460 B2 | 11/2013 | Penner |
| 8,612,002 B2 | 12/2013 | Faltys |
| 8,660,648 B2 | 2/2014 | Chavan |
| 8,774,928 B2 | 7/2014 | Towe |
| 8,788,034 B2 | 7/2014 | Levine |
| 8,805,537 B1 | 8/2014 | Cong et al. |
| 8,849,412 B2 | 9/2014 | Perryman |
| 8,855,767 B2 | 10/2014 | Faltys |
| 8,874,233 B2 | 10/2014 | Mclaughlin |
| 8,886,339 B2 | 11/2014 | Faltys |
| 8,903,501 B2 | 12/2014 | Perryman |
| 8,934,972 B2 | 1/2015 | Penner |
| 8,938,300 B2 | 1/2015 | Rosero |
| 8,996,116 B2 | 3/2015 | Faltys |
| 9,162,064 B2 | 10/2015 | Faltys |
| 9,174,041 B2 | 11/2015 | Faltys |
| 9,174,044 B2 | 11/2015 | Mclaughlin |
| 9,199,089 B2 | 12/2015 | Perryman |
| 9,211,409 B2 | 12/2015 | Tracey |
| 9,211,410 B2 | 12/2015 | Levine |
| 9,220,897 B2 | 12/2015 | Perryman |
| 9,242,103 B2 | 1/2016 | Perryman |
| 9,409,030 B2 | 8/2016 | Perryman |
| 9,544,068 B2 | 1/2017 | Arbablan |
| 9,566,449 B2 | 2/2017 | Perryman |
| 9,597,508 B2 | 3/2017 | Mclaughlin |
| 9,610,442 B2 | 4/2017 | Yoo et al. |
| 9,623,253 B2 | 4/2017 | Perryman |
| 9,662,490 B2 | 5/2017 | Tracey |
| 9,700,716 B2 | 7/2017 | Faltys |
| 9,717,921 B2 | 8/2017 | Perryman |
| 9,731,141 B2 | 8/2017 | Tran |
| 9,757,571 B2 | 9/2017 | Perryman |
| 9,789,314 B2 | 10/2017 | Perryman |
| 9,802,055 B2 | 10/2017 | Reinke |
| 9,833,621 B2 | 12/2017 | Levine |
| 9,849,286 B2 | 12/2017 | Levine |
| 9,925,384 B2 | 3/2018 | Perryman |
| 9,974,593 B2 | 5/2018 | Barman |
| 9,974,965 B2 | 5/2018 | Perryman |
| 9,993,651 B2 | 6/2018 | Faltys |
| 10,014,570 B2 | 7/2018 | Arbabian |
| 10,118,054 B2 | 11/2018 | Maharbiz |
| 10,177,606 B2 | 1/2019 | Charthad |
| 10,201,706 B2 | 2/2019 | Schwab |
| 10,220,203 B2 | 3/2019 | Faltys |
| 10,286,206 B2 | 5/2019 | Johnson et al. |
| 10,300,309 B2 | 5/2019 | Maharbiz |
| 10,300,310 B2 | 5/2019 | Maharbiz |
| 10,576,305 B2 | 3/2020 | Maharbiz |
| 10,682,530 B2 | 6/2020 | Maharbiz |
| 10,744,347 B2 | 8/2020 | Maharbiz |
| 10,765,865 B2 | 9/2020 | Maharbiz |
| 10,898,736 B2 | 1/2021 | Maharbiz et al. |
| 11,033,746 B2 | 6/2021 | Maharbiz et al. |
| 11,717,689 B2 | 8/2023 | Maharbiz et al. |
| 11,786,124 B2 | 10/2023 | Maharbiz et al. |
| 11,890,474 B2 | 2/2024 | Carmena |
| 11,969,596 B2 | 4/2024 | Carmena |
| 12,004,840 B2 | 6/2024 | Maharbiz |
| 2003/0236557 A1 | 12/2003 | Whitehurst et al. |
| 2005/0010265 A1 | 1/2005 | Baru et al. |
| 2005/0075701 A1 | 4/2005 | Shafer |
| 2005/0075702 A1 | 4/2005 | Shafer |
| 2006/0136004 A1 | 6/2006 | Cowan |
| 2006/0178703 A1 | 8/2006 | Huston |
| 2006/0287678 A1 | 12/2006 | Shafer |
| 2007/0027486 A1 | 2/2007 | Armstrong |
| 2007/0093875 A1 | 4/2007 | Chavan |
| 2007/0255333 A1 | 11/2007 | Giftakis et al. |
| 2007/0293895 A1 | 12/2007 | Cowan |
| 2008/0108915 A1 | 5/2008 | Penner |
| 2009/0018403 A1 | 1/2009 | Black |
| 2009/0210042 A1 | 8/2009 | Kowalczewski |
| 2009/0248097 A1 | 10/2009 | Tracey |
| 2009/0275997 A1 | 11/2009 | Faltys |
| 2009/0326602 A1 | 12/2009 | Glukhovsky |
| 2010/0145221 A1 | 6/2010 | Brunnett et al. |
| 2010/0268078 A1 | 10/2010 | Scarantino |
| 2010/0331933 A1 | 12/2010 | Carbunaru et al. |
| 2010/0331993 A1 | 12/2010 | Gradl |
| 2011/0054569 A1 | 3/2011 | Zitnik |
| 2011/0184486 A1 | 7/2011 | De Ridder |
| 2012/0185007 A1 | 7/2012 | Ziegler et al. |
| 2013/0062527 A1 | 3/2013 | Hyde |
| 2013/0073000 A1 | 3/2013 | Chavan et al. |
| 2013/0165998 A1 | 6/2013 | Libbus et al. |
| 2013/0238044 A1 | 9/2013 | Penner |
| 2013/0282070 A1 | 10/2013 | Cowan |
| 2013/0310909 A1 | 11/2013 | Simon |
| 2013/0324891 A1 | 12/2013 | Towe |
| 2014/0094887 A1 | 4/2014 | True et al. |
| 2014/0228905 A1 | 8/2014 | Bolea |
| 2014/0253435 A1 | 9/2014 | Boser |
| 2014/0336474 A1 | 11/2014 | Arbabian |
| 2014/0336727 A1 | 11/2014 | Perryman |
| 2015/0032178 A1 | 1/2015 | Simon et al. |
| 2015/0073510 A1 | 3/2015 | Perryman |
| 2015/0105686 A1 | 4/2015 | Vasan |
| 2015/0112233 A1 | 4/2015 | Towe |

(56) References Cited

U.S. PATENT DOCUMENTS

| | | |
|---|---|---|
| 2015/0241447 A1 | 8/2015 | Zitnik |
| 2015/0273210 A1 | 10/2015 | Johnson |
| 2015/0297900 A1 | 10/2015 | Perryman |
| 2016/0007836 A1 | 1/2016 | Kikuchi |
| 2016/0007893 A1 | 1/2016 | Roberts |
| 2016/0015988 A1 | 1/2016 | Perryman et al. |
| 2016/0023003 A1 | 1/2016 | Perryman |
| 2016/0023005 A1 | 1/2016 | Perryman |
| 2016/0038741 A1 | 2/2016 | Perryman |
| 2016/0038769 A1 | 2/2016 | Sullivan |
| 2016/0045743 A1 | 2/2016 | Liu |
| 2016/0067497 A1 | 3/2016 | Levine |
| 2016/0096016 A1 | 4/2016 | Tracey et al. |
| 2016/0114165 A1 | 4/2016 | Levine |
| 2016/0235329 A1 | 8/2016 | Bernstein |
| 2016/0331952 A1 | 11/2016 | Faltys |
| 2016/0331962 A1 | 11/2016 | Schwab |
| 2016/0339238 A1 | 11/2016 | Ahmed |
| 2016/0361535 A1 | 12/2016 | Perryman et al. |
| 2016/0367823 A1 | 12/2016 | Cowan et al. |
| 2017/0001003 A1 | 1/2017 | Pivonka |
| 2017/0007836 A1 | 1/2017 | Nassif |
| 2017/0007853 A1 | 1/2017 | Alford |
| 2017/0043156 A1 | 2/2017 | Possover |
| 2017/0095198 A1 | 4/2017 | Towe |
| 2017/0095667 A1 | 4/2017 | Yakovlev |
| 2017/0100588 A1 | 4/2017 | Schwab |
| 2017/0100589 A1 | 4/2017 | Schwab |
| 2017/0100604 A1 | 4/2017 | Schwab |
| 2017/0100605 A1 | 4/2017 | Schwab |
| 2017/0117753 A1 | 4/2017 | Charthad |
| 2017/0125892 A1 | 5/2017 | Arbabian |
| 2017/0136244 A1 | 5/2017 | Bonde |
| 2017/0173328 A1 | 6/2017 | Ostroff |
| 2017/0197082 A1 | 7/2017 | Pang |
| 2017/0202467 A1 | 7/2017 | Zitnik et al. |
| 2017/0203098 A1 | 7/2017 | Jiang |
| 2017/0266454 A1 | 9/2017 | Amir et al. |
| 2017/0281954 A1 | 10/2017 | Reinke et al. |
| 2017/0304630 A1 | 10/2017 | Plachta |
| 2017/0319858 A1 | 11/2017 | Radziemski et al. |
| 2017/0367591 A1 | 12/2017 | Jorgenson |
| 2018/0008828 A1 | 1/2018 | Perryman |
| 2018/0021214 A1 | 1/2018 | Tracey |
| 2018/0021580 A1 | 1/2018 | Tracey |
| 2018/0027077 A1 | 1/2018 | Melodia |
| 2018/0043157 A1 | 2/2018 | Sharma |
| 2018/0055393 A1 | 3/2018 | Cantwell |
| 2018/0085593 A1 | 3/2018 | Fayram et al. |
| 2018/0085605 A1 | 3/2018 | Maharbiz |
| 2018/0093099 A1 | 4/2018 | Cogan |
| 2018/0117319 A1 | 5/2018 | Chew |
| 2018/0117320 A1 | 5/2018 | Levine |
| 2018/0133474 A1 | 5/2018 | Meadows et al. |
| 2018/0154142 A1 | 6/2018 | Guo et al. |
| 2018/0154156 A1 | 6/2018 | Clark et al. |
| 2018/0161002 A1 | 6/2018 | Alford et al. |
| 2018/0169423 A1 | 6/2018 | Perryman |
| 2018/0236248 A1 | 8/2018 | Perryman |
| 2018/0264277 A1 | 9/2018 | Perryman |
| 2018/0289970 A1 | 10/2018 | Faltys |
| 2018/0289971 A1 | 10/2018 | Yeh et al. |
| 2019/0015675 A1* | 1/2019 | Giarola ............. A61N 1/3605 |
| 2019/0022384 A1 | 1/2019 | Kai et al. |
| 2019/0022427 A1 | 1/2019 | Maharbiz |
| 2019/0022428 A1 | 1/2019 | Maharbiz |
| 2019/0150881 A1 | 5/2019 | Maharbiz |
| 2019/0150882 A1 | 5/2019 | Maharbiz |
| 2019/0150883 A1 | 5/2019 | Maharbiz |
| 2019/0150884 A1 | 5/2019 | Maharbiz |
| 2019/0290913 A1 | 9/2019 | Blancou et al. |
| 2019/0321640 A1 | 10/2019 | Carmena |
| 2019/0321644 A1 | 10/2019 | Maharbiz |
| 2020/0023208 A1 | 1/2020 | Maharbiz |
| 2020/0023209 A1 | 1/2020 | Maharbiz |
| 2020/0114175 A1 | 4/2020 | Maharbiz |
| 2020/0230441 A1 | 7/2020 | Maharbiz |
| 2020/0257136 A1 | 8/2020 | Arbabian et al. |
| 2020/0289857 A1 | 9/2020 | Maharbiz |
| 2020/0324148 A1 | 10/2020 | Maharbiz |
| 2020/0391035 A1 | 12/2020 | Donega et al. |
| 2021/0268294 A1 | 9/2021 | Maharbiz et al. |
| 2021/0308462 A1 | 10/2021 | Carmena et al. |
| 2022/0047869 A1 | 2/2022 | Carmena et al. |
| 2022/0062650 A1 | 3/2022 | Maharbiz et al. |
| 2022/0143414 A1 | 5/2022 | Maharbiz et al. |
| 2022/0296886 A1 | 9/2022 | Bashirullah et al. |
| 2023/0089015 A1 | 3/2023 | Maharbiz et al. |
| 2023/0095948 A1 | 3/2023 | Maharbiz et al. |
| 2023/0233851 A1 | 7/2023 | Neely et al. |
| 2023/0301514 A1 | 9/2023 | Lepe et al. |
| 2024/0024032 A1 | 1/2024 | Kay |
| 2024/0099584 A1 | 3/2024 | Maharbiz |
| 2024/0100327 A1 | 3/2024 | Carmena |
| 2024/0108882 A1 | 4/2024 | Maharbiz |
| 2024/0148250 A1 | 5/2024 | Maharbiz |
| 2024/0226567 A1 | 7/2024 | Carmena |

FOREIGN PATENT DOCUMENTS

| | | |
|---|---|---|
| CN | 102821814 A | 12/2012 |
| CN | 104254291 A | 12/2014 |
| CN | 104623808 A | 5/2015 |
| CN | 104736197 A | 6/2015 |
| CN | 105228513 A | 1/2016 |
| CN | 105848710 A | 8/2016 |
| CN | 107073257 A | 8/2017 |
| CN | 107106840 A | 8/2017 |
| CN | 107614057 A | 1/2018 |
| CN | 107789730 A | 3/2018 |
| CN | 107864633 A | 3/2018 |
| EP | 1745818 A1 | 1/2007 |
| EP | 2515996 A2 | 10/2012 |
| EP | 2355893 B1 | 12/2013 |
| EP | 2667942 A2 | 12/2013 |
| EP | 2694154 A1 | 2/2014 |
| EP | 2741810 A1 | 6/2014 |
| EP | 2162185 B1 | 7/2015 |
| EP | 1648559 B1 | 9/2015 |
| EP | 2928557 A2 | 10/2015 |
| EP | 2959937 A1 | 12/2015 |
| EP | 2707094 B1 | 2/2016 |
| EP | 2337609 B1 | 8/2016 |
| EP | 2755718 B1 | 12/2017 |
| EP | 3259015 A1 | 12/2017 |
| EP | 3259017 A1 | 12/2017 |
| EP | 2736592 B1 | 1/2018 |
| EP | 3285856 A1 | 2/2018 |
| EP | 2651431 B1 | 3/2018 |
| EP | 3294376 A1 | 3/2018 |
| EP | 3338855 A1 | 6/2018 |
| EP | 2440284 B1 | 9/2018 |
| EP | 3403690 A1 | 11/2018 |
| EP | 3057652 B1 | 7/2023 |
| JP | H04503312 A | 6/1992 |
| JP | 2001170190 A | 6/2001 |
| JP | 2007021225 A | 2/2007 |
| JP | 2008546444 A | 12/2008 |
| JP | 2009512505 A | 3/2009 |
| JP | 2010508969 A | 3/2010 |
| JP | 2011513038 A | 4/2011 |
| JP | 2014525288 A | 9/2014 |
| JP | 2015528385 A | 9/2015 |
| JP | 2018501024 A | 1/2018 |
| JP | 2019503722 A | 2/2019 |
| NO | 2021168163 A1 | 8/2021 |
| RU | 2675350 C1 | 12/2018 |
| WO | 2005032653 A1 | 4/2005 |
| WO | 2006029257 A2 | 3/2006 |
| WO | 2006138068 A2 | 12/2006 |
| WO | 2007050657 A1 | 5/2007 |
| WO | 2007090159 A1 | 8/2007 |
| WO | 2009114689 A1 | 9/2009 |
| WO | 2009146030 A1 | 12/2009 |

(56) References Cited

FOREIGN PATENT DOCUMENTS

| | | |
|---|---|---|
| WO | 2010059617 A2 | 5/2010 |
| WO | 2010059617 A3 | 9/2010 |
| WO | 2010144578 A2 | 12/2010 |
| WO | 2010144578 A3 | 3/2011 |
| WO | 2011028763 A2 | 3/2011 |
| WO | 2011079309 A2 | 6/2011 |
| WO | 2011028763 A3 | 7/2011 |
| WO | 2011079309 A3 | 11/2011 |
| WO | 2012057868 A1 | 5/2012 |
| WO | 2012083259 A2 | 6/2012 |
| WO | 2012103519 A2 | 8/2012 |
| WO | 2012138782 A1 | 10/2012 |
| WO | 2012154865 A2 | 11/2012 |
| WO | 2012154865 A3 | 1/2013 |
| WO | 2013019757 A2 | 2/2013 |
| WO | 2013025632 A1 | 2/2013 |
| WO | 2013028428 A1 | 2/2013 |
| WO | 2013040549 A1 | 3/2013 |
| WO | 2013044207 A1 | 3/2013 |
| WO | 2012083259 A3 | 9/2013 |
| WO | 2013134479 A1 | 9/2013 |
| WO | 2012103519 A3 | 3/2014 |
| WO | 2014055408 A1 | 4/2014 |
| WO | 2013019757 A3 | 5/2014 |
| WO | 2014089299 A2 | 6/2014 |
| WO | 2014153218 A1 | 9/2014 |
| WO | 2014153219 A1 | 9/2014 |
| WO | 2014153223 A1 | 9/2014 |
| WO | 2014153228 A1 | 9/2014 |
| WO | 2014089299 A3 | 10/2014 |
| WO | 2014169145 A1 | 10/2014 |
| WO | 2015127476 A1 | 8/2015 |
| WO | 2015142842 A2 | 9/2015 |
| WO | 2015142842 A3 | 11/2015 |
| WO | 2016028608 A1 | 2/2016 |
| WO | 2016112398 A1 | 7/2016 |
| WO | 2016134197 A1 | 8/2016 |
| WO | 2016134199 A1 | 8/2016 |
| WO | 2016168798 A1 | 10/2016 |
| WO | 2016170510 A1 | 10/2016 |
| WO | 2016183353 A1 | 11/2016 |
| WO | 2016187114 A1 | 11/2016 |
| WO | 2017087681 A1 | 5/2017 |
| WO | 2017143185 A1 | 8/2017 |
| WO | 2017143191 A1 | 8/2017 |
| WO | WO-2017149438 A1 * | 9/2017 ............... A61F 7/00 |
| WO | 2018005848 A1 | 1/2018 |
| WO | 2018009905 A2 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018017591 A1 | 1/2018 |
| WO | 2018009905 A3 | 2/2018 |
| WO | 2018067630 A1 | 4/2018 |
| WO | 2018081763 A1 | 5/2018 |
| WO | 2018081826 A1 | 5/2018 |
| WO | 2018087193 A1 | 5/2018 |
| WO | 2018089895 A2 | 5/2018 |
| WO | 2018089895 A3 | 6/2018 |
| WO | 2018118857 A1 | 6/2018 |
| WO | 2018118860 A1 | 6/2018 |
| WO | 2018118861 A1 | 6/2018 |
| WO | 2018118864 A1 | 6/2018 |
| WO | 2018118866 A1 | 6/2018 |
| WO | 2019075203 A1 | 4/2019 |
| WO | 2019122903 A2 | 6/2019 |
| WO | 2019122908 A1 | 6/2019 |
| WO | 2019126616 A1 | 6/2019 |
| WO | 2019122903 A3 | 8/2019 |
| WO | 2019204773 A1 | 10/2019 |
| WO | 2020047152 A1 | 3/2020 |
| WO | 2020117967 A1 | 6/2020 |
| WO | 2020142732 A1 | 7/2020 |
| WO | 2020142733 A1 | 7/2020 |
| WO | 2020254798 A1 | 12/2020 |
| WO | 2021077020 A1 | 4/2021 |
| WO | 2021077022 A1 | 4/2021 |
| WO | 2021105699 A1 | 6/2021 |
| WO | 2021105708 A1 | 6/2021 |
| WO | 2021108810 A1 | 6/2021 |
| WO | 2021168229 A1 | 8/2021 |
| WO | 2021248013 A1 | 12/2021 |
| WO | 2022035889 A1 | 2/2022 |
| WO | 2022046770 A1 | 3/2022 |
| WO | 2023183891 A2 | 9/2023 |
| WO | 2024011141 A2 | 1/2024 |
| WO | 2024086662 A1 | 4/2024 |
| WO | 2024167868 A2 | 8/2024 |
| WO | 2024182632 A2 | 9/2024 |

OTHER PUBLICATIONS

Arbabian, A. et al. (Dec. 1, 2016, e-pub. Nov. 11, 2016). "Sound Technologies, Sound Bodies: Medical Implants With Ultrasonic Links," IEEE Microwave Magazine 17(12):39-54.

Bertrand, A. et al. (Aug. 2014). "Beamforming Approaches for Untethered, Ultrasonic Neural Dust Motes for Cortical Recording: A Simulation Study," IEEE EMBC, 2625-2628.

Beyer, G.P. et al. (Jan. 1, 2008). "An Implantable MOSFET Dosimeter for the Measurement of Radiation Dose in Tissue During Cancer Therapy," IEEE Sensors Journal 8(1):38-51.

Brown, G.L. et al. (1957). "The Output of Sympathetic Transmitter From the Spleen of the Cat," J. Physiol. 138:81-102.

Carnevale, D. et al. (Sep. 27, 2016). "A Cholinergic-Sympathetic Pathway Primes Immunity In Hypertension and Mediates Brain-To-Spleen Communication," Nature Communications, 7:13035, 13 pages.

Celinskis, D. et al. (Aug. 26, 2014). "Wireless Impedance Measurements for Monitoring Peripheral Vascular Disease," 36th Annual International Conference of the IEEE Engineering in Medicine and Biology Society pp. 6937-6940.

Coldewey, D. (Dec. 27, 2018). "Iota Biosciences Raises $15M to Produce In-Body Sensors Smaller Than a Grain of Rice," TechCrunch, 4 pages.

Eckberg, D.L. et al. (1988). "Baroreflex Modulation of Sympathetic Activity and Sympathetic Neurotransmitters in Humans," Acta Physiol. Scand. 133:221-231.

Grossman, N. et al. (Jun. 1, 2017). "Noninvasive Deep Brain Stimulation via Temporally Interfering Electric Fields," Cell 169:1029-1041.

Guyot, M. et al. (2019, e-pub. Mar. 15, 2019). "Apical Splenic Nerve Electrical Stimulation Discloses an Anti-Inflammatory Pathway Relying on Adrenergic and Nicotinic Receptors in Myeloid Cells," Brain, Behavior, and Immunity 80:238-246.

Hellyer, J. et al. (Feb. 2014). "Autonomic Nerve Activity and Blood Pressure in Ambulatory Dogs," Heart Rhythm, 11(2):307-313, 14 pages.

International Preliminary Report on Patentability, issued Apr. 19, 2022, for PCT Application No. PCT/US2020/056159, filed Oct. 16, 2020, 10 pages.

International Preliminary Report on Patentability, issued Apr. 19, 2022, for PCT Application No. PCT/US2020/056161, filed Oct. 16, 2020, 8 pages.

International Preliminary Report on Patentability, issued Mar. 2, 2021 for PCT Application No. PCT/US2019/048647, filed Aug. 28, 2019, 7 pages.

International Preliminary Report on Patentability, issued Oct. 20, 2020 for PCT Application No. PCT/ US2019/028385, filed Apr. 19, 2019, 7 pages.

International Preliminary Report on Patentability, issued Oct. 29, 2020, for PCT Application No. PCT/ US2019/028381, filed Apr. 19, 2019, 11 pages.

International Search Report and Written Opinion, mailed Aug. 22, 2019 for PCT Application No. PCT/ US2019/028381, filed Apr. 19, 2019, 23 pages.

(56) References Cited

OTHER PUBLICATIONS

International Search Report and Written Opinion, mailed Aug. 29, 2019 for PCT Application No. PCT/ US2019/028385, filed Apr. 19, 2019, 10 pages.
International Search Report and Written Opinion, mailed Feb. 26, 2021, for PCT Application No. PCT/ US2020/056161, filed Oct. 16, 2020, 13 pages.
International Search Report and Written Opinion, mailed Jan. 21, 2021 for PCT Application No. PCT/ US2020/056159, filed Oct. 16, 2020, 13 pages.
International Search Report and Written Opinion, mailed Nov. 21, 2019, for PCT Application No. PCT/ US2019/048647, filed Aug. 28, 2019, 9 pages.
Katafuchi, T. et al. (1993). "Roles of Sympathetic Nervous System in the Suppression of Cytotoxicity of Splenic Natural Killer Cells in the Rat," J. of Physiology 465:343-357.
Kay, J. (May 4, 2017). "Rodent Wearable Ultrasound Interrogation System for Wireless Neural Recording", Berkeley EECS, Technical Report No. UCS/EECS-2017-27, 50 pages.
Kees, M.G. et al. (2003). "Via β-Adrenoceptors, Stimulation of Extrasplenic Sympathetic Nerve Fibers Inhibits Lipopolysaccharide-Induced TNF Secretion in Perfused Rat Spleen," J. of Neuroimmunology 145:77-85.
Kirpekar, S.M. et al. (1967). "Release of Noradrenaline by Splenic Nerve Stimulation and Its Dependence of Calcium," J. Physiol. 188:219-234.
Mazzilli, F. et al. (Aug. 31-Sep. 4, 2010). "In-Vitro Platform to Study Ultrasound as Source for Wireless Energy Transfer and Communication for Implanted Medical Devices," 32nd Annual International Conference of the IEEE EMBS, pp. 3751-3754.
Mazzilli, F. et al. (Oct. 2014). "A 10.5 cm Ultrasound Link for Deep Implanted Medical Devices," IEEE Transactions on Biomedical Circuits and Systems 8(5):738-750.
Niijima, A. et al. (1991). "The Effects of Interleukin-1β on the Activity of Adrenal, Splenic and Renal Sympathetic Nerves in the Rat," J. of the Autonomic Nervous System 36:183-192.
Ninomiya, I. et al. (Nov. 1971). "Sympathetic Nerve Activity to the Spleen, Kidney, and Heart in Response to Baroceptor Input," American J. of Physiology 221(5): 1346-1351.
Peisino, M. (May 17, 2013). "Deeply Implanted Medical Device Based on a Novel Ultrasonic Telemetry Technology," École Polytechnique Fédérale De Lausanne pp. 148.
Perrotta, M. et al. (2018, e-pub. Feb. 24, 2018). "The Interactions of the Immune System and the Brain in Hypertension," Current Hypertension Reports 20:7, 6 pages.
Piech, D.K. et al. (2017). "Rodent Wearable Ultrasound System for Wireless Neural Recording," 39th Annual International Conference of the IEEE Engineering in Medicine and Biology Society, EMBC, 5 pages.
Rayburn, E.R. et al. (2009). "Anti-Inflammatory Agents for Cancer Therapy," Mol. Cell. Pharmacol. 1(1):29-43, 20 pages.
Robertson, M.J. (Feb. 1, 2002). "Role of Chemokines in the Biology of Natural Killer Cells," J. Leukoc. Blol. 71:173-183.
Rosenberg, J. et al. (Mar. 2018, e-pub. Dec. 14. 2017). "CD+ T Cells and NK Cells: Parallel and Complementary Soldiers of Immunotherapy," Curr. Opin. Chem. Eng. 19:1-22.
Seo, D. (May 1, 2016). "Design of Ultrasonic Power Link for Neural Dust", Technical Report No. UCB/EECS-2016-21, Electrical Engineering and Computer Sciences University of California at Berkeley, 71 pages.
Seo, D. et al. (2015). "Ultrasonic Beamforming System for Interrogating Multiple Implantable Sensors," IEEE, pp. 2673-2676.
Seo, D. et al. (Apr. 1, 2015, e-pub. Aug. 7, 2014). "Model Validation of Untethered, Ultrasonic Neural Dust Motes for Cortical Recording," J. of Neuroscience Methods 244:114-122.
Seo, D. et al. (Aug. 3, 2016). "Wireless Recording in the Peripheral Nervous System with Ultrasonic Neural Dust," Neuron 91:529-539.
Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp. 1-11.
Simon, T et al. (Nov. 11, 2019). "Stimulation of Splenic Neurovascular Bundle Protect Mice from Developing Collagen-Induced Arthritis," Abstract No. 998, 2 pages.
Straub, R. H. et al. (Jul. 2000). "A Bacteria-Induced Switch of Sympathetic Effector Mechanisms Augments Local Inhibition of TNF-α and IL-6 Secretion in the Spleen," The FASEB Journal 14:1380-1388.
Straub, R.H. et al. (2002). "Immunoregulation of IL-6 Secretion by Endogenous and Exogenous Adenosine and by Exogenous Purinergic Agonists in Splenic Tissue Slices," J. of Neuroimmunology 125:73-81.
Tang, H.-Y. et al. (Dec. 2015). "Miniaturizing Ultrasonic System for Portable Health Care and Fitness," IEEE Transactions on Biomedical Circuits and Systems 9(6):767-776.
Taylor, J. et al. (2004). "Multiple-Electrode Nerve Cuffs for Low-Velocity and Velocity-Selective Neural Recording," Medical & Biological Engineering & Computing 42:634-643.
Tsai, J.-Y. et al. (2011). "Ultrasonic Wireless Power and Data Communication for Neural Stimulation," 2011 IEEEE International Ultrasonics Symposium pp. 1052-1055.
U.S. Appl. No. 17/767,409, Carmena et al., filed Oct. 16, 2020. (Copy not submitted herewith pursuant to the waiver of 37 C.F.R. § 1.98(a)(2)(ii) issued by the Office on Sep. 21, 2004).
U.S. Appl. No. 17/767,419, Maharbiz et al., filed Oct. 16, 2020. (Copy not submitted herewith pursuant to the waiver of 37 C.F.R. § 1.98(a)(2)(iii) issued by the Office on Sep. 21, 2004).
U.S. Appl. No. 18/244,174, Maharbiz et al., filed Sep. 8, 2023. (Copy not submitted herewith pursuant of the waiver of 37 C.F.R. 1.98(a)(2)(iii) issued by the Office on Sep. 21, 2004).
U.S. Appl. No. 18/343,707, Maharbiz et al., filed Jun. 28, 2023. (Copy not submitted herewith pursuant of the waiver of 37 C.F.R. 1.98(a)(2)(iii) issued by the Office on Sep. 21, 2004).
Weissleder, R. et al. (May 1, 2001). "Molecular Imaging," Radiology, Radiological Society of North America, Inc. 219(2):316-333.
Williams, J.M. et al. (1981). "Sympathetic Innervation of Murine Thymus and Spleen: Evidence for a Functional Link Between the Nervous and Immune Systems," Brain Research Bulletin 6:83-94.
Wodlinger, B. et al. (Oct. 2009). "Localization and Recovery of Peripheral Neural SourcesAlgorithms," IEEE Transactions on Neural Systems and Rehabilitation Engineering 17(5):461-468, 18 pages.
Kalakutsky, L.I. et al. (2012). "Systems Of Electrical Stimulation Of Organs And Tissues," Ministry of Education and Science of the Russian Federation, Samara State Aerospace University, Electronic Textbook, pp. 13-23, 24, 29-31, 32, 37. [English Translation], 108 pages total.
Kuznetsov, S.A. (2000). "About," Large Explanatory Dictionary Of The Russian Language, St. Petersburg, Russia, p. 708, 7 pages. [English Translation].
Martelli, D. et al. (Apr./May/Jun. 2014, e-pub. May 7, 2014). "Neural Control Of Inflammation By The Greater Splanchnic Nerves," Temperature 1(1):14-15, 3 pages.
Slavin, K.V. et al. (2016, e-pub. Dec. 1, 2016). "Tonic And Burst Spinal Cord Stimulation Waveforms For The Treatment Of Chronic, Intractable Pain: Study Protocol For A Randomized Controlled Trial," Trials 17(569):1-11.

* cited by examiner

IMPLANTS USING ULTRASONIC COMMUNICATION FOR MODULATING SPLENIC NERVE ACTIVITY

CROSS-REFERENCE TO RELATED APPLICATION

This application is a divisional of U.S. patent application Ser. No. 16/389,816, filed on Apr. 19, 2019; which claims priority benefit to U.S. Provisional Application No. 62/660,109, filed on Apr. 19, 2018; each of which is incorporated herein by reference for all purposes.

TECHNICAL FIELD

The present invention relates to methods of monitoring or modulating the immune system; treating, reducing, or monitoring inflammation; monitoring or modulating a blood pressure; treating hypertension; or administering or adjusting a therapy for inflammation or hypertension in a patient by electrically stimulating the splenic nerve or detecting splenic nerve activity using an implanted medical device. The present invention further relates to implantable medical devices for performing such methods.

BACKGROUND

Inflammatory diseases, such as rheumatoid arthritis, Crohn's disease, colitis, lupus, and spondylitis, affect millions of people worldwide, with annual medical costs exceeding billions of dollars each year. Further, for many inflammatory diseases, patients treated with pharmaceuticals eventually become desensitized to these drugs. Inflammatory symptoms can be controlled by modulating activity of the spleen, which is responsible for releasing immune cells and cytokines into the bloodstream that cause inflammation.

Implantable devices that emit electrical pulses to the vagus nerve have been developed, which can help modulate inflammation. The vagus nerve influences and communicates with the splenic nerve, which leads to the spleen, through a network of nerves that connects to many other organs, including the liver, stomach, heart, lungs, kidneys, and intestines. Therefore, electrical pulses transmitted to the vagus nerve modulate not only splenic activity, but also the activity of many other organs resulting in undesirable side effects. For example, vagus nerve stimulation can result in vocal cord pain, depressed heart rate, and long-term changes of the brain.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE INVENTION

Described herein are methods of monitoring or modulating the immune system; methods of treating, reducing, or monitoring inflammation; monitoring or modulating a blood pressure; treating hypertension; or administering or adjusting a therapy for inflammation or hypertension in a patient by electrically stimulating the splenic nerve or detecting splenic nerve activity using an implanted medical device. In some embodiments, splenic nerve activity and stimulation are performed in a closed-loop system, wherein the splenic nerve is stimulated in response to a detected splenic nerve activity or a detected change in splenic nerve activity. Further described herein are implantable medical devices for performing these methods.

In some embodiments, there is a method of modulating the immune system of a subject, comprising receiving ultrasonic waves from an external ultrasonic transducer; converting energy from the ultrasonic waves into electrical energy that powers a fully implanted medical device in the subject, the device comprising two or more electrodes that are in electrical communication with the splenic nerve of the subject; and electrically stimulating the splenic nerve using the device. The immune system may be modulated, for example, by modulating (increasing or reducing) a blood concentration of an inflammatory cytokine (such as tumor necrosis factor alpha (TNF-α), interleukin-6 (IL-6), interleukin-1β (IL-1β), or high mobility group box 1 (HMGB1)) and/or modulating (increasing or reducing immune cell activation (such as decreasing natural killer (NK) cell activation).

In some embodiments, there is a method of reducing inflammation in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce inflammation in the subject. In some embodiments, the inflammation is caused by an autoimmune disease. In some embodiments, the inflammation is caused by rheumatoid arthritis, Crohn's disease, colitis, lupus, or spondylitis.

In some embodiments, there is a method of treating an inflammatory disease in a subject, comprising receiving ultrasonic waves from an external ultrasonic transducer; converting energy from the ultrasonic waves into electrical energy that powers a fully implanted medical device in the subject having the inflammatory disease, the device comprising two or more electrodes that contact the splenic nerve of the subject; and electrically stimulating the splenic nerve using the device, wherein the stimulation is configured to reduce inflammation in the subject. In some embodiments, the inflammatory disease is an autoimmune disease. In some embodiments, the inflammatory disease is rheumatoid arthritis, Crohn's disease, colitis, lupus, or spondylitis.

In some embodiments, there is a method of modulating a blood concentration of an inflammatory cytokine in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce the blood concentration of the inflammatory cytokine in the subject. In some embodiments, the blood concentration of the inflammatory cytokine is increased in the subject. In some embodiments, the blood concentration of the inflammatory cytokine is reduced in the subject. In some embodiments, the method reduces splenic release of the inflammatory cytokine. In some embodiments, the inflammatory cytokine is tumor necrosis factor alpha (TNF-α), interleukin-6 (IL-6), interleukin-1 (IL-1) (such as interleukin-1β, IL-1β), or high mobility group box 1 (HMGB1).

In some embodiments of the above methods, electrically stimulating the splenic nerve occurs in response to a trigger signal. In some embodiments, the trigger signal is encoded in the ultrasonic waves received by the implanted medical device. In some embodiments, the trigger signal is based on splenic nerve activity. In some embodiments, the trigger signal is based on a deviation from a baseline splenic nerve activity. In some embodiments, the splenic nerve activity is detected by the implanted medical device. In some embodiments, the trigger signal is further based on a measured physiological condition. In some embodiments, the physiological condition is a temperature, a pulse rate, or a blood pressure. In some embodiments, the physiological condition is measured by the implanted medical device.

In some embodiments of the above methods, the method comprises emitting an ultrasonic backscatter encoding information related to the splenic nerve activity or the physiological condition. In some embodiments, the ultrasonic backscatter encoding the information related to the splenic nerve activity or the physiological condition is received by an external device. In some embodiments, the ultrasonic backscatter further encodes information related to the status of the device or one or more electrical pulses emitted by the device.

In some embodiments of the above methods, the method comprises transmitting, at the external device, ultrasonic waves that encode the trigger signal.

In some embodiments, there is a method of monitoring an immune system of a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; emitting an ultrasonic backscatter encoding information related to the electrical activity of the splenic nerve; and monitoring a deviation in the electric activity relative to a baseline electrical activity indicates a change in the status of the immune system of the subject. In some embodiments, an increase in the electrical activity of the splenic nerve indicates an increase in immune system activity.

In some embodiments of the above method of monitoring an immune system, the method comprises monitoring inflammation in the subject, wherein a change in the electrical activity of the splenic nerve indicates a change in inflammation in the subject. In some embodiments, an increase in the electrical activity of the splenic nerve indicates a change in inflammation in the subject. In some embodiments, a decrease in the electrical activity of the splenic nerve indicates a decrease in inflammation in the subject. In some embodiments, the inflammation is caused by an autoimmune disease. In some embodiments, the inflammation is caused by rheumatoid arthritis, Crohn's disease, colitis, lupus, or spondylitis.

In some embodiments of the above method of monitoring an immune system, the method comprises monitoring a therapy administered to the subject. In some embodiments, the method further comprises administering the therapy to the subject. In some embodiments, the therapy is an anti-inflammatory therapy. In some embodiments, the anti-inflammatory therapy is administered in response to a detected increase in inflammation. In some embodiments, the anti-inflammation therapy is a drug therapy. In some embodiments, the anti-inflammatory therapy comprises electrically stimulating a nerve. In some embodiments, the nerve is a vagus nerve, a celiac ganglion, a sub-diaphragmatic vagus nerve, a splanchnic nerve, a superior mesenteric nerve, or the splenic nerve of the subject.

In some embodiments of the above method of monitoring an immune system, the method comprises receiving the ultrasonic backscatter at an external device.

In some embodiments, there is a method of administering a therapy for inflammation in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; emitting an ultrasonic backscatter encoding the electric activity of the splenic nerve; monitoring a deviation in the electric activity of the splenic nerve compared to a baseline electrical activity of the splenic nerve; and administering an anti-inflammatory therapy if the deviation in the electrical activity of the splenic nerve indicates an inflammatory response. In some embodiments, the therapy comprises a drug therapy. In some embodiments, the therapy comprises electrically stimulating a nerve. In some embodiments, the nerve is a vagus nerve, a celiac ganglion, a sub-diaphragmatic vagus nerve, a splanchnic nerve, a superior mesenteric nerve, or the splenic nerve of the subject.

In some embodiments, there is a method of adjusting a therapy administered to a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; emitting an ultrasonic backscatter encoding the electric activity of the splenic nerve; receiving the ultrasonic backscatter at an external device; monitoring a deviation in the electrical activity of the splenic nerve compared to a baseline electrical activity of the splenic nerve, wherein the deviation indicates a change in immune system status of the subject; and adjusting the therapy based on the change in immune system status of the subject. In some embodiments, the change in immune system status is a change in an inflammatory response.

In some embodiments, the method of adjusting the therapy administered to the subject further comprises administering the therapy to the subject. In some embodiments, the therapy is an anti-inflammatory therapy. In some embodiments, the anti-inflammatory therapy is adjusted if the anti-inflammatory therapy does not result in a desired effect or results in an undesired inflammatory response. In some embodiments, the anti-inflammatory therapy is discontinued if the anti-inflammatory therapy obtains a desired effect. In some embodiments, the therapy comprises a drug therapy. In some embodiments, the therapy comprises adjusting a frequency or dose of the therapy administered to the subject. In some embodiments, the therapy comprises electrically stimulating a nerve. In some embodiments, the nerve is a vagus nerve, a celiac ganglion, a sub-diaphragmatic vagus nerve, a splanchnic nerve, a superior mesenteric nerve, or the splenic nerve of the subject. In some embodiments, adjusting the therapy comprises adjusting a frequency, voltage, current, or duration of one or more electrical pulses used to electrically stimulate the nerve. In some embodiments, the subject has an autoimmune disease that causes inflammation. In some embodiments, the subject has rheumatoid arthritis, Crohn's disease, colitis, lupus, or spondylitis.

In some embodiments, there is a method of modulating blood pressure in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to modulate blood pressure in the subject.

In some embodiments, there is a method of treating hypertension in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce hypertension in the subject. In some embodiments, electrically stimulating the splenic nerve comprises blocking splenic nerve activity. In some embodiments, electrically stimulating the splenic nerve comprises emitting a plurality of electrical pulses at a frequency of about 1 kHz or higher.

In some embodiments of the method of modulating blood pressure or treating hypertension, the method comprises electrically stimulating the splenic nerve occurs in response to a trigger signal. In some embodiments, the trigger signal is encoded in the ultrasonic waves received by the implanted medical device. In some embodiments, the trigger signal is based on splenic nerve activity. In some embodiments, the trigger signal is based on a deviation from a baseline splenic nerve activity. In some embodiments, the splenic nerve activity is detected by the implanted medical device. In some embodiments, the trigger signal is further based on a measured physiological condition. In some embodiments, the physiological condition is a temperature, a pulse rate, or a blood pressure. In some embodiments, the physiological condition is measured by the implanted medical device.

In some embodiment of the method of modulating blood pressure or treating hypertension, the method comprises emitting an ultrasonic backscatter encoding information related to the splenic nerve activity or the physiological condition. In some embodiments, the ultrasonic backscatter encoding the information related to the splenic nerve activity or the physiological condition is received by an external device. In some embodiments, the ultrasonic backscatter further encodes information related to the status of the device or one or more electrical pulses emitted by the device.

In some embodiment of the method of modulating blood pressure or treating hypertension, the method comprises transmitting, at the external device, ultrasonic waves that encode the trigger signal.

In some embodiments of any of the above methods, the method comprises transmitting the ultrasonic waves that power the implantable medical device using the external device.

In some embodiments of any of the above methods, the implanted medical device is fully implanted with in the perivascular fascia surrounding the splenic nerve and splenic artery.

In some embodiments of any of the above methods, the splenic nerve is not separated from the splenic artery.

In some embodiments of any of the above methods, the implantable medical device does not comprise a battery.

In some embodiments of any of the above methods, the implantable medical device does not comprise a radiofrequency communication system.

In some embodiments of any of the above methods, the implanted medical device does not comprise an electrical lead that extends from a body of the device.

In some embodiments of any of the above methods, the implanted medical device comprises a body comprising an ultrasonic transducer, and wherein the body of the device is attached to the splenic nerve or a splenic artery. In some embodiments, the implanted medical device comprises a splenic nerve attachment member attached to a body, wherein the splenic nerve attachment member is sized and configured to attach the device to the splenic nerve or a splenic artery and position two or more electrodes in electrical communication with the splenic nerve In some embodiments of any of the above methods, the implanted medical device has a length of about 5 mm or less in the longest dimension.

In some embodiments of any of the above methods, the implanted medical device has a volume of about 5 $mm^3$ or smaller.

In some embodiments of any of the above methods, the subject is anti-cyclic citrullinated peptide (anti-CCP) positive or fails to respond to a disease-modifying anti-rheumatic drug (DMARD).

In some embodiments of any of the above methods, the subject is a human.

Also described herein is an implantable medical device, comprising a body comprising an ultrasonic transducer configured to receive ultrasonic waves and convert energy from the ultrasonic waves into an electrical energy that powers the device; two or more electrodes in electrical communication with the ultrasonic transducer, wherein the electrodes are configured to electrically stimulate a splenic nerve or detect a splenic nerve activity; and a splenic nerve attachment member attached to the body, wherein the splenic nerve attachment member is sized and configured to attach the device to the splenic nerve or splenic artery and position the two or more electrodes in electrical communication with the splenic nerve.

In some embodiments of the implantable medical device, the splenic nerve attachment member comprises a clip that is configured to at least partially surround the splenic nerve or splenic artery. In some embodiments, the clip comprises a plurality of flexible legs that extend below the body. In some embodiments, the implantable device comprises a hook or loop configured to maneuver at least one of the flexible legs in response to maneuvering the hook or loop. In some embodiments, the hook or loop is positioned at a terminus of one of the flexible legs. In some embodiments, the hook or loop is positioned proximal to the body. In some embodiments, the flexible legs are curved. In some embodiments, the legs extend away from the body before curving toward the body as the legs extend below the body. In some embodiments, the plurality of flexible legs comprises at least one pair of legs, wherein the pair of legs comprises a first leg and a second leg that extend away from and below the body in opposite directions. In some embodiments, the first leg and the second leg are connected by a crossbar connected to the body. In some embodiments, the crossbar is connected to the body of the device through a flexible member. In some embodiments, the flexible member is a hinge. In some embodiments, the device comprises two pairs of legs, wherein each pair of leg is positioned on opposite sides of the body. In some embodiments, the legs are attached to the body through a bottom surface of the body. In some embodiments, the legs are attached to the body through a sidewall of the body. In some embodiments, the legs comprise a metal, metal alloy, ceramic, silicon, or a non-polymeric material.

In some embodiments of the above implantable medical device, the legs comprise an elastomeric coating or a non-elastomeric polymer coating. In some embodiments, the elastomeric coating or the non-elastomeric polymer coating is bioinert. In some embodiments, the elastomeric coating or the non-elastomeric polymer coating is a silicone, a poly(p-xylylene) polymer, a urethane polymer, or a polyimide. In some embodiments, at least one of the legs comprises an outer surface coated with the elastomeric coating or the non-elastomeric polymer coating and an inner surface comprising at least one electrode that is not coated with the elastomeric coating or the non-elastomeric polymer coating.

In some embodiments of the above implantable medical device, the body comprises a bottom surface, and the two or more electrodes are terminate on the bottom of the body.

In some embodiments of the above implantable medical device, the two or more electrodes are positioned on the clip. In some embodiments, the clip comprises a plurality of flexible legs that extend below the body, and the two or more electrodes are positioned on the flexible legs.

In some embodiments of the above implantable medical device, the body comprises a housing. In some embodiments, the housing comprises or is coated with a bioinert material. In some embodiments, the housing comprises the bioinert material, and wherein the bioinert material of the housing comprises titanium or a ceramic. In some embodiments, the body comprises an integrated circuit electrically connected to the ultrasonic transducer and the two or more electrodes.

In some embodiments of the above implantable medical device, the integrated circuit comprises an energy storage circuit comprising a capacitor.

In some embodiments of the above implantable medical device, the body is about 5 mm or less in length in the longest dimension.

In some embodiments of the above implantable medical device, the ultrasonic transducer is configured to emit an ultrasonic backscatter that encodes information related to splenic nerve activity. In some embodiments, the information further comprises information related to a physiological condition, a device status, or an emitted electrical pulse. In some embodiments, the ultrasonic transducer is configured to receive ultrasonic waves that encode instructions for operating the implantable device. In some embodiments, the instructions comprise a trigger signal that operates the implantable device to emit an electrical pulse to the nerve.

In some embodiments of the above implantable medical device, the splenic nerve attachment member is sized and configured to attach the device to the splenic nerve of a human.

In some embodiments of the above implantable medical device, the implantable medical device does not comprise a battery.

In some embodiments of the above implantable medical device, the implantable medical device does not comprise a radiofrequency communication system.

In some embodiments of the above implantable medical device, the implanted medical device does not comprise an electrical lead that extends from the body of the device without terminating on the splenic nerve attachment member.

BRIEF DESCRIPTION OF THE DRAWINGS

In FIG. 8A, the leg includes a single electrode that is positioned along the inner surface of the leg. In FIG. 8B, the leg includes a plurality of electrodes that terminate at different positions along the inner surface of the leg.

DETAILED DESCRIPTION

Figure 1:
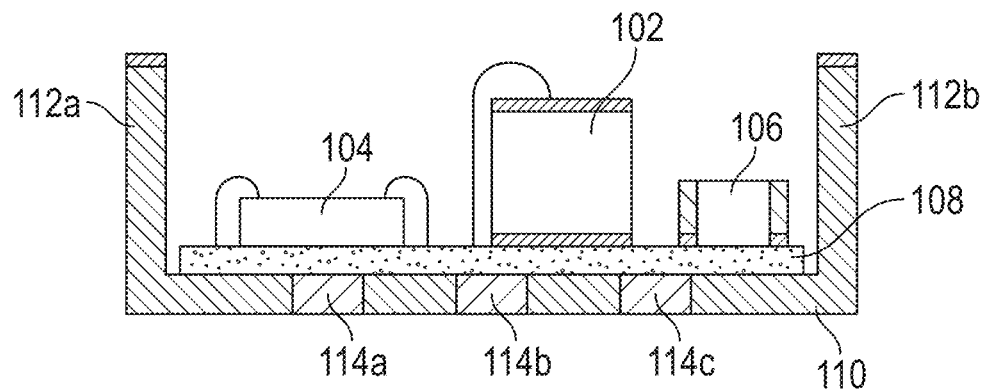
FIG. 1 shows a side view of a body of an implantable device. The body includes an ultrasonic transducer electrically connected to an integrated circuit that includes a power circuit with a capacitor. The body further includes a bottom surface comprising feedthroughs, which allow the integrated circuit to electrically connect with electrodes positioned elsewhere on the device.

Described herein are methods of monitoring or modulating the immune system; treating, reducing or monitoring inflammation; monitoring blood pressure; treating hypertension; or administering or adjusting a therapy for inflammation or hypertension in a patient by electrically stimulating the splenic nerve or detecting splenic nerve activity, for example by using an implanted medical device. The implantable medical device is fully implanted in a subject, and can include a (1) a body having an ultrasonic transducer, (2) two or more electrodes in electrical communication with the ultrasonic transducer, and configured to electrically stimulate the splenic nerve or detect an electrical signal transmitted by the splenic nerve, and (3) a splenic nerve attachment member attached to the body, such a s a clip. The splenic nerve attachment member is sized and configured to attach the device to the splenic nerve or splenic artery, and position the two or more electrodes in electrical communication with the splenic nerve.

The implantable device can receive ultrasonic waves, which may be transmitted by an external ultrasonic transducer, and convert energy from the ultrasonic waves into an electrical energy that powers the implantable device. In some embodiments, the implantable device electrically stimulates the splenic nerve to modulate splenic nerve activity. In some embodiments, the implantable device detects an electrical signal transmitted by the splenic nerve, and emits an ultrasonic backscatter that encodes information related to the detected electrical signal.

Previous implantable devices used a battery powered stimulator attached to a long electrical lead with a terminus positioned in contact with the vagus nerve or other autonomic nerve. The electrical lead extending from the stimulator allowed the relatively large stimulator to be implanted at a position distant from the target nerve. However, the electrical lead is susceptible to damage, and the implanted stimulator is prone to infection because of its large size. Additionally, the battery in the stimulator becomes worn over time, and needs to be replaced through a surgical procedure.

In contrast to known implantable devices for treating inflammation, the implantable device described herein is batteryless, as the ultrasonic transducer converts ultrasonic energy into electrical energy that powers the device. Further, the implantable device does not include electrical leads that extend from the body (other than electrodes positioned on the splenic nerve attachment member attached to the body) to avoid complications with damage and/or breakage of the electrical leads. Instead of electrical leads, the implantable device is small enough that the body of the device can be implanted to directly attach to the nerve. Further, the implantable device is small enough that it can be directly implanted on the splenic nerve, which limits complications due to off-target neural stimulation.

For wireless implanted neurostimulation devices, efficient energy use is a key concern. Wireless power delivery is limited by safety concerns for tissue heating that can cause irreversible damage to a subject. Furthermore, high levels of charge injection through stimulation electrodes can result in water electrolysis and damage to the electrode materials. Thus, stimulation pulse parameters configured to achieve the greatest activation of neural tissue using the smallest amount of charge is generally preferred. For example, in some embodiments, the stimulatory electrical pulse is less than 1 ms in length (for example, about 100 us to about 400 us in length). Pulses of this length can effectively modulate cytokine (e.g., TNF-α, IL-6, IL-1β, and/or HMGB1) levels or immune cell (e.g., NK cell) activation in the subject. The implantable device may stimulate the splenic nerve to effectively modulate cytokine (e.g., TNF-α, IL-6, IL-1β, and/or HMGB1) levels in the subject, while efficiently releasing charge to stimulate the tissue.

For some implantable devices, scenarios where the energy demands of stimulation deplete the energy storage device before it can be sufficiently recharged in order to deliver the next stimulation pulse. For these situations, it may not be desirable to continuously apply electrical pulses to the tissue. It has been found that effect modulation of cytokine levels in the subject can be achieved by applying a pulse train comprising two or more electrical pulses, wherein pulse trains are separated by a dwell time. The dwell time allows the device time to recharge, but still effectively modulate the immune system.

The implantable device is implanted in a subject, which may be a mammal. In some embodiments, the subject is a human, dog, cat, horse, cow, pig, sheep, goat, monkey, or a rodent (such as a rat or mouse). In some embodiments, the subject is anti-cyclic citrullinated peptide (anti-CCP) positive or fails to respond to a disease-modifying anti-rheumatic drug (DMARD). In some embodiments, the subject has hypertension. In some embodiments, the subject has an inflammatory disease which may be an autoimmune disease. By way of example, the inflammatory disease may be, but is not limited to, rheumatoid arthritis, Crohn's disease, colitis, lupus, or spondylitis.

Although the methods provided herein are described using an implanted medical device with an ultrasonic transducer, it is contemplated that the immune system modulation methods may be performed using other suitable devices, which may or may not be fully implanted. Nevertheless, the described implantable device is particularly well-suited for implementing the described immune system modulation methods.

Definitions

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The term "subject" and "patient" are used interchangeably herein to refer to a vertebrate animal.

The terms "treat," "treating," "treatment," and "therapy" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

Methods of Modulating the Immune System

Electrical stimulation of the splenic nerve can modulate the immune system by modulating (such as reducing or increasing) activity of immune cells (such as natural killer (NK) cells) residing in or passing through the spleen, as well as the release of pro-inflammatory cytokines, such as tumor necrosis factor alpha (TNF-α), interleukin-6 (IL-6), interleukin-1 (IL-1) (such as interleukin-1β, IL-β, and high mobility group box 1 (HMGB1). For example, the electrical signal to the splenic nerve can cause increased noradrenaline release, which stimulates T-cells within the spleen to increase acetylcholine release. The acetylcholine signals downregulation of TNF-α and IL-6 release by splenic macrophages, thereby reducing inflammation in the subject. Modulation of the immune system can allow for reducing inflammation in the subject, reducing the release of an inflammatory cytokine in the subject, or reducing the concentration of an inflammatory cytokine in the subject. Inflammation in the subject may be caused by an autoimmune disease, rheumatoid arthritis, Chron's disease, colitis, lupus, spondylitis, an acute injury, or any other inflammatory ailment. Accordingly, the methods described herein may be used to modulate and/or decrease (or increase) blood concentration of one or more inflammatory cytokines (such as TNF-α, IL-6, IL-1β, and/or HMGB1), and/or modulate (increase or decrease) activation of one or more immune cells (such as NK cells).

Reduction of inflammation can be determined using known methods, such as a reduction of swelling in a joint, decreased pain or discomfort reported by the subject, a change in a radiology-based score of inflammation, a reversal of bone or tissue damage caused by inflammation, or by measuring one or more blood markers, such as a cytokine concentration. Cytokines in the blood can be measured by known methods, such as an enzyme-linked immunosorbent assay (ELISA), mass spectrometry, or any other suitable method.

The immune system can be modulated by electrically stimulating the splenic nerve to induce a neurological signal or to block a neurological signal. The direction of immune system modulation (i.e., increase or decrease of cytokine release and/or immune cell (e.g., NK cell) activation) can depend on the amount of charge delivered the splenic nerve (for example, as controlled by pulse length, pulse frequency, and/or current amplitude) and/or polarity of the pulse (or polarity sequence, for a biphasic pulse). For example, a small amount of charge delivered to the splenic nerve can decrease cytokine (e.g., TNF-α) blood levels and/or NK cell activation, whereas a larger amount of charge delivered to the splenic nerve can increase cytokine (e.g., TNF-α) blood levels and/or NK cell activation in the subject. The polarity, such as cathodal or anodal, of the pulse (or sequence of polarity of the pulse in a biphasic pulse, such as cathodal-first or anodal-first), can also impact the evoked response of the splenic nerve thereby altering the efficiency (and impact) of the delivered charge. For example, a cathodal-first, biphasic pulse administered to the splenic nerve requires increased pulse amplitude to obtain the same evoked response as an anodal-first biphasic pulse administered to the splenic nerve.

High frequency versus low frequency electrical stimulation of the splenic nerve using sinusoidal pulses can also impact the direction of immune system modulation. For example, high frequency electrical stimulation (such as between about 1 kHz and about 10 kHz) can block or limit neural activity of the splenic nerve and increase pro-inflammatory cytokine release, whereas low frequency electrical stimulation (such as between about 1 Hz and about 1 kHz) can increase neural activity of the splenic nerve and inhibit or decrease pro-inflammatory cytokine release.

The implantable medical device described herein includes electrodes that are in electrical communication with the splenic nerve of the subject, as well as an ultrasonic transducer that is configured to receive ultrasonic waves that power and operate the implantable device. The implantable device receives ultrasonic waves, for example from an external ultrasonic transducer (e.g., an interrogator), and converts energy from the ultrasonic waves into an electrical energy that powers the implanted medical device. The implantable medical device can then electrically stimulate the splenic nerve.

The implantable medical device is fully implanted in the subject. In some embodiments, the device is fully implanted in the perivascular fascia surrounding the splenic nerve and splenic artery. The splenic nerve need not be separated from the splenic artery. As further described herein, the implantable medical device may include a splenic nerve attachment member that is sized and configured to attach the device to the splenic nerve and/or splenic artery and position the two or more electrodes of the device in electrical communication with the splenic nerve.

To electrically stimulate the splenic nerve, the implanted medical device can emit one or more electrical pulses. The one or more electrical pulses emitted by the implanted device can one or more direct current pulses or one or more alternating current pulses. In some embodiments, the two or more electrical pulses are separated by a dwell time.

In some embodiments, the electrical pulse is about 1 microsecond (µs) or longer (such as about 5 µs or longer, about 10 µs or longer, about 20 µs or longer, about 50 µs or longer, about 100 µs or longer, about 150 µs or longer, about 250 µs or longer, about 500 µs or longer, about 1 millisecond (ms) or longer, about 5 ms or longer, about 10 ms or longer, about 25 ms or longer, about 50 ms or longer, about 100 ms or longer, about 200 ms or longer, or about 500 ms or longer). In some embodiments, the one or more electrical pulses are about 1000 ms or shorter (such as about 500 ms or shorter, about 200 ms or shorter, about 100 ms or shorter, or about 50 ms or shorter, about 25 ms or shorter, about 10 ms or shorter, about 5 ms or shorter, about 1 ms or shorter, about 500 µs or shorter, about 250 µs or shorter, about 150 µs or shorter, about 100 µs or shorter, about 50 µs or shorter, about 20 µs or shorter, about 10 µs or shorter, or about 5 µs or shorter). In some embodiments, the one or more electrical pulses are less than 1 ms in length, such as about 50 µs to about 450 µs in length, about 100 µs to about 400 µs in length, or about 200 µs to about 400 µs in length.

In some embodiments, the dwell time between electrical pulses is about 1 microsecond (µs) or longer (such as about 5 µs or longer, about 10 µs or longer, about 20 µs or longer, about µs or longer, about 100 µs or longer, about 250 µs or longer, about 500 µs or longer, about 1 millisecond (ms) or longer, about 5 ms or longer, about 10 ms or longer, about 25 ms or longer, or about 50 ms or longer). In some embodiments, the dwell time is about 100 ms or shorter (such as about 50 ms or shorter, about 25 ms or shorter, about 10 ms or shorter, about 5 ms or shorter, about 1 ms or shorter, about 500 µs or shorter, about 250 µs or shorter, about 100 µs or shorter, about 50 µs or shorter, about 20 µs or shorter, about 10 µs or shorter, or about 5 µs or shorter).

The implantable device may emit a plurality of electrical pulses in a pulse train, and pulse trains can be separated by a dwell time. In some embodiments, the implantable device charges the power circuit during the dwell time. In some embodiments, the dwell time is about 0.5 seconds or longer (such as about 0.7 seconds or longer, about 1 second or longer, about 1.5 seconds or longer, about 2 seconds or longer, about 5 seconds or longer, or about 10 seconds or longer). In some embodiments, the dwell time between pulse trains is about 15 seconds or less (such as about 10 seconds or less, about 5 seconds or less such as about 4 seconds or less, about 3 seconds or less, about 2 seconds or less, about 1.5 seconds or less, or about 1.5 seconds or less). By way of example, in some embodiments, the dwell time between pulse trains is about seconds to about 15 seconds, or any value therebetween.

In some embodiments, the one or more electrical pulses are about 1 microamp (µA) or more (such as about 5 µA or more, about 10 µA or more, about 25 µA or more, about 50 µA or more, about 100 µA or more, about 250 µA or more, about 500 µA or more, about 1 milliamp (mA) or more, about 5 mA or more, about 10 mA or more, or about 25 mA or more). In some embodiments, the one or more electrical pulses are about 50 mA or less (such as about 25 mA or less, about 10 mA or less, about 5 mA or less, about 1 mA or less, about 500 µA or less, about 250 µA or less, about 100 µA or less, about 50 µA or less, about 25 µA or less, about 10 µA or less, about 5 µA or less, or about 1 µA or less). By way of example, in some embodiments, the amplitude of the one or more electrical pulses is about 500 µA to about 10 mA (such as about 750 µA to about 5 mA, or about 1 mA to about 1.8 mA).

In some embodiments, the one or more electrical pulses have a frequency of about 0.1 Hz or more (such as about 0.5 Hz or more, about 1 Hz or more, about 5 Hz or more, about 10 Hz or more, about 25 Hz or more, about 50 Hz or more, about 100 Hz or more, about 200 Hz or more, about 300 Hz or more, about 400 Hz or more, about 500 Hz or more about 600 Hz or more, about 700 Hz or more, about 800 Hz or more, about 1 kHz or more, about 2 kHz or more, or about 5 kHz or more). In some embodiments, the one or more electrical pulses have a frequency of about 10 kHz or less (such as about 5 kHz or less, about 2 kHz or less, about 1 kHz or less, about 800 Hz or less, about 700 Hz or less, about 600 Hz or less, about 500 Hz or less, about 400 Hz or less, about 300 Hz or less, about 200 Hz or less, about 100 Hz or less, about 50 Hz or less, about 25 Hz or less, about 10 Hz or less, about 5 Hz or less, about 1 Hz or less, or about 0.5 Hz or less).

In some embodiments, the implanted medical device generates a voltage pulse in the splenic nerve. In some embodiments, the voltage is about 50 mV or more (such as about 100 mV or more, about 250 mV or more, about 500 mV or more about 1 V or more, about 2.5 V or more, about 5 V or more, or about 10 V or more). In some embodiments, the voltage is about 20 V or less (such as about 15 V or less, about 10 V or less, about 5 V or less, about 2.5 V or less, about 1 V or less, about 500 mV or less, about 250 mV or less, or about 100 mV or less).

The electrical pulses administered to the splenic nerve may be sinusoidal, square, sawtooth, or any other suitable shape. The electrical pulses may be monophasic (i.e., having only a cathodal phase or only an anodal phase) or biphasic (i.e., having both cathodal phase and anodal phase). A "biphasic pulse" as used herein refers to a single pulse with an anodal phase and a cathodal phase. The order of the cathodal phase and the anodal phase in a biphasic pulse may be in either order (i.e., anodal-first or cathodal-first). The anodal phase and the cathodal phase of the biphasic pulse may be separated by an interphase interval (for example about 10 µs to about 150 µs in length, such as about 10 µs to about 20 µs, about 20 µs to about 40 µs, about 40 µs to about 60 µs, about 60 µs to about 80 µs, about 80 µs to about 100 µs, or about 100 µs to about 150 µs in length). The interphase interval is generally short enough to allow for reversal of incidental redox reactions, long enough to allow for substantial depolarization of the nerve before the charge is reversed. The length of a biphasic pulse refers to the length of the anodal phase and the cathodal phase, and excludes the length of any optionally present interphase interval of the biphasic pulse.

In some embodiments, there is a method of modulating an immune system of a subject (such as modulating, either by increasing or decreasing, a blood concentration of an inflammatory cytokine (e.g., one or more of TNF-α, IL-6, IL-1β or HMGB1) and/or modulating, either by increasing or decreasing, the activation of one or more immune cells (e.g., NK cells), comprising electrically stimulating the splenic nerve of the subject. In some embodiments, the splenic nerve is electrically stimulated using a pulse train comprising a plurality of electrical pulses. The electrical pulses of the pulse train may comprise, for example, square wave pulses or sinusoidal pulses. In some embodiments, the square wave pulses are monophasic (for example, a cathodal square wave pulse or an anodal square wave pulse) and some embodiments the square wave pulses are biphasic (comprising an anodal phase and a cathodal phase), which are optionally separated by an interphase interval. In some embodiments of the biphasic pulse, the anodal phase is followed by the cathodal phase, and in some embodiments of the biphasic pulse, the cathodal phase is followed by the anodal phase. In some embodiments, the electrical pulses are less than 1 ms in length. In some embodiments, the frequency of the electrical pulses is about 100 Hz or less. The method may be implemented, for example, using an implantable device, such as a fully implantable device described herein. In some embodiments, the method further comprises receiving ultrasonic waves from an external ultrasonic transducer; converting energy from the ultrasonic waves into electrical energy that powers a fully implanted medical device in the subject, the device comprising two or more electrodes that are in electrical communication with the splenic nerve of the subject.

In some embodiments, there is a method of modulating an immune system of a subject (such as modulating, either by increasing or decreasing, a blood concentration of one or more inflammatory cytokines (e.g., one or more of TNF-α, IL-6, IL-1β or HMGB1) and/or modulating, either by increasing or decreasing, the activation of one or more immune cells (e.g., NK cells), comprising electrically stimulating the splenic nerve of the subject using a pulse train comprising a plurality of biphasic electrical pulses. The electrical pulses of the pulse train may comprise, for example, square wave pulses or sinusoidal pulses. In some embodiments of the biphasic pulse, the anodal phase is followed by the cathodal phase, and in some embodiments of the biphasic pulse, the cathodal phase is followed by the anodal phase. In some embodiments, the electrical pulses are less than 1 ms in length. In some embodiments, the frequency of the electrical pulses is about 100 Hz or less. The method may be implemented, for example, using an implantable device, such as a fully implantable device described herein. In some embodiments, the method further comprises receiving ultrasonic waves from an external ultrasonic transducer; converting energy from the ultrasonic waves into electrical energy that powers a fully implanted medical device in the subject, the device comprising two or more electrodes that are in electrical communication with the splenic nerve of the subject.

Electrical stimulation of the splenic nerve can occur in response to a trigger signal. In some embodiments, the ultrasonic waves received by the implantable medical device encode the trigger signal, which instructs the implantable medical device to electrically stimulate the splenic nerve. The trigger signal may include instructions that include a frequency, amplitude, duration, pulse pattern, pulse shape, or dwell time of the electrical pulse emitted by the implantable device. For example, the trigger signal can instruct the implantable device to stimulate the splenic nerve with a first frequency to stimulate neural activity, and a second frequency to block neural activity.

The trigger signal can be based activity of the splenic nerve, a change in an immune system status, an increase or decrease in inflammation, or an inflammatory response. As further described herein, the implantable medical device can be configured to detect splenic nerve activity, and emit an ultrasonic backscatter that encodes information related to the splenic nerve activity. The ultrasonic backscatter can be received by an interrogator, which can decode the ultrasonic backscatter to obtain the information related to the splenic nerve activity. The information can be analyzed by the interrogator or relayed to another computer system to analyze the information. Based on the activity of the splenic nerve, the interrogator can transmit the trigger signal to the implanted medical device, instructing the device to electrically stimulate the splenic nerve. In some embodiments, the trigger signal is based on increase in splenic nerve activity compared to a baseline splenic nerve activity. A baseline splenic nerve activity can be established in an individual subject, for example, and the trigger signal can be based on deviations from the baseline splenic nerve activity.

The trigger signal can be based on, for example, a voltage potential change or a voltage potential change pattern measured from the splenic nerve over a period of time. The voltage change (e.g., a voltage spike) is indicative of the action potential passing through the splenic nerve, which is detected by the electrodes on the implanted device. A difference in the a frequency and/or amplitude of the voltage spike (a single voltage spike or a compound voltage spike of the action potential) can indicate a change in immune activity, which may be modulated by emitting one or more electrical pulses to the splenic nerve.

The trigger system may also be based on one or more additional or alternative factors, such as a physiological condition, which may be measured by the implantable medical device or any other device or method. Exemplary physiological conditions that the trigger signal may be based on include, but are not limited to, a temperature, a blood pressure, or a pulse rate. Physiological conditions may demonstrate that the immune system should not be modulated or modulated using a different electrical pulse pattern for some reason, such as an acute illness, for example if the subject has a fever.

In some embodiments, the trigger signal is based on an analysis of splenic nerve activity patterns and a detected physiological condition, such as temperature, pulse, or blood pressure. The splenic nerve activity may be detected by the implantable medical device or by some other device or method.

In some embodiments, the trigger signal can be based on information related to aggregate information (e.g., splenic nerve activity and/or physiological condition) detected over a trailing period of time, for example over a period of minutes, hours, or days. For example, in some embodiments, the trigger is based on information related to splenic nerve activity detected from within about 30 seconds, about 1 minute, about 5 minutes about 15 minutes, about 30 minutes, about 1 hour, about 2 hours, about 4 hours, about 8 hours, about 12 hours, about 24 hours, about 2 days, about 4 days, or about 7 days.

In some embodiments, the implanted medical device can be operated using an interrogator, which can transmit ultrasonic waves that power and operate the implanted device. As further described herein, the interrogator is a device that includes an ultrasonic transducer that can transmit ultrasonic waves to the implanted device and/or receive ultrasonic backscatter emitted from the implanted device. In some embodiments, the interrogator is a device external to the subject, and can be worn by the subject. In some embodiments, the ultrasonic waves transmitted by the interrogator encode the trigger signal.

In one example, a method of modulating the immune system of a subject comprises receiving ultrasonic waves from an external ultrasonic transducer; converting energy from the ultrasonic waves into an electrical energy that powers a fully implanted medical device in the subject, the device comprising two or more electrodes that are in electrical communication with the splenic nerve of the subject; and electrically stimulating the splenic nerve using the device. In some embodiments, electrically stimulating the splenic nerve occurs in response to a trigger signal. In some embodiments, the trigger signal is encoded in the ultrasonic waves received by the implanted medical device, which may be transmitted by an external interrogator. In some embodiments, the trigger signal is based on splenic nerve activity, such as a deviation from a baseline splenic nerve activity. In some embodiments, the trigger signal is further based on a physiological condition, such as a temperature, a pulse rate, and/or a blood pressure. In some embodiments, the splenic nerve activity and/or the physiological condition is detected or measured by the implanted medical device, and information related to the splenic nerve activity or the physiological condition is encoded in an ultrasonic backscatter emitted by the implanted medical device. In some embodiments, the method comprises emitting an ultrasonic backscatter encoding information related to the splenic nerve activity or the physiological condition, which may be received by an external device (such as an interrogator).

In another example, there is a method of reducing inflammation in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce inflammation in the subject. In some embodiments, inflammation in the subject is caused by an autoimmune disease. In some embodiments, the inflammation in the subject is caused by rheumatoid arthritis, Crohn's disease, colitis, lupus, or spondylitis. In some embodiments, the method comprises monitoring inflammation in the subject. In some embodiments, electrically stimulating the splenic nerve occurs in response to a trigger signal. In some embodiments, the trigger signal is encoded in the ultrasonic waves received by the implanted medical device, which may be transmitted by an external interrogator. In some embodiments, the trigger signal is based on splenic nerve activity, such as a deviation from a baseline splenic nerve activity. In some embodiments, the trigger signal is further based on a physiological condition, such as a temperature, a pulse rate, and/or a blood pressure. In some embodiments, the splenic nerve activity and/or the physiological condition is detected or measured by the implanted medical device, and information related to the splenic nerve activity or the physiological condition is encoded in an ultrasonic backscatter emitted by the implanted medical device. In some embodiments, the method comprises emitting an ultrasonic backscatter encoding information related to the splenic nerve activity or the physiological condition, which may be received by an external device (such as an interrogator).

In some embodiments, there is a method of reducing a blood concentration of an inflammatory cytokine (such as tumor necrosis factor alpha (TNF-$\alpha$), interleukin-6 (IL-6), interleukin-1 (IL-1) (such as IL-1$\beta$), or high mobility group box 1 (HMGB1)) in a subject, comprising: receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce the blood concentration of the inflammatory cytokine in the subject. In some embodiments, the method reduces splenic release of the inflammatory cytokine. In some embodiments, the method comprises measuring the blood concentration of the inflammatory cytokine. In some embodiments, electrically stimulating the splenic nerve occurs in response to a trigger signal. In some embodiments, the trigger signal is encoded in the ultrasonic waves received by the implanted medical device, which may be transmitted by an external interrogator. In some embodiments, the trigger signal is based on splenic nerve activity, such as a deviation from a baseline splenic nerve activity. In some embodiments, the trigger signal is further based on a physiological condition, such as a temperature, a pulse rate, and/or a blood pressure. In some embodiments, the splenic nerve activity and/or the physiological condition is detected or measured by the implanted medical device, and information related to the splenic nerve activity or the physiological condition is encoded in an ultrasonic backscatter emitted by the implanted medical device. In some embodiments, the method comprises emitting an ultrasonic backscatter encoding information related to the splenic nerve activity or the physiological condition, which may be received by an external device (such as an interrogator).

Methods of Monitoring Immune System Status or Inflammation in a Subject

The implanted medical device can be used to monitor an immune system status or inflammation in an individual. As discussed above, splenic nerve activity is associated with activity of immune cells that reside in or pass through the spleen, as well as splenic cytokine release, including pro-inflammatory cytokines such as TNF-α, IL-6, IL-1 (e.g., IL-1β), and HMGB1. Therefore, monitoring splenic nerve activity allows for monitoring of the immune system and inflammation. As further described herein, the implanted medical device can include two or more electrodes configured to detect splenic nerve activity. The two or more electrodes configured to detect splenic nerve activity may be the same or different as the two or more electrodes configured to electrically stimulate the splenic nerve.

Monitoring the immune system status through splenic nerve activity can allow for monitoring of an onset, offset, or magnitude of an immune response, such as an inflammatory response. Additionally, changes of the splenic nerve activity detected by the implanted medical device can provide information related to an inflammatory disease, such as an autoimmune disease, rheumatoid arthritis, Crohn's disease, colitis, lupus, or spondylitis. Therefore, the methods described herein allow for monitoring the inflammatory disease or an anti-inflammatory therapy. Monitoring of the immune system response also allows for adjustments to various therapies, including anti-inflammatory therapy, as further described herein.

A change in the status of the immune system may be detected by an increase in splenic nerve activity, a decrease in splenic nerve activity, or a change in a pattern of splenic nerve activity compared to a baseline splenic nerve activity. For example, in some embodiments, an increase in inflammation is indicated by a decrease in splenic nerve activity or a change in a pattern of splenic nerve activity.

The implanted medical device for monitoring the immune system includes an ultrasonic transducer configured to emit an ultrasonic backscatter encoding information related splenic nerve activity. The information can include, for example, information related to an electrophysiological pulse transmitted by the splenic nerve, such as a frequency, voltage, shape or pulse pattern. The ultrasonic backscatter waves encoding the information can be received by an interrogator and analyzed to decode the information. The ultrasonic transducer of the implanted medical device can also receive ultrasonic waves that power the implanted device, which may be transmitted by the interrogator configured to receive the ultrasonic backscatter or a separate interrogator. The ultrasonic transducers on the implanted medical device receives the ultrasonic waves from an external transducer and converts energy from the ultrasonic waves into electrical energy that powers the implanted medical device.

Electrical current flows through the ultrasonic transducer, and the electrical current can be modulated to encode the information related to the splenic nerve activity. For example, the implanted medical device can include an integrated circuit electrically connected to the ultrasonic transducer and the electrodes configured to detect the splenic nerve activity. The integrated circuit can include a modulation circuit, which modulates the electrical current to encode the information related to the splenic nerve activity. Since the ultrasonic backscatter is affected by the electrical current flowing through the ultrasonic transducer, the ultrasonic backscatter emitted by the ultrasonic transducer encodes the splenic nerve activity information encoded into the modulated electrical current.

Deviation in the electrical signal detected by the implanted medical device indicates a change in the status of the immune system. For example, an increase in voltage potential of the splenic nerve over a period of time indicates increased inflammation in the subject. From the deviation of a baseline signal of splenic nerve activity, it is possible to determine an onset, offset, and a magnitude of an inflammatory response.

The ultrasonic backscatter emitted by the implanted medical device can be received by an external device (e.g., an interrogator), and the information encoded in the ultrasonic backscatter can be analyzed to determine the status of the immune system or a change in the status of the immune system, such as an inflammatory response.

A change in the immune response, such as an increase in inflammation, can indicate that a therapy, such as an anti-inflammatory therapy, should be administered to the subject.

Accordingly, in some embodiments, a therapy, such as an anti-inflammatory therapy, is administered to the subject in response to a change in the immune system status. In some embodiments, a drug therapy is administered to the subject in response to a change in the status of the immune system. In some embodiments, the therapy is an electrical stimulation of a nerve, such as the vagus nerve, the splenic nerve, the celiac ganglion, the sub-diaphragmatic vagus nerve, a splanchnic nerve, and/or a superior mesenteric nerve.

In one example, there is a method of monitoring an immune system of a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; and emitting an ultrasonic backscatter encoding information related to the electrical activity of the splenic nerve, wherein a deviation in the electrical activity indicates a change in the status of the immune system of the subject. In some embodiments, the method comprises receiving the ultrasonic backscatter at an external device (e.g., an interrogator).

In some embodiments, there is a method of monitoring inflammation in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; and emitting an ultrasonic backscatter encoding information related to the electrical activity of the splenic nerve; and monitoring deviation in the electric activity, wherein a deviation in the electrical activity indicates a change in inflammation in the subject. In some embodiments, an increase in the electrical activity indicates an increase in inflammation. In some embodiments, a decrease in the electrical activity indicates a decrease in inflammation. In some embodiments, a change in an identifiable pattern of electrical activity (e.g., a change in voltage amplitude or frequency) indicates a decrease in inflammation. In some embodiments, the inflammation is caused by an autoimmune disease, rheumatoid arthritis, Crohn's disease, colitis, lupus, or spondylitis. In some embodiments, an anti-inflammatory therapy, such as an anti-inflammatory drug or electrical stimulation of a nerve, is administered to the subject in response to an increase in inflammation. In some embodiments, the method comprises receiving the ultrasonic backscatter at an external device (e.g., an interrogator).

In some embodiments, there is a method of monitoring an inflammatory response in a subject, comprising receiving ultrasonic waves from an external ultrasonic transducer;

converting energy from the ultrasonic waves into electrical energy that powers a fully implanted medical device in the subject, the device comprising two or more electrodes that contact the splenic nerve of the subject; detecting an electrical activity of the splenic nerve; and emitting an ultrasonic backscatter encoding information related to the electrical activity of the splenic nerve; and monitoring a deviation in the electric activity, wherein an increase in the electrical activity indicates an inflammatory response in the subject. In some embodiments, an increase in the electrical activity indicates an increase in inflammation. In some embodiments, a decrease in the electrical activity indicates a decrease in inflammation. In some embodiments, a change in an identifiable pattern of electrical activity indicates a decrease in inflammation. In some embodiments, an anti-inflammatory therapy, such as an anti-inflammatory drug or electrical stimulation of a nerve, is administered to the subject in response to the inflammatory response. In some embodiments, the method comprises receiving the ultrasonic backscatter at an external device (e.g., an interrogator).

In some embodiments, there is a method of monitoring an anti-inflammatory therapy in a subject, comprising; receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; and emitting an ultrasonic backscatter encoding information related to the electrical activity of the splenic nerve; and monitoring a deviation in the electric activity, wherein a deviation in the electrical activity indicates a response to the anti-inflammatory therapy. In some embodiments, the method comprises administering the anti-inflammatory therapy to the subject. In some embodiments, the anti-inflammatory therapy is a drug therapy or electrical stimulation of a nerve (such as a vagus nerve, a splenic nerve, a celiac ganglion, a sub-diaphragmatic vagus nerve, a splanchnic nerve, or a superior mesenteric nerve. In some embodiments, the method comprises receiving the ultrasonic backscatter at an external device (e.g., an interrogator).

Methods of Administering or Adjusting a Therapy for Inflammation

As discussed above, the implanted medical device can detect splenic nerve activity, and changes in the splenic nerve activity can indicate an increase or decrease in an inflammatory response in the subject. Based on the splenic nerve activity detected by the implantable device, the immune system, and thus an inflammatory response, can be monitored. In some embodiments, if deviation in the splenic activity indicates an inflammatory response, an anti-inflammatory therapy can be administered to the subject. In some embodiments, an anti-inflammatory therapy is adjusted in response to a change in the inflammatory response status of the individual.

Exemplary therapies that may be adjusted include, but are not limited to, electrical stimulation of a nerve or administration of a drug. Exemplary nerves that may be stimulated include the splenic nerve, the vagus nerve, the celiac ganglion, the sub-diaphragmatic vagus nerve, a splanchnic nerve, and/or a superior mesenteric nerve. Exemplary drugs include, but are not limited to, an anti-inflammatory drug, such as a TNF-α inhibitor, a IL-6 inhibitor, an IL-1 inhibitor (e.g., an IL-1β inhibitor), or a disease-modifying antirheumatic drug (DMARD). For example, the anti-inflammatory drug may be any one or more of abatacept, adalimumab, azathioprine, certolizumab pegol, cyclophosphamide, cyclosporine, entracept, golimumab, hydroxychloroquine sulfate, infliximab, leflunomide, methotrexate, mycophenolate mofetil, rituximab, sulfasalazine, or tocilizumab.

In some embodiments, the implantable medical device described herein operates in a closed-loop (i.e., feedback) system to administer an anti-inflammatory therapy. For example, the implanted medical device can be used to detect an inflammatory response based on splenic nerve activity, and electrically stimulates the splenic nerve if the inflammatory response is detected. In some embodiments, the implanted medical device electrically stimulates the splenic nerve to block the splenic nerve activity. Information related to the splenic nerve activity can be encoded in an ultrasonic backscatter emitted by the ultrasonic transducer of the implanted medical device, which can be received by an interrogator. Deviation of the electrical activity of the splenic nerve can be monitored, and an anti-inflammatory therapy can be administered if the electrical activity of the splenic nerve indicates and inflammatory response.

The implanted medical device need not be used to both detect splenic nerve activity and administer the electrical stimulation of splenic nerve, as additional or alternative anti-inflammatory therapies may be administered. For example, the anti-inflammatory therapy may be an electrical stimulation of a nerve other than the splenic nerve, such as the vagus nerve, the celiac ganglion, the sub-diaphragmatic vagus nerve, a splanchnic nerve, and/or a superior mesenteric nerve. Stimulation of the nerve may be automatic, or may be controlled by the subject. In some embodiments, the anti-inflammatory therapy is a drug therapy.

By way of example, in some embodiments, there is a method of administering a therapy for inflammation in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; detecting an electrical activity of the splenic nerve; emitting an ultrasonic backscatter encoding the electric activity of the splenic nerve; monitoring a deviation in the electric activity of the splenic nerve; and administering the anti-inflammatory therapy if the deviation in the electrical activity of the splenic nerve indicates an inflammatory response. In some embodiments, the anti-inflammatory therapy is stimulation of a nerve, such as the splenic nerve, the vagus nerve, the celiac ganglion, the sub-diaphragmatic vagus nerve, a splanchnic nerve, and/or a superior mesenteric nerve. In some embodiments, the anti-inflammatory therapy is a drug therapy.

The implanted medical device can also be used to adjust a therapy administered to a subject based on an immune response (e.g., inflammatory response) to that therapy. The therapy may be an anti-inflammatory therapy, or some other therapy that may affect the immune response of the subject. For example, the drug with an inflammatory side effect may be administered to the patient, and the dosage of the drug may be adjusted based on an inflammatory response. The therapy may be adjusted if the therapy does not result in a desired effect or if the therapy causes an undesired inflammatory response. In some embodiments, the therapy (e.g., anti-inflammatory therapy) is discontinued if the therapy obtains a desired effect.

In some embodiments, adjustments to the therapy may be an adjustment to the frequency or dosage the therapy (e.g., a drug therapy) is administered to the subject. In some embodiments, the adjustments to the therapy may be an adjustment to a frequency, pattern, or amplitude of an electrical stimulation of a nerve.

Methods of Modulating Blood Pressure or Treating Hypertension

Electrical stimulation of the splenic nerve can also be used to adjust a cardiovascular state of a subject using the implantable medical device. For example, electrical stimulation of the splenic nerve can be used to modulate blood pressure or treat hypertension in a subject. The link between the nervous system, the immune system, and blood pressure has been previously established. See Carnevale et al., *A cholinergic-sympathetic pathway primes immunity in hypertension and mediates brain-to-spleen communication*, Nature Communications, vol. 7 (2016). Splenic nerve activity and immune function is associated with blood pressure and a hypertensive state of a subject. As described herein, modulation of splenic nerve activity using an implanted medical device is used to modulate blood pressure and/or treat hypertension in a subject.

Blood pressure can be modulated by electrically stimulating the splenic nerve to induce a neurological signal or to block a neurological signal. For example, high frequency electrical stimulation (such as between about 1 kHz and about 10 kHz) can block or limit neural activity of the splenic nerve to decrease blood pressure and/or reduce hypertension, whereas low frequency electrical stimulation (such as between about 1 Hz and about 1 kHz) applied at high amplitudes can increase neural activity of the splenic nerve to increase blood pressure.

The implantable medical device described herein includes electrodes that are in electrical communication with the splenic nerve of the subject, as well as an ultrasonic transducer that is configured to receive ultrasonic waves that power and operate the implantable device. The implantable device receives ultrasonic waves, for example from an external ultrasonic transducer (e.g., an interrogator), and converts energy from the ultrasonic waves into an electrical energy that powers the implanted medical device. The implantable medical device can then electrically stimulate the splenic nerve to modulate blood pressure and/or treat hypertension.

The implantable medical device is fully implanted in the subject, with electrodes in electrical communication with the splenic nerve. In some embodiments, the device is fully implanted in the perivascular fascia surrounding the splenic nerve and splenic artery. The splenic nerve need not be separated from the splenic artery. As further described herein, the implantable medical device may include a splenic nerve attachment member that is sized and configured to attach the device to the splenic nerve and/or splenic artery and position the two or more electrodes of the device in electrical communication with the splenic nerve.

To electrically stimulate the splenic nerve, the implanted medical device can emit one or more electrical pulses configured to modulate blood pressure and/or treat hypertension. The one or more electrical pulses emitted by the implanted device can include one or more direct current pulses or one or more alternating current pulses. In some embodiments, the two or more electrical pulses are separated by a dwell time.

In some embodiments, the electrical pulse is about 1 microsecond ($\mu s$) or longer (such as about 5 $\mu s$ or longer, about 10 $\mu s$ or longer, about 20 $\mu s$ or longer, about 50 $\mu s$ or longer, about 100 $\mu s$ or longer, about 250 $\mu s$ or longer, about 500 $\mu s$ or longer, about 1 millisecond (ms) or longer, about 5 ms or longer, about 10 ms or longer, about 25 ms or longer, about 50 ms or longer, about 100 ms or longer, about 200 ms or longer, or about 500 ms or longer). In some embodiments, the one or more electrical pulses are about 1000 ms or shorter (such as about 500 ms or shorter, about 200 ms or shorter, about 100 ms or shorter, or about 50 ms or shorter, about ms or shorter, about 10 ms or shorter, about 5 ms or shorter, about 1 ms or shorter, about 500 $\mu s$ or shorter, about 250 $\mu s$ or shorter, about 100 $\mu s$ or shorter, about 50 $\mu s$ or shorter, about 20 $\mu s$ or shorter, about 10 $\mu s$ or shorter, or about 5 $\mu s$ or shorter).

In some embodiments, the dwell time between electrical pulses is about 1 microsecond ($\mu s$) or longer (such as about 5 $\mu s$ or longer, about 10 $\mu s$ or longer, about 20 $\mu s$ or longer, about $\mu s$ or longer, about 100 $\mu s$ or longer, about 250 $\mu s$ or longer, about 500 $\mu s$ or longer, about 1 millisecond (ms) or longer, about 5 ms or longer, about 10 ms or longer, about 25 ms or longer, or about 50 ms or longer). In some embodiments, the dwell time is about 100 ms or shorter (such as about 50 ms or shorter, about 25 ms or shorter, about 10 ms or shorter, about 5 ms or shorter, about 1 ms or shorter, about 500 $\mu s$ or shorter, about 250 $\mu s$ or shorter, about 100 $\mu s$ or shorter, about 50 $\mu s$ or shorter, about 20 $\mu s$ or shorter, about 10 $\mu s$ or shorter, or about 5 $\mu s$ or shorter).

In some embodiments, the one or more electrical pulses are about 1 microamp ($\mu A$) or more (such as about 5 $\mu A$ or more, about 10 $\mu A$ or more, about 25 $\mu A$ or more, about 50 $\mu A$ or more, about 100 $\mu A$ or more, about 250 $\mu A$ or more, about 500 $\mu A$ or more, about 1 milliamp (mA) or more, about 5 mA or more, about 10 mA or more, or about 25 mA or more). In some embodiments, the one or more electrical pulses are about 50 mA or less (such as about 25 mA or less, about 10 mA or less, about 5 mA or less, about 1 mA or less, about 500 $\mu A$ or less, about 250 $\mu A$ or less, about 100 $\mu A$ or less, about 50 $\mu A$ or less, about 25 $\mu A$ or less, about 10 $\mu A$ or less, about 5 $\mu A$ or less, or about 1 $\mu A$ or less.

In some embodiments, the one or more electrical pulses have a frequency of about 0.1 Hz or more (such as about 0.5 Hz or more, about 1 Hz or more, about 5 Hz or more, about 10 Hz or more, about 25 Hz or more, about 50 Hz or more, about 100 Hz or more, about 200 Hz or more, about 300 Hz or more, about 400 Hz or more, about 500 Hz or more about 600 Hz or more, about 700 Hz or more, about 800 Hz or more, about 1 kHz or more, about 2 kHz or more, or about 5 kHz or more). In some embodiments, the one or more electrical pulses have a frequency of about 10 kHz or less (such as about 5 kHz or less, about 2 kHz or less, about 1 kHz or less, about 800 Hz or less, about 700 Hz or less, about 600 Hz or less, about 500 Hz or less, about 400 Hz or less, about 300 Hz or less, about 200 Hz or less, about 100 Hz or less, about 50 Hz or less, about 25 Hz or less, about 10 Hz or less, about 5 Hz or less, about 1 Hz or less, or about 0.5 Hz or less).

In some embodiments, the implanted medical device generates a voltage pulse in the splenic nerve. In some embodiments, the voltage is about 50 mV or more (such as about 100 mV or more, about 250 mV or more, about 500 mV or more about 1 V or more, about 2.5 V or more, about 5 V or more, or about 10 V or more). In some embodiments, the voltage is about 20 V or less (such as about 15 V or less, about 10 V or less, about 5 V or less, about 2.5 V or less, about 1 V or less, about 500 mV or less, about 250 mV or less, or about 100 mV or less).

Electrical stimulation of the splenic nerve to modulate blood pressure and/or treat hypertension can occur in response to a trigger signal. In some embodiments, the ultrasonic waves received by the implantable medical device encode the trigger signal, which instructs the implantable medical device to electrically stimulate the splenic nerve.

The trigger signal may include instructions that include a frequency, amplitude, duration, pulse pattern, pulse shape, or dwell time of the electrical pulse emitted by the implantable device. For example, the trigger signal can instruct the implantable device to stimulate the splenic nerve with a first frequency to stimulate neural activity, and a second frequency to block neural activity.

The trigger signal can be based on splenic nerve activity or blood pressure, or a change in the splenic nerve activity or blood pressure. Blood pressure may be measured using the implanted medical device, or by any other suitable device. As further described herein, the implantable medical device can be configured to detect splenic nerve activity, and emit an ultrasonic backscatter that encodes information related to the splenic nerve activity and/or blood pressure. The ultrasonic backscatter can be received by an interrogator, which can decode the ultrasonic backscatter to obtain the information related to the splenic nerve activity and/or blood pressure. The information can be analyzed by the interrogator or relayed to another computer system to analyze the information. Based on the activity of the splenic nerve and/or measured blood pressure, the interrogator can transmit the trigger signal to the implanted medical device, instructing the device to electrically stimulate the splenic nerve. In some embodiments, the trigger signal is based on increase in splenic nerve activity compared to a baseline splenic nerve activity. A baseline splenic nerve activity can be established in an individual subject, for example, and the trigger signal can be based on deviations from the baseline splenic nerve activity.

The trigger signal can be based on, for example, a voltage potential change or a voltage potential change pattern measured from the splenic nerve over a period of time. The voltage change (e.g., a voltage spike) is indicative of the action potential passing through the splenic nerve, which is detected by the electrodes on the implanted device. A difference in the frequency and/or amplitude of the voltage spike (a single voltage spike or a compound voltage spike of the action potential) can be detected, and one or more electrical pulses may be emitted to stimulate the splenic nerve. In some embodiments, the trigger signal is based on an analysis of splenic nerve activity patterns and a measured blood pressure.

In some embodiments, the trigger signal can be based on information related to aggregate information (e.g., splenic nerve activity and/or blood pressure) detected over a trailing period of time, for example over a period of minutes, hours, or days. For example, in some embodiments, the trigger is based on information related to splenic nerve activity detected from within about 30 seconds, about 1 minute, about 5 minutes about 15 minutes, about 30 minutes, about 1 hour, about 2 hours, about 4 hours, about 8 hours, about 12 hours, about 24 hours, about 2 days, about 4 days, or about 7 days.

In some embodiments, the implanted medical device can be operated using an interrogator, which can transmit ultrasonic waves that power and operate the implanted device. As further described herein, the interrogator is a device that includes an ultrasonic transducer that can transmit ultrasonic waves to the implanted device and/or receive ultrasonic backscatter emitted from the implanted device. In some embodiments, the interrogator is a device external to the subject, and can be worn by the subject. In some embodiments, the ultrasonic waves transmitted by the interrogator encode the trigger signal.

In one example, there is a method of modulating blood pressure in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to modulate blood pressure in the subject. In some embodiments, the method further comprises measuring the blood pressure of the subject. In some embodiments, the blood pressure is measured using the implanted medical device, and may be determined from splenic nerve activity. In some embodiments, the splenic nerve is electrically stimulated at a frequency of about 1 kHz or higher (such as about 1 kHz to about 10 kHz). In some embodiments, electrically stimulating the splenic nerve occurs in response to a trigger signal. In some embodiments, the trigger signal is encoded in the ultrasonic waves received by the implanted medical device, which may be transmitted by an external interrogator. In some embodiments, the trigger signal is based on splenic nerve activity, such as a deviation from a baseline splenic nerve activity, and/or a measured blood pressure. In some embodiments, the method comprises emitting an ultrasonic backscatter encoding information related to the splenic nerve activity and/or blood pressure, which may be received by an external device (such as an interrogator).

In some embodiments, there is a method of treating hypertension in a subject, comprising receiving ultrasonic waves from an external ultrasonic transducer; converting energy from the ultrasonic waves into electrical energy that powers a fully implanted medical device in the subject, the device comprising two or more electrodes that contact the splenic nerve of the subject; and electrically stimulating the splenic nerve using the device, wherein the stimulation is configured to reduce hypertension in the subject. In some embodiments, the method further comprises measuring the blood pressure of the subject. In some embodiments, the blood pressure is measured using the implanted medical device, and may be determined from splenic nerve activity. In some embodiments, the splenic nerve is electrically stimulated at a frequency of about 1 kHz or higher (such as about 1 kHz to about 10 kHz). In some embodiments, electrically stimulating the splenic nerve occurs in response to a trigger signal. In some embodiments, the trigger signal is encoded in the ultrasonic waves received by the implanted medical device, which may be transmitted by an external interrogator. In some embodiments, the trigger signal is based on splenic nerve activity, such as a deviation from a baseline splenic nerve activity, and/or a measured blood pressure. In some embodiments, the method comprises emitting an ultrasonic backscatter encoding information related to the splenic nerve activity and/or blood pressure, which may be received by an external device (such as an interrogator).

Methods of Monitoring Blood Pressure and Hypertension

Neural activity of autonomic nerves in a subject has been associated with the blood pressure of a subject. See, for example, Hellyer et al., *Autonomic Nerve Activity and Blood Pressure in Ambulatory Dogs*, Heart Rhythm, vol. 11, no. 2, pp. 307-313 (2014). Autonomic nerve activity (such as splenic nerve activity or vagal nerve activity) can be detected and analyzed to monitor a blood pressure or hypertension in the subject.

In some embodiments, splenic nerve activity is detected using an implanted medical device having two or more electrodes in electrical communication with the splenic nerve, and the detected splenic nerve activity can be used to monitor blood pressure or hypertension in the subject. For example, the change in splenic nerve activity can be used to determine if there is an increase or a decrease in blood pressure in the subject. The two or more electrodes configured to detect splenic nerve activity may be the same or different as the two or more electrodes configured to electrically stimulate the splenic nerve.

In some embodiments, the implanted medical device includes a pressure sensor, which can be used to measure or monitor the blood pressure. For example the pressure sensor may be a microelectromechanical system (MEMS) sensor.

The implanted medical device includes an ultrasonic transducer configured to emit an ultrasonic backscatter encoding information related splenic nerve activity and/or blood pressure, which may be obtained using the pressure sensor or be inferred from the splenic nerve activity. The information can include, for example, information related to an electrophysiological pulse transmitted by the splenic nerve, such as a frequency, voltage, shape, or pulse pattern, or information related to a change of the electrophysiological pulse. The ultrasonic backscatter waves encoding the information can be received by an interrogator and analyzed to decode the information. The ultrasonic transducer of the implanted medical device can also receive ultrasonic waves that power the implanted device, which may be transmitted by the interrogator configured to receive the ultrasonic backscatter or a separate interrogator. The ultrasonic transducers on the implanted medical device receives the ultrasonic waves from an external transducer and converts energy from the ultrasonic waves into electrical energy that powers the implanted medical device.

Electrical current flows through the ultrasonic transducer, and the electrical current can be modulated to encode the information related to the splenic nerve activity and/or blood pressure. For example, the implanted medical device can include an integrated circuit electrically connected to the ultrasonic transducer and the electrodes configured to detect the splenic nerve activity or the pressure sensor. The integrated circuit can include a modulation circuit, which modulates the electrical current to encode the information related to the splenic nerve activity and/or detected blood pressure. Since the ultrasonic backscatter is affected by the electrical current flowing through the ultrasonic transducer, the ultrasonic backscatter emitted by the ultrasonic transducer encodes the splenic nerve activity information and/or the blood pressure information encoded into the modulated electrical current.

Deviation in the electrical signal detected by the implanted medical device indicates a change in the blood pressure. For example, an increase in voltage potential of the splenic nerve over a period of time indicates increased blood pressure and/or hypertension. That is, an increase in amplitude of the measured cyclic voltage envelope of splenic nerve activity can indicate the increase in blood pressure and/or hypertension. From the deviation of a baseline signal of splenic nerve activity, an onset, offset, and a magnitude of a blood pressure change can be determined.

The ultrasonic backscatter emitted by the implanted medical device can be received by an external device (e.g., an interrogator), and the information encoded in the ultrasonic backscatter can be analyzed to monitor the blood pressure, blood pressure change, or hypertension.

A change in blood pressure can indicate that a therapy, such as an anti-hypertension therapy, should be administered to the subject. Accordingly, in some embodiments, a hypertension therapy is administered to the subject in response to a change in blood pressure. In some embodiments, a drug therapy is administered to the subject in response to a change in the blood pressure. In some embodiments, the therapy is an electrical stimulation of a nerve, such as the vagus nerve, the splenic nerve, the celiac ganglion, the sub-diaphragmatic vagus nerve, a splanchnic nerve, and/or a superior mesenteric nerve.

Implanted Medical Device

The implanted medical device includes two or more electrodes that are configured to be in electrical communication with the splenic nerve. In some embodiments, the implanted medical device includes a body, which contains one or more ultrasonic transducers and an integrated circuit that operates the device. The ultrasonic transducer receives ultrasonic waves, and converts the received ultrasonic waves into an electrical energy that powers the device. The body of the device can include or be connected to two or more electrodes or a sensor, which are in electric communication with the ultrasonic transducer (e.g., through the integrated circuit). In some embodiments, an electric current that flows through the ultrasonic transducer can be modulated to encode information in ultrasonic backscatter waves emitted by the ultrasonic transducer. The information encoded in the ultrasonic backscatter waves may include, for example, data related to a physiological condition detected by the sensor (such as temperature, a pulse, and/or blood pressure), an electrophysiological signal detected by the electrodes, a status of the device (for example, a status confirming the device is receiving signals encoded in ultrasonic waves, confirming operation of the integrated circuit, or confirming that the device is being powered), or information related to an electrical pulse emitted by the implantable device.

In some embodiments, the implantable device comprises a splenic nerve attachment member, such as a clip, attached to the body that is sized and configured to attach the device to the splenic nerve or splenic nerve artery. The splenic nerve attachment member is further sized and configured to position the two or more electrodes in electrical communication with the splenic nerve. In some embodiments, the splenic nerve attachment member is a clip configured to at least partially surround the splenic nerve and position the two or more electrodes in electrical communication with the splenic nerve.

Body of the Implantable Device

The body of the implantable device includes one or more ultrasonic transducers, and a sensor and/or an electrode pair. The electrode pair can be configured to detect an electrophysiological signal from or emit an electrical pulse. Exemplary implantable devices that can detect an electrophysiological signal and encode information related to the detected electrophysiological signal are described in WO 2018/009910 A2. Exemplary implantable devices that can be operated using ultrasonic waves to emit an electrical pulse are described in WO 2018/009912 A2. The sensor may be, for example, sensor the can detect or measure a physiological condition (such as temperature sensor, an oxygen sensor, a pH sensor, a strain sensor, a pressure sensor, an impedance sensor, or a sensor that can detect a concentration of an analyte). Exemplary implantable devices that are powered by ultrasonic waves and can emit an ultrasonic backscatter encoding a detected physiological condition are described in WO 2018/009905 A2 and WO 2018/009911 A2. In some embodiments, the implantable device comprises both a sensor and an electrode pair. In some embodiments, an integrated circuit is included in the implantable device, which can electrically connect and communicate between the electrodes or sensor and the ultrasonic transducer. The integrated circuit can include a modulation circuit, which modulates an electrical current flowing through the one or more ultrasonic transducers to encode data in the electrical current. The modulated electrical current affects ultrasonic backscatter waves emitted by the ultrasonic transducer, and the ultrasonic backscatter waves encode the data.

FIG. 1 shows a side view of an exemplary implantable device body with an ultrasonic transducer 102 and an integrated circuit 104. In the illustrated embodiment, the integrated circuit 104 includes a power circuit that includes a capacitor 106. The capacitor can temporarily store electrical energy converted from ultrasonic energy by the ultrasonic transducer, and can be operated by the integrated circuit 104 to store or release energy. The ultrasonic transducer 102, integrated circuit 104, and the capacitor 106 are mounted on a backplate 108, which may be a printed circuit board. The base 108 is set in a housing, which includes a bottom surface 110 and sidewalls 112a and 112b. The housing can further include a top (not shown) that seals the body components in the housing. The bottom surface 110 may include one or more feedthroughs 114a, 114b, and 114c that electrically connect the backplate and/or integrated circuit to one or more electrodes. The one or more electrodes may be located, for example, underneath the bottom surface 110 of the housing, or may be located on a clip as described herein. In this configuration, the electrodes can be in electrical communication with the nerve, and the components of the body are positioned above the nerve when the implantable device is implanted and attached to the nerve, for example using the clip as discussed herein. The ultrasonic transducer 102 is electrically connected to the integrated circuit 104, and the integrated circuit 104 is electrically connected to the electrodes via the feedthroughs, thereby electrically connecting the ultrasonic transducer 102 to the electrodes.

Figure 2:
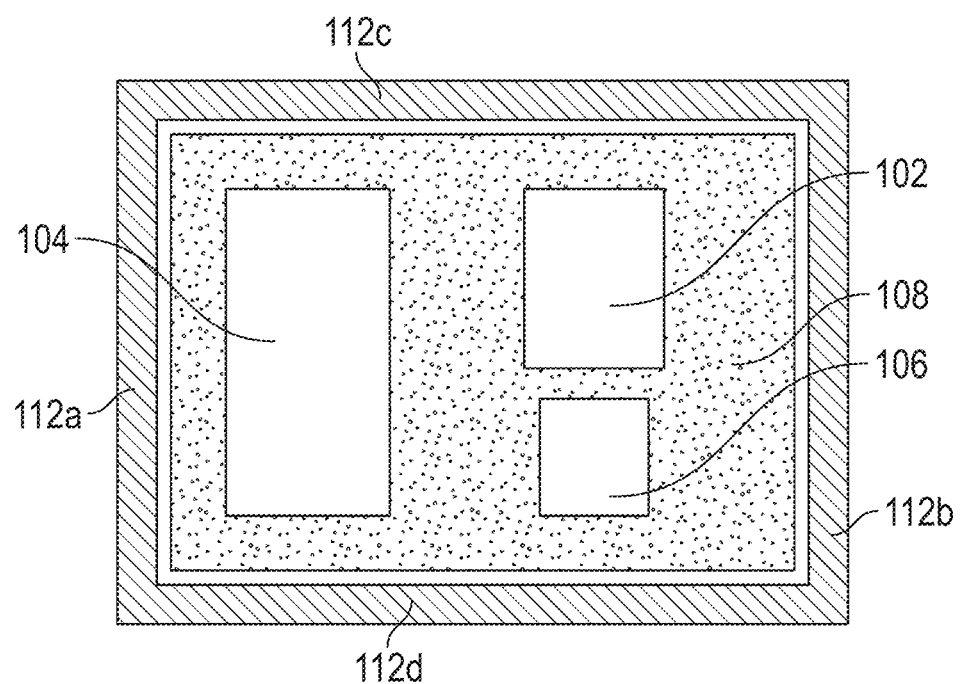
FIG. 2 shows a top view of a body of an implantable device, including an ultrasonic transducer, an integrated circuit, and a capacitor.

FIG. 2 illustrates a top view of the body similar to the one shown in FIG. 1, again without the top of the housing. The housing is shown with four sidewalls 112a, 112b, 112c, and 112d, although it is understood that the housing can be of any suitable shape (e.g., with three, four, five, six or more sidewalls, or with a single curved sidewall in a round or oval shape).

Figure 3:
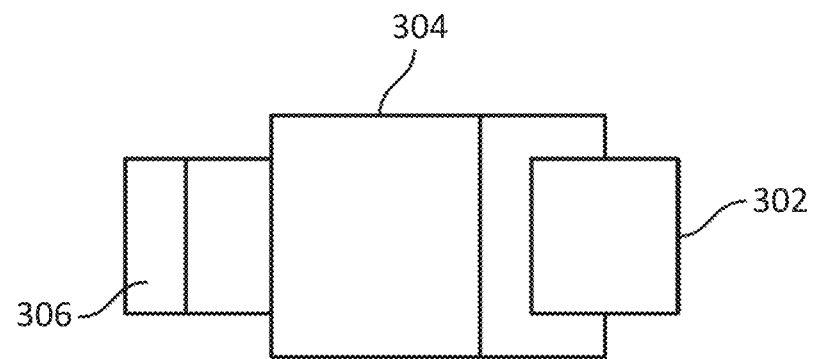
FIG. 3 shows an exemplary implantable device that includes an ultrasonic transducer, an integrated circuit and a sensor, which can be configured to measure a physiological condition.

FIG. 3 illustrates a schematic of an exemplary implantable device with an ultrasonic transducer 302, and integrated circuit 304, and a sensor 306 (such as sensor that can detect a temperature, pressure, strain, analyte concentration, oxygen, or pH). The ultrasonic transducer 302 is electrically connected to the integrated circuit 304, which his electrically connected to the sensor 306. Although the illustrated embodiment is shown with an integrated circuit, it is also conceived that the sensor can be directly connected to the ultrasonic transducer. Further, as discussed herein, one or more sensor can be included on an implantable device further having electrodes configured to detect and/or emit an electrical pulse.

The ultrasonic transducer is configured to receive ultrasonic waves and convert energy from the ultrasonic waves into an electrical energy. The electrical energy is transmitted to the integrated circuit to power the device. The implantable device can also operate to receive or transmit information through ultrasonic waves. Ultrasonic waves received by the implantable device (for example, those transmitted by the interrogator) can encode instructions for operating the implantable device. The instructions may include, for example, a trigger signal that instructs the implantable device to emit an electrical pulse through the electrodes. The trigger signal may include, for example, information relating to when the electrical pulse should be emitted, a pulse frequency, a pulse power or voltage, a pulse shape, and/or a pulse duration The implantable device can also operate to transmit information, which can be received by the interrogator. The ultrasonic transducer(s) on the implantable device receive ultrasonic waves and emit an ultrasonic backscatter, which can encode information transmitted by the implantable device. Current flows through the ultrasonic transducer, which can be modulated to encode the information. The current may be modulated directly, for example by passing the current through a sensor that modulates the current, or indirectly, for example by modulating the current using a modulation circuit based on a detected physiological condition or an electrophysiological pulse. In some embodiments, the information encoded in the ultrasonic waves includes information unrelated to a detected physiological condition or electrophysiological pules detected by the implantable device. For example, the information can include information related to the status of the implantable device or a confirmation signal that confirms an electrical pulse was emitted, and optionally the power, frequency, voltage, duration, or other information related to an emitted electrical pulse.

In some embodiments, the body includes a housing, which can include a base, one or more sidewalls, and a top. The housing can enclose the one or more ultrasonic transducers and the integrated circuit. The hosing may be sealed closed (for example by soldering or laser welding) to prevent interstitial fluid from coming in contact with the ultrasonic transducer(s) and/or the integrated circuit. The electrodes that are configured to be in electrical communication with the nerve are not enclosed by the housing. The housing is preferably made from a bioinert material, such as a bioinert metal (e.g., steel or titanium) or a bioinert ceramic (e.g., titania or alumina). The housing (or the top of the housing) may be thin to allow ultrasonic waves to penetrate through the housing. In some embodiments, the thickness of the housing is about 100 micrometers ($\mu$m) or less in thickness, such as about 75 $\mu$m or less, about 50 $\mu$m or less, about 25 $\mu$m or less, or about 10 $\mu$m or less. In some embodiments, the thickness of the housing is about 5 $\mu$m to about 10 $\mu$m, about 10 $\mu$m to about 25 $\mu$m, about 25 $\mu$m to about 50 $\mu$m, about 50 $\mu$m to about 75 $\mu$m, or about 75 $\mu$m to about 100 $\mu$m in thickness.

In some embodiments, the body comprises a material, such as a polymer, within the housing. The material can fill empty space within the housing to reduce acoustic impedance mismatch between the tissue outside of the housing and within the housing. Accordingly, the body of the device is preferably void of air or vacuum.

The body of the implantable device is relatively small, which allows for comfortable and long-term implantation while limiting tissue inflammation that is often associated with implantable devices. In some embodiments, the longest dimension of the body of the device is about 5 mm or less, about 4 mm or less, about 3 mm or less, about 2 mm or less, about 1 mm or less, about 0.5 mm or less, about 0.3 mm or less, about 0.1 mm or less in length. In some embodiments, the longest dimension of the body of the device is about 0.05 mm or longer, about 0.1 mm or longer, about 0.3 mm or longer, about 0.5 mm or longer, about 1 mm or longer, about 2 mm or longer, or about 3 mm or longer in the longest dimension of the device. In some embodiments, the longest dimension of the body of the device is about 0.04 mm to about 5 mm in length, about 0.05 mm to about 4 mm in length, about 0.07 mm to about 3 mm in length, about 0.08 mm to about 3 mm in length, or about 1 mm to about 2 mm in length.

In some embodiments, the body of the implantable device has a volume of about 5 mm³ or less (such as about 4 mm³ or less, 3 mm³ or less, 2 mm³ or less, or 1 mm³ or less). In some embodiments, the body of the implantable device has a volume of about 0.5 mm³ to about 5 mm³, about 1 mm³ to about 5 mm³, about 2 mm³ to about 5 mm³, about 3 mm³ to about 5 mm³, or about 4 mm³ to about 5 mm³. The small size of the implantable device allows for laparoscopic implantation of the device, thereby minimizing tissue damage when implanting the device.

The implantable device includes one or more ultrasonic transducers, such as one, two, or three or more ultrasonic transducers. In some embodiments, the implantable device includes a first ultrasonic transducer having a first polarization axis and a second ultrasonic transducer having a second polarization axis, wherein the second ultrasonic transducer is positioned so that the second polarization axis is orthogonal to the first polarization axis, and wherein the first ultrasonic transducer and the second ultrasonic transducer are configured to receive ultrasonic waves that power the device and emit an ultrasonic backscatter. In some embodiments, the implantable medical device includes a first ultrasonic transducer having a first polarization axis, a second ultrasonic transducer having a second polarization axis, and a third ultrasonic transducer having a third polarization axis, wherein the second ultrasonic transducer is positioned so that the second polarization axis is orthogonal to the first polarization axis and the third polarization axis, wherein the third ultrasonic transducer is positioned so that the third polarization axis is orthogonal to the first polarization and the second polarization axis, and wherein the first ultrasonic transducer and the second ultrasonic transducer are configured to receive ultrasonic waves that power the device and emit an ultrasonic backscatter. An implantable device with one, two, or three or more ultrasonic transducers may further include a sensor or two or more electrodes configured to be in electrical communication with a tissue, such as a nerve. Optionally, the implantable device further includes an integrated circuit.

Figure 4:
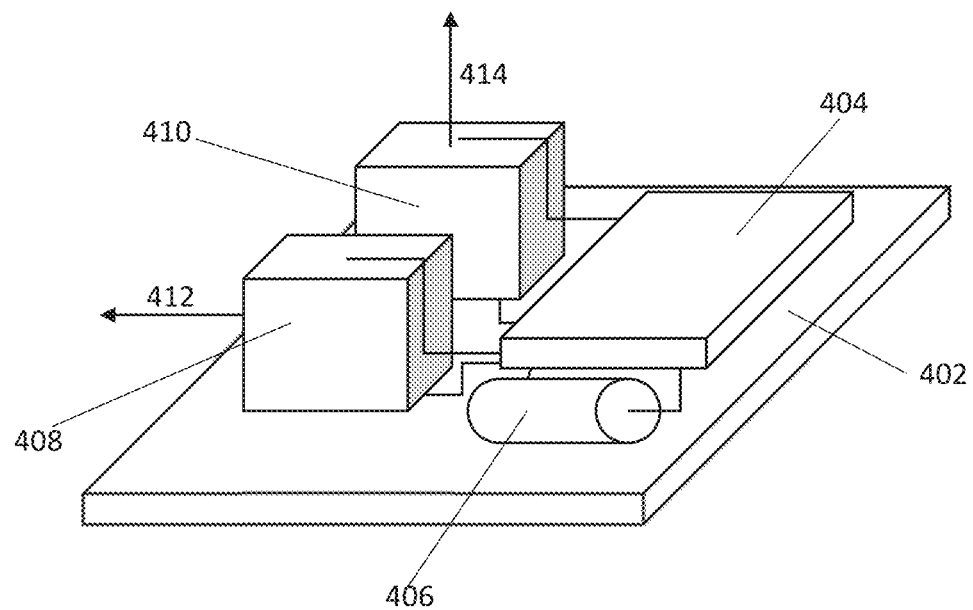
FIG. 4 shows a body of an implantable device that includes two orthogonally positioned ultrasonic transducers. The body further includes an integrated circuit that has a power circuit, which includes a capacitor.

FIG. 4 shows a body of a device that includes two orthogonally positioned ultrasonic transducers. The body includes a backplate 402, such as a printed circuit board, and an integrated circuit 404, which a power circuit that includes a capacitor 406. The body further includes a first ultrasonic transducer 408 electrically connected to the integrated circuit 404, and a second ultrasonic transducer 410 electrically connected to the integrated circuit 404. The first ultrasonic transducer 408 includes a first polarization axis 412, and the second ultrasonic transducer 410 includes a second polarization axis 414. The first ultrasonic transducer 408 and the second ultrasonic transducer are positioned such that the first polarization axis 412 is orthogonal to the second polarization axis 414. A housing (not shown) can enclose and optionally seal the body components. Further, the integrated circuit can be electrically coupled to a sensor or electrodes.

The ultrasonic transducer of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3GaSiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the bulk piezoelectric transducer is long and narrow, with an aspect ratio of about 3:1:1 or greater, and where the longest dimension is aligned to the direction of the ultrasonic backscatter waves (i.e., the polarization axis). In some embodiments, one dimension of the bulk piezoelectric transducer is equal to one half of the wavelength ($\lambda$) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 μm to about 1000 μm (such as about 40 μm to about 400 μm, about 100 μm to about 250 μm, about 250 μm to about 500 μm, or about 500 μm to about 1000 μm). In some embodiments, the height of the piezoelectric transducer is about 5 mm or less (such as about 4 mm or less, about 3 mm or less, about 2 mm or less, about 1 mm or less, about 500 μm or less, about 400 μm or less, 250 μm or less, about 100 μm or less, or about 40 μm or less). In some embodiments, the height of the piezoelectric transducer is about 20 μm or more (such as about 40 μm or more, about 100 μm or more, about 250 μm or more, about 400 μm or more, about 500 μm or more, about 1 mm or more, about 2 mm or more, about 3 mm or more, or about 4 mm or more) in length.

In some embodiments, the ultrasonic transducer has a length of about 5 mm or less such as about 4 mm or less, about 3 mm or less, about 2 mm or less, about 1 mm or less, about 500 μm or less, about 400 μm or less, 250 μm or less, about 100 μm or less, or about 40 μm or less) in the longest dimension. In some embodiments, the ultrasonic transducer has a length of about 20 μm or more (such as about 40 μm or more, about 100 μm or more, about 250 μm or more, about 400 μm or more, about 500 μm or more, about 1 mm or more, about 2 mm or more, about 3 mm or more, or about 4 mm or more) in the longest dimension.

The ultrasonic transducer is connected two electrodes to allow electrical communication with the integrated circuit. The first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene) (PEDOT), a conductive polymer (such as conductive PDMS or polyimide), or nickel. In some embodiments, the axis between the electrodes of the transducer is orthogonal to the motion of the transducer.

In some embodiments, the implantable device includes two or more electrodes in electrical communication with the splenic nerve. The implantable device can include, for example, a splenic nerve attachment member as described herein to position and retain the electrodes in electrical communication with the splenic nerve. In some embodiments, one or more electrical pulses emitted by the implantable device stimulate splenic nerve activity. In some embodiments, one or more electrical pulses emitted by the implantable device block splenic nerve activity.

The implantable device comprises a plurality of electrodes. In some embodiments, the electrodes are paired. Electrode pairs can be formed from two electrodes; thus, an implantable device with three electrodes can have three electrode pairs. The splenic nerve activity can be detected between the electrodes in the electrode pairs, or the splenic nerve can be stimulated using any of the electrode pairs. In some embodiments, the implantable device comprises 1, 2, 3, 4, 5, 6, 7, 8, 9, 10 or more, or 15 or more electrode pairs. In some embodiments, the implantable device comprises 2, 3, 5, 6, 7, 8, 9, 10 or more electrodes. In some embodiments, the implantable device includes a multiplexer, which can select the electrodes in the electrode pair to emit the electrical pulse or the electrode pair that detects splenic nerve activity.

Two or more electrodes that are electrically connected to the splenic nerve need not be linearly disposed along the nerve. For example, the electrodes may engage a nerve or other tissue along a transverse axis relative to the nerve, which can emit an electrical pulse in the transverse direction. Two or more electrodes can engage the splenic nerve along the transverse axis at any angle, such as directly opposite (i.e., 180°), or less than 180° (such as about 170° or less, about 160° or less, about 150° or less, about 140° or less, about 130° or less, about 120° or less, about 110° or less, about 100° or less, about 90° or less, about 80° or less, about 70° or less, about 60° or less, about 50° or less, about 40° or less, or about 30° or less).

In some embodiments, the electrodes in an electrode pair are separated by about 5 mm or less (such as about 4 mm or less, about 3 mm or less, about 2 mm or less, about 1.5 mm or less, about 1 mm or less, or about 0.5 mm or less). In some embodiments, the electrodes in the electrode pair are separated by about 0.5 mm or more (such as about 1 mm or more, about 1.5 mm or more, about 2 mm or more, about 3 mm or more, or about 4 or more. In some embodiments, the electrodes are separated by about 0.5 mm to about 1 mm, about 1 mm to about 1.5 mm, about 1.5 mm to about 2 mm, about 2 mm to about 3 mm, about 3 mm to about 4 mm, or about 4 mm to about 5 mm.

The electrodes are electrically coupled to the integrated circuit in the body of the implantable device. In some embodiments, the electrodes are positioned or terminate below the body, for example on a face of the base of the body housing opposite the body components (e.g., ultrasonic transducer, integrated circuit, etc.). In some embodiments, the electrodes terminate along a leg of a clip, as detailed herein. In some embodiments, one or more electrodes are exposed along at least a portion of the length of one of the legs.

The electrodes may be electrically coupled to the integrated circuit through one or more feedthroughs in the base of the housing. The feedthroughs may be, for example, a metal (such as a metal comprising silver, copper, gold, platinum, platinum-black, or nickel) sapphire, or a conductive ceramic (for example indium tin oxide (ITO)). The electrodes may be connected to the feedthrough using any suitable means, such as soldering, laser welding, or crimping the feedthrough to the electrodes.

In some embodiments, the implantable device includes one or more sensors. The sensors are configured to detect a physiological condition, such as temperature, oxygen concentration, pH, an analyte (such as glucose), strain, or pressure. Variation in the physiological condition modulates impedance, which in turn modulates current flowing ultrasonic transducer on the implantable device. As explained above, this produces ultrasonic backscatter detected by the interrogator; changes in the ultrasonic backscatter waves reflect information about the physiological condition. In some embodiments, the system is configured to detect changes in the physiological system. In some embodiments, the system is configured detect a value or an approximate value of the physiological condition, for example by calibrating the ultrasonic backscatter to known values. The implantable device may comprise one or more (such as 2, 3, 4, 5 or more) sensors, which may detect the same physiological condition or different physiological conditions. In some embodiments, the implantable device comprises 10, 9, 8, 7, 6 or 5 or fewer sensors). For example, in some embodiments, the implantable device comprises a first sensor configured to detect temperature and a second sensor configured to detect oxygen. Changes in both physiological conditions can be encoded in the ultrasonic backscatter waves, which can be deciphered by an external computing system.

The integrated circuit communicates between the ultrasonic transducer and the sensor and/or electrodes. For example, the ultrasonic transducer can receive information encoded in ultrasonic waves and generate an electrical current that encodes the information, which is transmitted to the integrated circuit. The information encoded in the electrical current can include instructions to operate the electrodes and/or sensor, and the integrated circuit can operate the electrodes and/or sensor in accordance with the instructions. The integrated circuit can also receive signals from the sensor and/or electrodes, and can modulate the electrical current flowing through the ultrasonic transducer to encode information related to the signals received from the sensor and electrodes.

In some embodiments, the implantable device emits ultrasonic backscatter that encodes information. The ultrasonic backscatter can be received by the interrogator, for example, and deciphered to determine the encoded information. The information can be encoded using a modulation circuit within the integrated circuit of the implantable device. The modulation circuit can modulate the current flowing through the ultrasonic transducer to encode the information (e.g., information related to a detected electrophysiological pulse or a physiological condition, or information related to the device status). The modulated current flows through the ultrasonic transducer to modulate the ultrasonic backscatter, thereby encoding the information in the ultrasonic backscatter waves. The modulation circuit includes one or more switches, such as an on/off switch or a field-effect transistor (FET). An exemplary FET that can be used with some embodiments of the implantable device is a metal-oxide-semiconductor field-effect transistor (MOSFET). The modulation circuit can alter the impedance of a current flowing through the ultrasonic transducer, and variation in current flowing through the transducer encodes the electrophysiological signal. In some embodiments, information encoded in the ultrasonic backscatter includes a unique identifier for the implantable device. This can be useful, for example, to ensure the interrogator is in communication with the correct implantable device when a plurality of implantable devices is implanted in the subject. In some embodiments, the information encoded in the ultrasonic backscatter includes a verification signal that verifies an electrical pulse was emitted by the implantable device. In some embodiments, the information encoded in the ultrasonic backscatter includes an amount of energy stored or a voltage in the energy storage circuit (or one or more capacitors in the energy storage circuit). In some embodiments, the information encoded in the ultrasonic backscatter includes a detected impedance. Changes in the impedance measurement can identify scarring tissue or degradation of the electrodes over time.

In some embodiments, the modulation circuit is operated by a digital circuit or a mixed-signal integrated circuit, which can actively encode the information in a digitized or analog signal. The digital circuit or mixed-signal integrated circuit may include a memory and one or more circuit blocks, systems, or processors for operating the implantable device. These systems can include, for example, an onboard microcontroller or processor, a finite state machine implementation, or digital circuits capable of executing one or more programs stored on the implant or provided via ultrasonic communication between interrogator and implantable device. In some embodiments, the digital circuit or a mixed-signal integrated circuit includes an analog-to-digital converter (ADC), which can convert analog signal encoded in the ultrasonic waves emitted from the interrogator so that the signal can be processed by the digital circuit or the mixed-signal integrated circuit. The digital circuit or mixed-signal integrated circuit can also operate the power circuit, for example to generate the electrical pulse to stimulate the tissue. In some embodiments, the digital circuit or the mixed-signal integrated circuit receives the trigger signal encoded in the ultrasonic waves transmitted by the interrogator, and operates the power circuit to discharge the electrical pulse in response to the trigger signal.

In some embodiments, the integrated circuit includes a power circuit, which can include an energy storage circuit. The implantable device powered by ultrasonic waves is preferably batteryless, although the energy storage circuit can include one or more capacitors to temporarily store electrical energy. Energy from the ultrasonic waves is converted into a current by the ultrasonic transducer, and can be stored in the energy storage circuit. The energy can be used to operate the implantable device, such as providing power to the digital circuit, the modulation circuit, or one or more amplifiers, or can be used to generate the electrical pulse used to stimulate the tissue. In some embodiments, the power circuit further includes, for example, a rectifier and/or a charge pump.

In some embodiments, the integrated includes a driver circuit, which provides current to one or more sensors and/or electrodes. Optionally, the driver circuit is operated by the digital circuit or mixed-signal integrated circuit if present. In some embodiments, one or more amplifiers are disposed between the driver circuit and the digital circuit. In some embodiments, the integrated includes a front end circuit (such as a CMOS front end), which can receive a signal from the sensor/and or electrodes. The signal received by the front end circuit can be relayed to the digital circuit.

Figure 12:
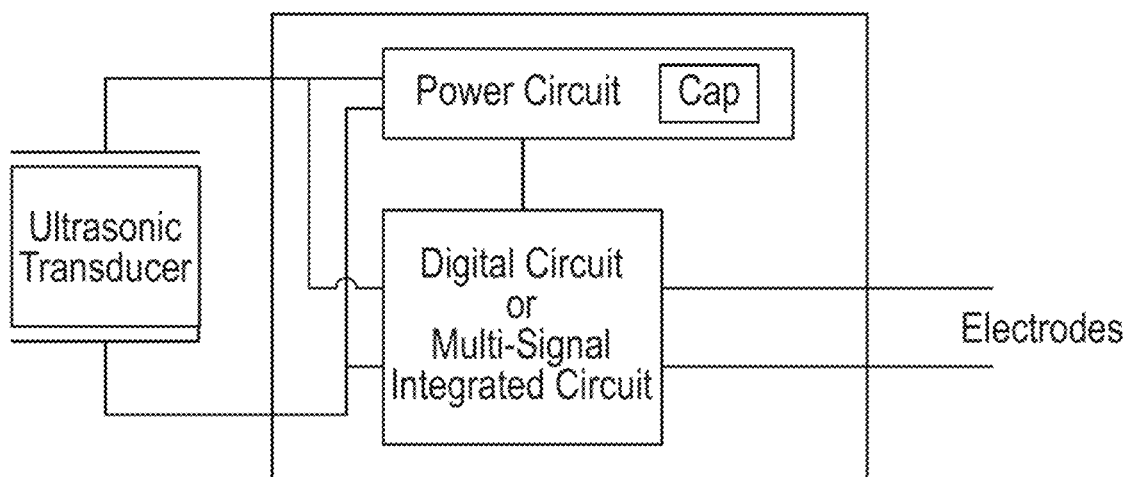
FIG. 12 shows a schematic of one embodiment of an implantable device showing the ultrasonic transducer and electrodes electrically connected to an integrated circuit. The integrated circuit includes a power circuit, which includes a capacitor that can store electrical energy from the ultrasonic transducer. The integrated circuit further includes a digital circuit or a multi-signal integrated circuit (with the digital circuit or the multi-signal integrated circuit including the modulation circuit), which can operate the power circuit and modulate an electrical current flowing through the ultrasonic transducer to encode information.

FIG. 12 shows a schematic an embodiment of an implantable device that includes an integrated circuit and electrodes configured to emit an electrical pulse. The implantable device includes a ultrasonic transducer, a power circuit including an energy storage circuit (which can include one or more capacitors ("cap"), a digital circuit or multi-signal integrated circuit, and a pair of electrodes. The ultrasonic transducer is connected to the power circuit, which allows energy from the ultrasonic waves to be stored in the energy storage circuit. The power circuit is connected to the digital circuit or multi-signal integrated circuit so that the digital circuit or multi-signal integrated circuit can operate the power circuit. The digital circuit or multi-signal integrated circuit is also connected to the ultrasonic transducer. When a trigger signal is encoded in ultrasonic waves received by the ultrasonic transducer, the digital circuit or multi-signal integrated circuit can detect the trigger signal. The digital circuit or multi-signal integrated circuit can then operate the power circuit to release energy stored in the energy circuit, thereby emitting an electrical pulse using the electrodes. Optionally, the digital circuit or multi-signal integrated circuit can operate or include a modulation circuit, which can modulate the electrical current flowing through the ultrasonic transducer to encode information, such as information relating to operation of the implantable device or information related to an electrical pulse detected by the electrodes.

Splenic Nerve Attachment Member

In some embodiments, the implantable medical device includes a splenic nerve attachment member attached to the body, wherein the splenic nerve attachment member is sized and configured to attach the device to the splenic nerve or a splenic artery and position the two or more electrodes in electrical communication with the splenic nerve. In some embodiments, the splenic nerve attachment member is a clip attached to the body that is configured to at least partially surround a nerve to position the two or more electrodes in electrical communication with the splenic nerve. The splenic nerve may be attached to the splenic artery, and the splenic nerve attachment member can be configured to at least partially surround the splenic nerve and the splenic artery.

The splenic nerve attachment member holds the implantable device in place on the splenic nerve and/or splenic artery. In some embodiments, the splenic nerve attachment member allows for some rotational movement of the implantable device on the splenic nerve and/or splenic artery. In some embodiments, the splenic nerve attachment member grips the splenic nerve and/or splenic artery by exerting an inward pressure on the nerve and/or artery. The amount of inward pressure exerted by the splenic nerve attachment member can be determined based on the size and curvature of the splenic nerve attachment member, as well as by the spring constant of the splenic nerve attachment member components such as the clip legs. The inward pressure should be sufficient to hold the implantable device in place while the tissue heals after insertion, but not so high that the epineurium or vascular walls that contact the legs are damaged. In some embodiments, the inward pressure on the nerve or filamentous tissue is about 1 MPa or less (such as about 0.7 MPa or less, about 0.5 MPa or less, or about 0.3 MPa or less). In some embodiments, the inward pressure on the nerve or filamentous tissue is about 0.1 MPa to about 1 MPa (such as about 0.1 MPa to about 0.3 MPa, about 0.3 MPa to about 0.5 MPa, about 0.5 MPa to about 0.7 MPa, or about 0.7 MPa to about 1 MPa).

In some embodiments, the implantable medical device includes a body comprising an ultrasonic transducer configured to receive ultrasonic waves and convert energy from the ultrasonic waves into an electrical energy that powers the device; two or more electrodes in electrical communication with the ultrasonic transducer; and a splenic nerve attachment member attached to the body, wherein the splenic nerve attachment member is sized and configured to attach the device to the splenic nerve or splenic artery and position the two or more electrodes in electrical communication with the splenic nerve. In some embodiments, the splenic nerve attachment member comprises a clip that is configured to at least partially surround the splenic nerve or splenic artery.

The clip can include a plurality of flexible legs that extend below the body of the implantable device. In some embodiments, the legs are curved. For example, in some embodiments, the legs extend away from the body before curving toward the body as the legs extend below the body. The clip may include pairs of legs, with each leg in the pair extending away from the body in opposite directions. This configuration allows the legs to wrap around the splenic nerve and/or splenic artery (or at least partially wrap around the splenic nerve and/or splenic artery). The legs in the pair of legs can be connected by a crossbar, which allows the legs to be positioned in a staggered configuration, with one the legs in the pair being positioned closer to the body than the other leg. By staggering the legs at different distances from the body of the device, the legs can extend such that the ends of the legs extend past each other to completely surround the splenic nerve and/or splenic artery. In some embodiments, the legs in the pair of the legs and the crossbar are a single piece (e.g., co-extruded or a co-printed) of material, such as a metal, metal alloy, ceramic, silicon, or a non-polymeric material. The legs or the crossbar(s) of the device are connected to the body of the dive. If the implantable device includes two pairs of legs each connected by a crossbar, the crossbars may be attached to the body at opposite ends of the body. The lengths of the crossbars attached to the body can be along the same axis, which can be parallel to the axis of the splenic nerve and/or splenic artery.

In some embodiments, the legs or the crossbar(s) of the implantable device are connected to the body of the device through a flexible member, such as a hinge (for example, a spring hinge). The flexibility of the legs and flexible member allows the implantable device to be maneuvered in position on the nerve by flexing the legs of the clip, which can return to their default position to correctly position the electrodes of the device in electrical communication with the nerve.

Figure 5:
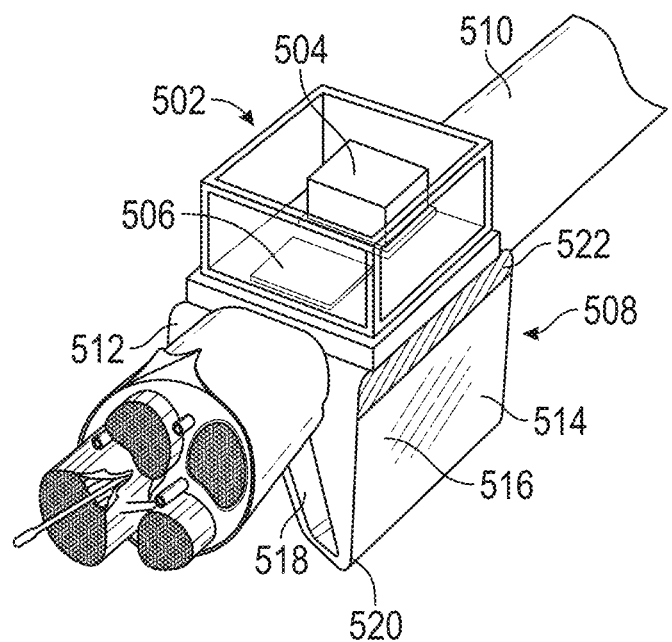
FIG. 5 shows an exemplary implantable device with a body attached to a clip. The body includes an ultrasonic transducer and an integrated circuit, which are electrically connected to two or more electrodes that are in electrical communication with a splenic nerve. The clip holds the body to the splenic nerve and the splenic artery, and further holds the electrodes in position to electrically stimulate or detect an electrophysiological pulse from a nerve.

FIG. 5 shows one example of an implantable device with a clip. The implantable device includes a body 502, which includes an ultrasonic transducer 504 and an integrated circuit 506. The ultrasonic transducer 504 can receive ultrasonic waves from an interrogator, and the ultrasonic transducer converts energy from the ultrasonic waves into an electrical energy that powers the device. The ultrasonic transducer 504 is electrically connected to the integrated circuit 506, which can encode information in an electric current that flows through the ultrasonic transducer 504. The ultrasonic transducer 504 emits an ultrasonic backscatter based on the received current, and the ultrasonic backscatter encodes the information that was encoded in the electric current.

The implantable device includes two or more electrodes that are in electric communication with the ultrasonic transducer 504, for example through the integrated circuit 506. In some configurations, the electrodes are configured to emit an electrical pulse to the nerve, for example by being operated by the integrated circuit 506. Optionally, splenic nerve activity can be detected by the electrodes and communicated to the integrated circuit 506, which can modulate an electric current flowing through the ultrasonic transducer 504 based on the detected splenic nerve activity. The body 502 of the implantable device is attached to a clip 508. The clip is configured to surround a nerve 510 and position the two or more electrodes in electrical communication with the never. In the embodiment illustrated in FIG. 5, the electrodes are positioned along the bottom of the body 502 in contact with the nerve 510. In some embodiments, the two or more electrodes are in physical contact with the nerve, although some movement of the implantable device may be allowed so long as the electrodes remain in electrical communication with the splenic nerve. The electrodes need not penetrate the epineurium of the splenic nerve.

The clip includes a first leg 512 and a second leg 514, which are positioned on opposite sides of the splenic nerve 510. The legs of the clip are optionally flexible so that the legs can be flexed outwardly to position the clip on the splenic nerve. When the legs are released, the legs spring inwardly to maintain the electrodes in electrical communication with the splenic nerve. The size and spacing of the legs are configured to engage with and attach to the splenic nerve and/or splenic artery. In embodiment illustrated in FIG. 5, leg 514 has a width approximately the same length as the body 502. The leg 514 includes a first segment 516 that extends from the body along the side of the nerve 510 to below the nerve 510, and a second segment 518 that extends from the bottom of the first portion toward the underside of the nerve 510. A flexible member 520 (such as a hinge, for example a spring hinge) joins the first segment 516 and the second segment 518, which can allow the second segment 518 to flex toward the first segment 516 when the implantable device is being positioned on the nerve. The end of second segment 518 can be released and the second segment 518 springs into position below the nerve 510. Optionally, a second flexible member 522 (which may be, for example, a hinge) attaches the leg 508 to the body 502. The second flexible member 522 allows the leg 514 to flex outwardly when positioning the implantable device on the nerve 510.

Figure 6:
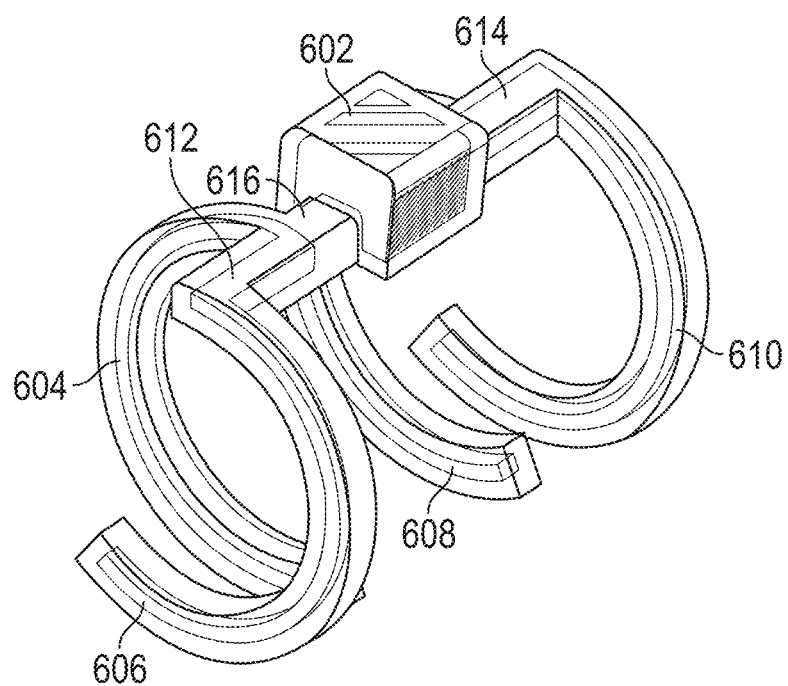
FIG. 6 shows another example of an implantable device that includes a body with a housing that encloses an ultrasonic transduce and an integrated circuit. The body is attached to a clip that includes legs configured to at least partially surround the splenic nerve and splenic artery, and position electrodes in electrical communication with the nerve.

FIG. 6 shows another example of an implantable device, which includes a body 602 and a clip configured to at least partially surround a nerve, comprising a plurality of flexible legs 604, 606, 608, and 610. The body 602 includes a housing, and contains an ultrasonic transducer configured to receive ultrasonic waves and convert energy from the ultrasonic waves into an electrical energy that powers the implantable device. The implantable device further includes a plurality of electrodes positioned on the bottom of the body housing. The electrodes are in electrical communication with the ultrasonic transducer, for example through an integrated circuit contained within the body 602 of the implantable device. When the clip is positioned on the nerve to at least partially surround the nerve, the electrodes are positioned to be in electrical communication with the splenic nerve.

The legs 604, 606, 608, and 610 of the implantable device extend below the body 602 and are curved, which allows the legs to wrap around the splenic nerve and/or splenic artery. The upper portions of the legs extend away from the body 602, and the legs curve back toward the body 602 as they extend below the body. The clip illustrated in FIG. 6 includes a first pair of legs, 604 and 606, and a second pair of legs 608 and 610. The paired legs extend away from the body in opposite directions. The upper portion of legs 604 and 606 are connected by crossbar 612, and the upper portion of legs 608 and 610 are connected by crossbar 614. Crossbar 612 is connected to the body 602 through flexible member 616, and crossbar 614 is connected to the body 602 through a second flexible member (not shown). The flexible member may be, for example, a hinge (such as a spring hinge). The crossbars are connected to opposite sides of the body 602, and the length of the crossbars are oriented in the same direction (i.e., parallel to the nerve).

The clip is designed to allow the legs of the clip to at least partially surround the splenic nerve and/or the splenic artery. In some embodiments, such as the clip of the device shown in FIG. 6, the inner surface of the legs form a cylindrical space through which the splenic nerve and/or splenic artery passes. In some embodiments, the legs of the device form a cylindrical space with a diameter of about 500 µm to about 8 mm (for example, about 500 µm to about 1 mm, about 1 mm to about 1.5 mm, about 1.5 mm to about 2.5 mm, about 2.5 mm to about 5 mm, or about 5 mm to about 8 mm). As the splenic nerve may be attached to the splenic artery with the implantable device in place, in some embodiments, the cylindrical space has a diameter of about 2 mm to about 8 mm (such as about 2 mm to about 3 mm, about 3 mm to about 4 mm, about 4 mm to about 5 mm, about 5 mm to about 6 mm, about 6 mm to about 7 mm, about 7 mm to about 8 mm).

The legs of device may also be sized to optimally engage the splenic nerve, and in some embodiments may have a width (including any coating material on the legs) of about 200 µm to about 2 mm (such as about 200 µm to about 400 µm, about 400 µm to about 1 mm, about 1 mm to about 1.5 mm, or about 1.5 mm to about 2 mm). In some embodiments, the legs of the clip are sized to optimally engage the splenic nerve and the splenic artery, and may have a width (including any coating material on the legs) of about 500 µm or about 2 mm (such as about 500 µm to about 1 mm, about 1 mm to about 1.5 mm, or about 1.5 mm to about 2 mm).

Figure 7:
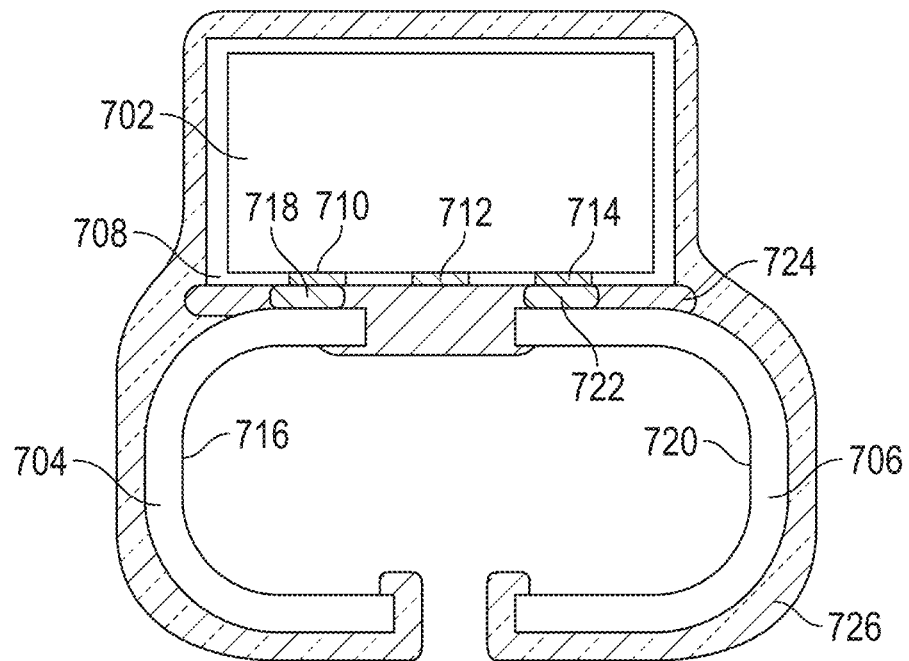
FIG. 7 shows a side view of another embodiment of an implantable device with a body attached to a clip having a plurality of legs. The clip is attached to the body underneath the bottom surface of the body. The legs are coated with an coating on the outer portion of the legs, but are uncoated on the inner portion of the legs. The electrodes are uncoated and positioned on the inner portion of the legs.

FIG. 7 shows a side view of another embodiment of an implantable device with a clip. Similar to the implantable device shown in FIG. 6, the implantable device includes a body 702 with a clip configured to at least partially surround the splenic nerve. The clip includes legs 704 and 706, although it is contemplated that the device optionally includes additional legs and/or one or more crossbars. The bottom surface 708 of the housing 702 includes feedthroughs 710, 712, and 714. The feedthroughs electrically connect the integrated circuit in the body of the device to the electrodes. For example, feedthrough 710 is electrically connected to electrode 716 through connection 718, and feedthrough 714 is electrically connected to electrode 720 through connection 722. The connections 718 and 722 may be, for example, a solder, a weld, or a crimp connecting the feedthrough to the electrode. Electrode 716 is positioned on the internal surface of leg 704, and electrode 720 is positioned on the internal surface of leg 706. The electrodes are in electrical communication with the ultrasonic transducer, for example through an integrated circuit contained within the body 702 of the implantable device via the feedthroughs. When the clip is positioned on the nerve to at least partially surround the nerve, the electrodes are positioned to be in electrical communication with the nerve. Leg 704 and leg 706 are secured to the body 702 of the device through a sealing material 724. The sealing material can also seal the connections 718 and 722. In some embodiments, the sealing material is an epoxy or a polymer (such as silicone or a urethane polymer).

The legs of the implantable device can comprise a metal, metal alloy, ceramic, silicon, or a non-polymeric material. In some embodiments, one or more electrodes are positioned on an inner surface of the legs. The legs are flexible, and preferably sprung such that the legs can be positioned around the nerve and/or filamentous tissue. In some embodiments, the legs or a portion of the legs are coated with an elastomeric coating or a non-elastomeric coating, which is preferably bioinert, such as polydimethylsioloxane (PDMS), a silicone, a urethane polymer, a poly(p-xylylene)polymer (such as a poly(p-xylylene) polymer sold under the tradename PARYLENE®), or a polyimide. In some embodiments, the implantable device includes one or more electrodes on the inner surface of the legs. In some embodiments, one or more of the electrodes on the inner surface of the legs are not coated with the elastomeric coating or the non-elastomeric polymer coating, although may be coated with a conductive material (e.g., electroplated with a PEDOT polymer or a metal to improve electrical characteristics of the electrode). Accordingly, in some embodiments, only the outer surface of the legs is coated with the coating. Optionally, the coating further coats the housing of the body. Referring to FIG. 7 by way of example, the outer surface of legs 704 and 706 are coated with the coating 726. However, because electrodes 716 and 720 are on the inner surface of legs 704 and 706, the coating 726 does not coat the inner surface of the legs.

Figures 8A, 8B:
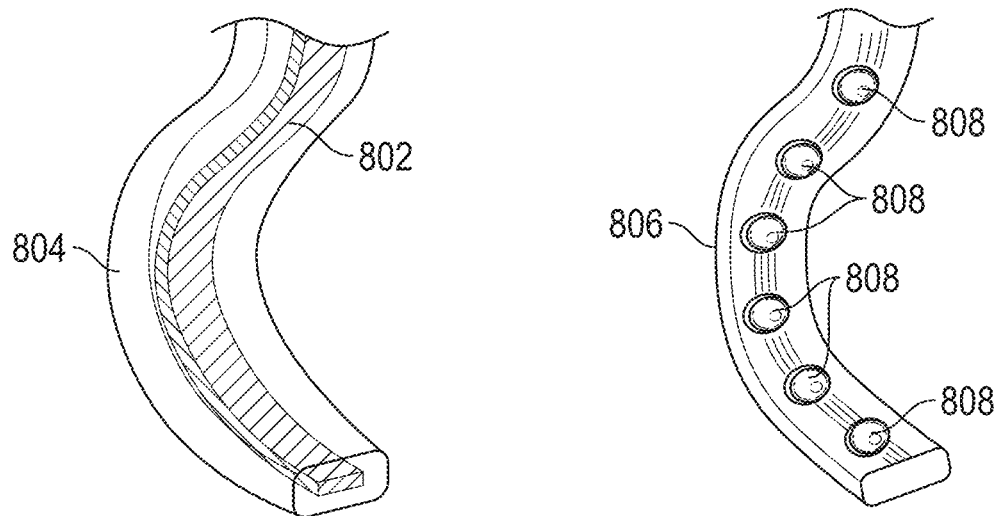
FIG. 8A and FIG. 8B illustrate two exemplary configurations of legs having electrodes positioned on the legs.

FIG. 8A and FIG. 8B illustrate two exemplary configurations with electrodes on the legs of the clips. As shown in FIG. 8A, the leg 802 is coated with a coating 804, such as an elastomeric polymer or a non-elastomeric polymer. A single electrode is exposed through the elastomeric or non-elastomeric polymer, which can be in electrical communication with a nerve. FIG. 8B illustrates a leg 806 with a plurality of electrodes 808 along the inner surface of the leg. In the embodiment illustrated in FIG. 8B, the leg 806 is not coated with an elastomeric polymer or a non-elastomeric polymer. However, the leg 806 could be optionally coated with the polymer on the outer surface of the leg 806.

Figure 9A:
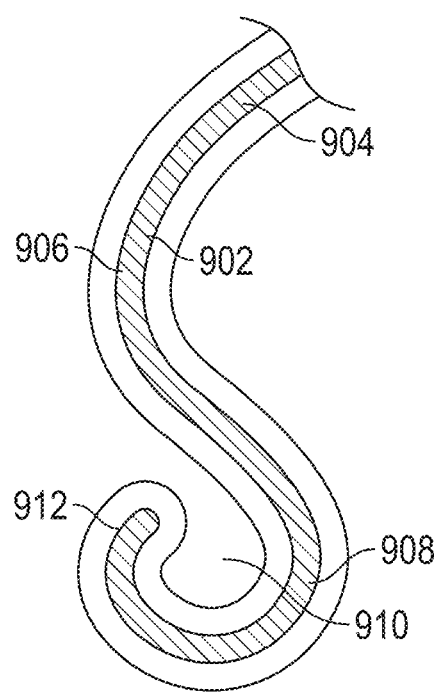
FIG. 9A shows one embodiment of a leg with a hook at the terminus of the leg.
Figure 9B:
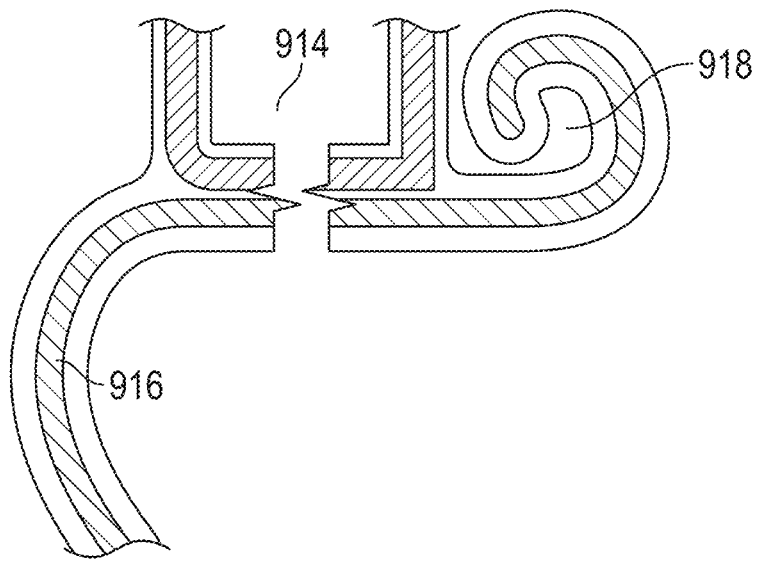
FIG. 9B shows an embodiment of an implantable device with a hook proximal to the body of the device. The hook on the device in FIG. 9B is connected to a leg on the opposite side of the body, and maneuvering the hook allows the leg to be flexed outwardly.

In some embodiments, the legs comprise one or more hooks or loops, which may be positioned proximal to the terminus of the legs or may be positioned along the length of the leg. The hook or loop can be used to help manipulate, flex, or position the clip into position. In some embodiments, the hook or loop curves toward the body of the implantable device, and in some embodiments the hook or loop curves away from the body of the implantable device. FIG. 9A shows one embodiment of a leg with a hook at the terminus of the leg. The leg 902 connects to the body of the device at the starting end 904, and extends below and away from the body. The leg 902 curves inwardly at 906 before curving outwardly at 908 to form a hook 910 at the terminus 912 of the leg. In some embodiments, the clip includes a hook or a loop configured to manipulate a leg of the clip, for example as shown in FIG. 9B. The implantable device includes a body 914 attached to a leg 916 that extends below and away from the body 914. The leg 916 is connected to a hook 918 opposite the body 914, for example through a continuous member (for example, metal or non-elastomeric plastic). The hook 918 and the leg 916 may be, for example, co-extruded or co-printed to form the continuous member. When hook 918 is pushed downwardly, the leg 916 is pushed outwardly. Through this mechanism, the implantable device can be properly positioned on a nerve, for example through laparoscopic implantation.

The two or more electrodes of the implantable device are positioned by the clip to be in electrical communication with the nerve. In some embodiments, the two or more electrodes directly contact the nerve. In some embodiments, the two or more electrodes are positioned within about 2 mm (within about 1.8 mm, within about 1.6 mm, within about 1.4 mm, within about 1.2 mm, within about 1.0 mm, within about 0.8 mm, within about 0.6 mm, within about mm, or within about 0.2 mm of the nerve. The electrodes may be disposed on the bottom of the body or on one or more clip legs. Legs that extend below the body secure the body to the nerve, and by positioning the electrodes on the bottom of the body, the electrodes are positioned in electrical communication with the nerve.

Interrogator

The interrogator can wirelessly communicate with one or more implantable devices using ultrasonic waves, which are used to power and/or operate the implantable device. For example, the interrogator can transmit ultrasonic waves that encode instructions for operating the device, such as a trigger signal that instructs the implantable device to emit an electrical pulse. The interrogator can further receive ultrasonic backscatter from the implantable device, which encodes information transmitted by the implantable device. The information may include, for example, information related to a detected electrophysiological pulse, an electrical pulse emitted by the implantable device, and/or a measured physiological condition. The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device. In some embodiments, the transducers in the array can have regular spacing, irregular spacing, or be sparsely placed. In some embodiments the array is flexible. In some embodiments the array is planar, and in some embodiments the array is non-planar.

Figure 10:
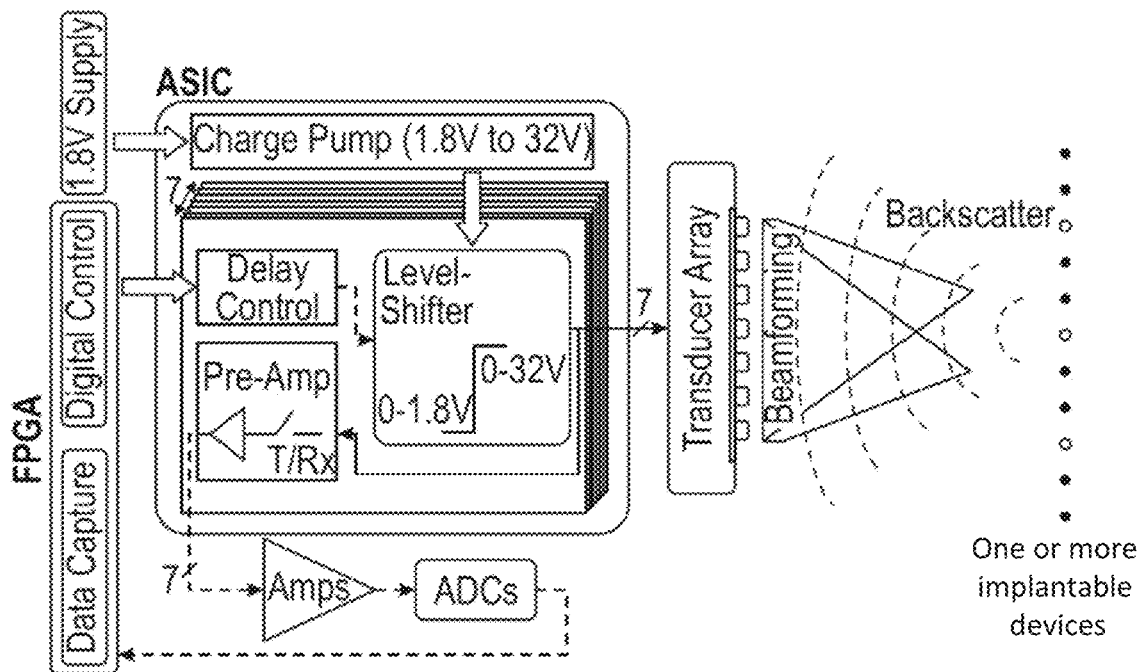
FIG. 10 shows an exemplary interrogator that can be used with the implantable device.

An exemplary interrogator is shown in FIG. 10. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, or fewer, 15 or fewer, 10 or fewer, 7 or fewer or 5 or fewer transducers. The transducer array can be, for example a chip comprising 50 or more ultrasonic transducer pixels.

The interrogator shown in FIG. 10 illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an application specific integrated circuit (ASIC), which includes a channel for each transducer in the transducer array. In some embodiments, the channel includes a switch (indicated in FIG. 10 by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit.

In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to 'stream' out this data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 10) to convert a first voltage supplied to the ASIC to a higher second voltage, which is applied to the channel. The channels can be controlled by a controller, such as a digital controller, which operates the delay control.

In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier, or a time-gain-controlled variable-gain-amplifier which compensates for tissue loss, and/or a band pass filter is included in the receiving circuit. The ASIC can draw power from a power supply, such as a battery (which is preferred for a wearable embodiment of the interrogator). In the embodiment illustrated in FIG. 10, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

In some embodiments, the interrogator is implantable. In some embodiments, the interrogator is external (i.e., not implanted). By way of example, the external interrogator can be a wearable, which may be fixed to the body by a strap or adhesive. In another example, the external interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator.

The specific design of the transducer array depends on the desired penetration depth, aperture size, and size of the individual transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and λ is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., *Beamforming Approaches for Untethered, Ultrasonic Neural Dust Motes for Cortical Recording: a Simulation Study*, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Optionally, the interrogator is controlled using a separate computer system, such as a mobile device (e.g., a smartphone or a table). The computer system can wirelessly communicate to the interrogator, for example through a network connection, a radiofrequency (RF) connection, or Bluetooth. The computer system may, for example, turn on or off the interrogator or analyze information encoded in ultrasonic waves received by the interrogator.

Communication Between an Implantable Device and an Interrogator

The implantable device and the interrogator wirelessly communicate with each other using ultrasonic waves. The implantable device receives ultrasonic waves from the interrogator through one or more ultrasonic transducers on the implantable device, and the ultrasonic waves can encode instructions for operating the implantable device. Vibrations of the ultrasonic transducer(s) on the implantable device generate a voltage across the electric terminals of the transducer, and current flows through the device, including the integrated circuit. The current can be used to charge an energy storage circuit, which can store energy to be used to emit an electrical pulse, for example after receiving a trigger signal. The trigger signal can be transmitted from the interrogator to the implantable device, signaling that an electrical pulse should be emitted. In some embodiments, the trigger signal includes information regarding the electrical pulse to be emitted, such as frequency, amplitude, pulse length, or pulse shape (e.g., alternating current, direct current, or pulse pattern). A digital circuit can decipher the trigger signal and operate the electrodes and electrical storage circuit to emit the pulse.

In some embodiments, ultrasonic backscatter is emitted from the implantable device, which can encode information relating to the implantable device, the electrical pulse emitted by the implantable device, an electrophysiological pulse detected by the implantable device, or a detected physiological condition. For example, the ultrasonic backscatter can encode a verification signal, which verifies that electrical pulse was emitted. In some embodiments, an implantable device is configured to detect an electrophysiological signal, and information regarding the detected electrophysiological signal can be transmitted to the interrogator by the ultrasonic backscatter. To encode signals in the ultrasonic backscatter, current flowing through the ultrasonic transducer(s) of the implantable device is modulated as a function of the encoded information, such as a detected electrophysiological signal or measured physiological condition. In some embodiments, modulation of the current can be an analog signal, which may be, for example, directly modulated by the detected splenic nerve activity. In some embodiments, modulation of the current encodes a digitized signal, which may be controlled by a digital circuit in the integrated circuit. The backscatter is received by an external ultrasonic transceiver (which may be the same or different from the external ultrasonic transceiver that transmitted the initial ultrasonic waves). The information from the electrophysiological signal can thus be encoded by changes in amplitude, frequency, or phase of the backscattered ultrasound waves.

Figure 11:
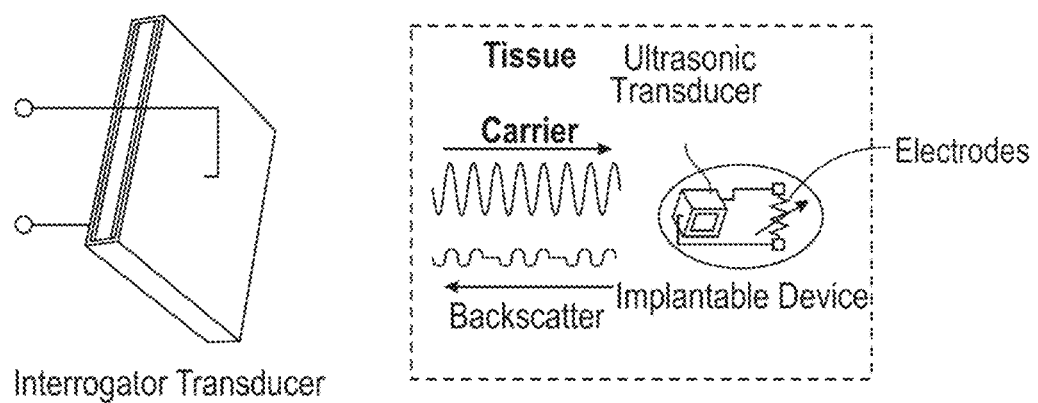
FIG. 11 shows an interrogator in communication with an implantable device. The interrogator can transmit ultrasonic waves, which can encode a trigger signal. The implantable device emits an ultrasonic backscatter, which can be modulated by the implantable device to encode information.

FIG. 11 shows an interrogator in communication with an implantable device. The external ultrasonic transceiver emits ultrasonic waves ("carrier waves"), which can pass through tissue. The carrier waves cause mechanical vibrations on the miniaturized ultrasonic transducer (e.g., a miniaturized bulk piezoelectric transducer, a PUMT, or a CMUT). A voltage across the ultrasonic transducer is generated, which imparts a current flowing through an integrated circuit on the implantable device. The current flowing through to the ultrasonic transducer causes the transducer on the implantable device to emit backscatter ultrasonic waves. In some embodiments, the integrated circuit modulates the current flowing through the ultrasonic transducer to encode information, and the resulting ultrasonic backscatter waves encode the information. The backscatter waves can be detected by the interrogator, and can be analyzed to interpret information encoded in the ultrasonic backscatter.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. In some embodiments, the pulses are square, rectangular, triangular, sawtooth, or sinusoidal. In some embodiments, the pulses output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period.

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which can encode information, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, the digitized data can include a unique identifier. The unique identifier can be useful, for example, in a system comprising a plurality of implantable devices and/or an implantable device comprising a plurality of electrode pairs. For example, the unique identifier can identify the implantable device of origin when from a plurality of implantable devices, for example when transmitting information from the implantable device (such as a verification signal). In some embodiments, an implantable device comprises a plurality of electrode pairs, which may simultaneously or alternatively emit an electrical pulse by a single implantable device. Different pairs of electrodes, for example, can be configured to emit an electrical pulse in different tissues (e.g., different nerves or different muscles) or in different regions of the same tissue. The digitized circuit can encode a unique identifier to identify and/or verify which electrode pairs emitted the electrical pulse.

In some embodiments, the digitized signal compresses the size of the analog signal. The decreased size of the digitized signal can allow for more efficient reporting of information encoded in the ultrasonic backscatter. By compressing the size of the transmitted information through digitization, potentially overlapping signals can be accurately transmitted.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

EXEMPLARY EMBODIMENTS

The following embodiments are exemplary and should not be considered to limit the present invention.

Embodiment 1. A method of modulating the immune system of a subject, comprising:
receiving ultrasonic waves from an external ultrasonic transducer;
converting energy from the ultrasonic waves into electrical energy that powers a fully implanted medical device in the subject, the device comprising two or more electrodes that are in electrical communication with the splenic nerve of the subject; and
electrically stimulating the splenic nerve using the device.

Embodiment 2. A method of reducing inflammation in a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject; and
electrically stimulating the splenic nerve using the device, wherein the stimulation is configured to reduce inflammation in the subject.

Embodiment 3. The method of embodiment 2, wherein the inflammation is caused by an autoimmune disease.

Embodiment 4. The method of embodiment 2 or 3, wherein the inflammation is caused by rheumatoid arthritis, Crohn's disease, colitis, lupus, or spondylitis.

Embodiment 5. A method of treating an inflammatory disease in a subject, comprising:
receiving ultrasonic waves from an external ultrasonic transducer;
converting energy from the ultrasonic waves into electrical energy that powers a fully implanted medical device in the subject having the inflammatory disease, the device comprising two or more electrodes that contact the splenic nerve of the subject; and
electrically stimulating the splenic nerve using the device, wherein the stimulation is configured to reduce inflammation in the subject.

Embodiment 6. The method of embodiment 5, wherein the inflammatory disease is an autoimmune disease.

Embodiment 7. The method of embodiment 5 or 6, wherein the inflammatory disease is rheumatoid arthritis, Crohn's disease, colitis, lupus, or spondylitis.

Embodiment 8. A method of reducing a blood concentration of an inflammatory cytokine in a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject; and
electrically stimulating the splenic nerve using the device, wherein the stimulation is configured to reduce the blood concentration of the inflammatory cytokine in the subject.

Embodiment 9. The method of embodiment 8, wherein the method reduces splenic release of the inflammatory cytokine.

Embodiment 10. The method of embodiment 8 or 9, wherein the inflammatory cytokine is tumor necrosis factor alpha (TNF-α), interleukin-6 (IL-6), interleukin-1β (IL-1β), or high mobility group box 1 (HMGB1).

Embodiment 11. The method of any one of embodiment 1-10, wherein electrically stimulating the splenic nerve decreases activation of one or more immune cells in the subject.

Embodiment 12. The method of embodiment 11, wherein electrically stimulating the splenic nerve decreases activation of natural killer (NK) cells in the subject.

Embodiment 13. The method of any one of embodiments 1-12, wherein the splenic nerve is electrically stimulated using one or more electrical pulses less than 500 μs in length.

Embodiment 14. The method of any one of embodiment 1-13, wherein the splenic nerve is electrically stimulated using one or more electrical pulses about 100 μs to 200 μs in length.

Embodiment 15. The method embodiment 13 or 14, wherein the one or more electrical pulses have an amplitude of about 750 μA to about 10 mA.

Embodiment 16. The method of any one of embodiments 1-15, wherein the splenic nerve is electrically stimulated using a plurality of pulse trains comprising two or more electrical pulses, the pulse trains separated by a dwell time of about 500 ms or more.

Embodiment 17. The method of any one of embodiments 1-16, wherein electrically stimulating the splenic nerve occurs in response to a trigger signal.

Embodiment 18. The method of embodiment 17, wherein the trigger signal is encoded in the ultrasonic waves received by the implanted medical device.

Embodiment 19. The method of embodiment 17 or 18, wherein the trigger signal is based on splenic nerve activity.

Embodiment 20. The method of any one of embodiments 17-19, wherein the trigger signal is based on a deviation from a baseline splenic nerve activity.

Embodiment 21. The method of embodiment 19 or 20, wherein the splenic nerve activity is detected by the implanted medical device.

Embodiment 22. The method of any one of embodiments 17-21, wherein the trigger signal is further based on a measured physiological condition.

Embodiment 23. The method of embodiment 22, wherein the physiological condition is a temperature, a pulse rate, or a blood pressure.

Embodiment 24. The method of embodiment 22 or 23, wherein the physiological condition is measured by the implanted medical device.

Embodiment 25. The method of any one of embodiments 22-24, comprising emitting an ultrasonic backscatter encoding information related to the splenic nerve activity or the physiological condition.

Embodiment 26. The method of embodiment 25, wherein the ultrasonic backscatter encoding the information related to the splenic nerve activity or the physiological condition is received by an external device.

Embodiment 27. The method of embodiment 25 or 26, wherein the ultrasonic backscatter further encodes information related to the status of the device or one or more electrical pulses emitted by the device.

Embodiment 28. The method of any one of embodiments 19-27, comprising transmitting, at the external device, ultrasonic waves that encode the trigger signal.

Embodiment 29. A method of monitoring an immune system of a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject;
detecting an electrical activity of the splenic nerve;
emitting an ultrasonic backscatter encoding information related to the electrical activity of the splenic nerve; and
monitoring a deviation in the electric activity relative to a baseline electrical activity indicates a change in the status of the immune system of the subject.

Embodiment 30. The method of embodiment 29, wherein an increase in the electrical activity of the splenic nerve indicates an increase in immune system activity.

Embodiment 31. The method of embodiment 29 or 30, wherein the method comprises monitoring inflammation in the subject, wherein a change in the electrical activity of the splenic nerve indicates a change in inflammation in the subject.

Embodiment 32. The method of embodiment 31, wherein an increase in the electrical activity of the splenic nerve indicates a change in inflammation in the subject.

Embodiment 33. The method of embodiment 31 or 32, wherein a decrease in the electrical activity of the splenic nerve indicates a decrease in inflammation in the subject.

Embodiment 34. The method of any one of embodiments 31-33, wherein the inflammation is caused by an autoimmune disease.

Embodiment 35. The method of any one of embodiments 31-34, wherein the inflammation is caused by rheumatoid arthritis, Crohn's disease, colitis, lupus, or spondylitis.

Embodiment 36. The method of any one of embodiments 29-35, wherein the method comprises monitoring a therapy administered to the subject.

Embodiment 37. The method of embodiment 36, further comprising administering the therapy to the subject.

Embodiment 38. The method of embodiment 36 or 37, wherein the therapy is an anti-inflammatory therapy.

Embodiment 39. The method of embodiment 38, wherein the anti-inflammatory therapy is administered in response to a detected increase in inflammation.

Embodiment 40. The method of embodiment 38 or 39, wherein the anti-inflammation therapy is a drug therapy.

Embodiment 41. The method of embodiment 38 or 39, wherein the anti-inflammatory therapy comprises electrically stimulating a nerve.

Embodiment 42. The method of embodiment 41, wherein the nerve is a vagus nerve, a celiac ganglion, a subdiaphragmatic vagus nerve, a splanchnic nerve, a superior mesenteric nerve, or the splenic nerve of the subject.

Embodiment 43. The method of any one of embodiments 29-42, comprising receiving the ultrasonic backscatter at an external device.

Embodiment 44. A method of administering a therapy for inflammation in a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject;
detecting an electrical activity of the splenic nerve;

emitting an ultrasonic backscatter encoding the electric activity of the splenic nerve;
monitoring a deviation in the electric activity of the splenic nerve compared to a baseline electrical activity of the splenic nerve; and
administering an anti-inflammatory therapy if the deviation in the electrical activity of the splenic nerve indicates an inflammatory response.

Embodiment 45. The method of embodiment 44, wherein the therapy comprises a drug therapy.

Embodiment 46. The method of embodiment 44, wherein the therapy comprises electrically stimulating a nerve.

Embodiment 47. The method of embodiment 46, wherein the nerve is a vagus nerve, a celiac ganglion, a subdiaphragmatic vagus nerve, a splanchnic nerve, a superior mesenteric nerve, or the splenic nerve of the subject.

Embodiment 48. A method of adjusting a therapy administered to a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject;
detecting an electrical activity of the splenic nerve;
emitting an ultrasonic backscatter encoding the electric activity of the splenic nerve;
receiving the ultrasonic backscatter at an external device;
monitoring a deviation in the electrical activity of the splenic nerve compared to a baseline electrical activity of the splenic nerve, wherein the deviation indicates a change in immune system status of the subject; and
adjusting the therapy based on the change in immune system status of the subject.

Embodiment 49. The method of embodiment 48, wherein the change in immune system status is a change in an inflammatory response.

Embodiment 50. The method of embodiment 48 or 49, further comprising administering the therapy to the subject.

Embodiment 51. The method of any one of embodiments 48-50, wherein the therapy is an anti-inflammatory therapy.

Embodiment 52. The method of embodiment 51, wherein the anti-inflammatory therapy is adjusted if the anti-inflammatory therapy does not result in a desired effect or results in an undesired inflammatory response.

Embodiment 53. The method of embodiment 51 or 52, wherein the anti-inflammatory therapy is discontinued if the anti-inflammatory therapy obtains a desired effect.

Embodiment 54. The method of any one of embodiments 48-53, wherein the therapy comprises a drug therapy.

Embodiment 55. The method of embodiment 54, wherein adjusting the therapy comprises adjusting a frequency or dose of the therapy administered to the subject.

Embodiment 56. The method of any one of embodiments 48-54, wherein the therapy comprises electrically stimulating a nerve.

Embodiment 57. The method of embodiment 56, wherein the nerve is a vagus nerve, a celiac ganglion, a subdiaphragmatic vagus nerve, a splanchnic nerve, a superior mesenteric nerve, or the splenic nerve of the subject.

Embodiment 58. The method of embodiment 56 or 57, wherein adjusting the therapy comprises adjusting a frequency, voltage, current, or duration of one or more electrical pulses used to electrically stimulate the nerve.

Embodiment 59. The method of any one of embodiments 44-58, wherein the subject has an autoimmune disease that causes inflammation.

Embodiment 60. The method of any one of embodiments 44-59, wherein the subject has rheumatoid arthritis, Crohn's disease, colitis, lupus, or spondylitis.

Embodiment 61. A method of modulating blood pressure in a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject; and
electrically stimulating the splenic nerve using the device, wherein the stimulation is configured to modulate blood pressure in the subject.

Embodiment 62. A method of treating hypertension in a subject, comprising:
receiving ultrasonic waves from an external ultrasonic transducer;
converting energy from the ultrasonic waves into electrical energy that powers a fully implanted medical device in the subject, the device comprising two or more electrodes that contact the splenic nerve of the subject; and
electrically stimulating the splenic nerve using the device, wherein the stimulation is configured to reduce hypertension in the subject.

Embodiment 63. The method of embodiment 61 or 62, wherein the electrically stimulating the splenic nerve comprises blocking splenic nerve activity.

Embodiment 64. The method of any one of embodiments 61-63, wherein electrically stimulating the splenic nerve comprises emitting a plurality of electrical pulses at a frequency of about 1 kHz or higher.

Embodiment 65. The method of any one of embodiments 60-63, wherein electrically stimulating the splenic nerve occurs in response to a trigger signal.

Embodiment 66. The method of embodiment 65, wherein the trigger signal is encoded in the ultrasonic waves received by the implanted medical device.

Embodiment 67. The method of embodiment 65 or 66, wherein the trigger signal is based on splenic nerve activity.

Embodiment 68. The method of any one of embodiments 65-67, wherein the trigger signal is based on a deviation from a baseline splenic nerve activity.

Embodiment 69. The method of embodiment 67 or 68, wherein the splenic nerve activity is detected by the implanted medical device.

Embodiment 70. The method of any one of embodiments 67-69, wherein the trigger signal is further based on a measured physiological condition.

Embodiment 71. The method of embodiment 70, wherein the physiological condition is a temperature, a pulse rate, or a blood pressure.

Embodiment 72. The method of embodiment 70 or 71, wherein the physiological condition is measured by the implanted medical device.

Embodiment 73. The method of any one of embodiments 69-70, comprising emitting an ultrasonic backscatter encoding information related to the splenic nerve activity or the physiological condition.

Embodiment 74. The method of embodiment 73, wherein the ultrasonic backscatter encoding the information related to the splenic nerve activity or the physiological condition is received by an external device.

Embodiment 75. The method of embodiment 73 or 74, wherein the ultrasonic backscatter further encodes information related to the status of the device or one or more electrical pulses emitted by the device.

Embodiment 76. The method of any one of embodiments 65-75, comprising transmitting, at the external device, ultrasonic waves that encode the trigger signal.

Embodiment 77. The method of any one of embodiments 1-76, comprising transmitting the ultrasonic waves that power the implantable medical device using the external device.

Embodiment 78. The method of any one of embodiments 1-77, wherein the implanted medical device is fully implanted with in the perivascular fascia surrounding the splenic nerve and splenic artery.

Embodiment 79. The method of any one of embodiments 1-78, wherein the splenic nerve is not separated from the splenic artery.

Embodiment 80. The method of any one of embodiments 1-79, wherein the implantable medical device does not comprise a battery.

Embodiment 81. The method of any one of embodiments 1-80, wherein the implantable medical device does not comprise a radiofrequency communication system.

Embodiment 82. The method of any one of embodiments 1-81, wherein the implanted medical device does not comprise an electrical lead that extends from a body of the device.

Embodiment 83. The method of any one of embodiments 1-82, wherein the implanted medical device comprises a body comprising an ultrasonic transducer, and wherein the body of the device is attached to the splenic nerve or a splenic artery.

Embodiment 84. The method of embodiment 83, wherein the implanted medical device comprises a splenic nerve attachment member attached to a body, wherein the splenic nerve attachment member is sized and configured to attach the device to the splenic nerve or a splenic artery and position two or more electrodes in electrical communication with the splenic nerve Embodiment 85. The method of any one of embodiments 1-84, wherein the implanted medical device has a length of about 5 mm or less in the longest dimension.

Embodiment 86. The method of any one of embodiments 1-84, wherein the implanted medical device has a volume of about 5 mm³ or smaller.

Embodiment 87. The method of any one of embodiments 1-86, wherein the subject is anti-cyclic citrullinated peptide (anti-CCP) positive or fails to respond to a disease-modifying anti-rheumatic drug (DMARD).

Embodiment 88. The method of any one of embodiments 1-87, wherein the subject is a human.

Embodiment 89. An implantable medical device, comprising:
a body comprising an ultrasonic transducer configured to receive ultrasonic waves and convert energy from the ultrasonic waves into an electrical energy that powers the device;
two or more electrodes in electrical communication with the ultrasonic transducer, wherein the electrodes are configured to electrically stimulate a splenic nerve or detect a splenic nerve activity; and
a splenic nerve attachment member attached to the body, wherein the splenic nerve attachment member is sized and configured to attach the device to the splenic nerve or splenic artery and position the two or more electrodes in electrical communication with the splenic nerve.

Embodiment 90. The implantable medical device of embodiment 89, wherein the splenic nerve attachment member comprises a clip that is configured to at least partially surround the splenic nerve or splenic artery.

Embodiment 91. The implantable medical device of embodiment 90, wherein the clip comprises a plurality of flexible legs that extend below the body.

Embodiment 92. The implantable medical device of embodiment 91, wherein the implantable device comprises a hook or loop configured to maneuver at least one of the flexible legs in response to maneuvering the hook or loop.

Embodiment 93. The implantable medical device of embodiment 92, wherein the hook or loop is positioned at a terminus of one of the flexible legs.

Embodiment 94. The implantable medical device of embodiment 92, wherein the hook or loop is positioned proximal to the body.

Embodiment 95. The implantable medical device of any one of embodiments 91-94, wherein the flexible legs are curved.

Embodiment 96. The implantable medical device of embodiment 95, wherein the legs extend away from the body before curving toward the body as the legs extend below the body.

Embodiment 97. The implantable medical device of embodiment 96, wherein the plurality of flexible legs comprises at least one pair of legs, wherein the pair of legs comprises a first leg and a second leg that extend away from and below the body in opposite directions.

Embodiment 98. The implantable medical device of embodiment 97, wherein the first leg and the second leg are connected by a crossbar connected to the body.

Embodiment 99. The implantable medical device of embodiment 98, wherein the crossbar is connected to the body of the device through a flexible member.

Embodiment 100. The implantable medical device of embodiment 99, wherein the flexible member is a hinge.

Embodiment 101. The implantable medical device of any one of embodiments 97-100, wherein the device comprises two pairs of legs, wherein each pair of leg is positioned on opposite sides of the body.

Embodiment 102. The implantable medical device of any one of embodiments 91-101, wherein the legs are attached to the body through a bottom surface of the body.

Embodiment 103. The implantable medical device of any one of embodiments 91-101, wherein the legs are attached to the body through a sidewall of the body.

Embodiment 104. The implantable medical device of any one of embodiments 91-103, wherein the legs comprise a metal, metal alloy, ceramic, silicon, or a non-polymeric material.

Embodiment 105. The implantable medical device of any one of embodiments 91-104, wherein the legs comprise an elastomeric coating or a non-elastomeric polymer coating.

Embodiment 106. The implantable medical device of embodiment 105, wherein the elastomeric coating or the non-elastomeric polymer coating is bioinert.

Embodiment 107. The implantable medical device of embodiment 105 or 106, wherein the elastomeric coating or the non-elastomeric polymer coating is a silicone, a poly(p-xylylene) polymer, a urethane polymer, or a polyimide.

Embodiment 108. The implantable medical device of any one of embodiments 105-107, wherein at least one of the legs comprises an outer surface coated with the elastomeric coating or the non-elastomeric polymer coating and an inner surface comprising at least one electrode that is not coated with the elastomeric coating or the non-elastomeric polymer coating.

Embodiment 109. The implantable medical device of any one of embodiments 89-108, wherein the body comprises a bottom surface, and the two or more electrodes are terminate on the bottom of the body.

Embodiment 110. The implantable medical device of any one of embodiments 89-109, wherein the two or more electrodes are positioned on the clip.

Embodiment 111. The implantable medical device of embodiment 110, wherein the clip comprises a plurality of flexible legs that extend below the body, and the two or more electrodes are positioned on the flexible legs.

Embodiment 112. The implantable medical device of any one of embodiments 89-111, wherein the body comprises a housing.

Embodiment 113. The implantable medical device of embodiment 112, wherein the housing comprises or is coated with a bioinert material.

Embodiment 114. The implantable medical device of embodiment 113, wherein the housing comprises the bioinert material, and wherein the bioinert material of the housing comprises titanium or a ceramic.

Embodiment 115. The implantable medical device of any one of embodiments 89-114, wherein the body comprises an integrated circuit electrically connected to the ultrasonic transducer and the two or more electrodes.

Embodiment 116. The implantable medical device of embodiment 115, wherein the integrated circuit comprises an energy storage circuit comprising a capacitor.

Embodiment 117. The implantable medical device of any one of embodiments 89-116, wherein the body is about 5 mm or less in length in the longest dimension.

Embodiment 118. The implantable medical device of any one of embodiments 89-117, wherein the ultrasonic transducer is configured to emit an ultrasonic backscatter that encodes information related to splenic nerve activity.

Embodiment 119. The implantable medical device of embodiment 118, wherein the information further comprises information related to a physiological condition, a device status, or an emitted electrical pulse.

Embodiment 120. The implantable medical device of any one of embodiments 89-119, wherein the ultrasonic transducer is configured to receive ultrasonic waves that encode instructions for operating the implantable device.

Embodiment 121. The implantable medical device of embodiment 120, wherein the instructions comprise a trigger signal that operates the implantable device to emit an electrical pulse to the nerve.

Embodiment 122. The implantable medical device of any one of embodiments 89-121, wherein the splenic nerve attachment member is sized and configured to attach the device to the splenic nerve of a human.

Embodiment 123. The implantable medical device of any one of embodiments 89-122, wherein the implantable medical device does not comprise a battery.

Embodiment 124. The implantable medical device of any one of embodiments 89-123, wherein the implantable medical device does not comprise a radiofrequency communication system.

Embodiment 125. The implantable medical device of any one of embodiments 89-124, wherein the implanted medical device does not comprise an electrical lead that extends from the body of the device without terminating on the splenic nerve attachment member.

Embodiment 126. The implantable medical device of any one of embodiments 89-125, wherein the two or more electrodes are configured to electrically stimulate a splenic nerve and detect a splenic nerve activity.

Embodiment 127. The implantable medical device of any one of embodiments 89-126, wherein the two or more electrodes comprise:
  a first electrode and a second electrode configured to electrically stimulate the splenic nerve;
  and a third electrode and a fourth electrode configured to detect the splenic nerve activity.

Embodiment 128. A closed-loop system, comprising:
  the implantable medical device of any one of embodiments 89-127; and
  an interrogator configured to transmit the ultrasonic waves to the implantable medical device, wherein the ultrasonic waves further encode a trigger signal in response to a detected splenic nerve activity, a change in a detected splenic nerve activity, a physiological condition, or a change in a physiological condition.

Embodiment 129. A method of modulating splenic nerve activity in a subject, comprising:
  receiving ultrasonic waves from an external ultrasonic transducer;
  converting energy from the ultrasonic waves into electrical energy that powers a fully implanted medical device in the subject, the device comprising two or more electrodes that are in electrical communication with the splenic nerve of the subject; and
  electrically stimulating the splenic nerve using the device.

Embodiment 130. A method of modulating an immune system of a subject, comprising electrically stimulating the splenic nerve of the subject using a pulse train comprising a plurality of biphasic electrical pulses.

Embodiment 131. The method of embodiment 130, wherein the biphasic electrical pulses comprises an anodal phase followed by a cathodal phase.

Embodiment 132. The method of embodiment 130 or 131, wherein the pulse train is configured to increase a blood concentration of one or more inflammatory cytokines.

Embodiment 133. The method of embodiment 130 or 131, wherein the pulse train is configured to decrease a blood concentration of one or more inflammatory cytokines.

Embodiment 134. The method of embodiment 132 or 133, wherein the one or more inflammatory cytokines comprises one or more of TNF-α, IL-6, IL-1β or HMGB1.

Embodiment 135. The method of embodiment 130 or 131, wherein the pulse train is configured to increase activation of an immune cell.

Embodiment 136. The method of embodiment 130 or 131, wherein the pulse train is configured to decrease activation of an immune cell.

Embodiment 137. The method of embodiment 135 or 136, wherein the immune cell is a natural killer (NK) cell.

Embodiment 138. The method of any one of embodiments 130-137, wherein the electrical pulses are less than 1 ms in length.

Embodiment 139. The method of any one of embodiments 130-138, wherein the frequency of the electrical pulses is about 100 Hz or less.

Embodiment 140. The method of any one of embodiments 130-139, wherein the method is implemented using an implantable device, such as a fully implantable device described herein.

Embodiment 141. The method of any one of embodiments 130-140, the method further comprises receiving ultrasonic waves from an external ultrasonic transducer; converting energy from the ultrasonic waves into electrical energy that powers a fully implanted medical device in the subject, the device comprising two or more electrodes that are in electrical communication with the splenic nerve of the subject.

EXAMPLES

The application may be better understood by reference to the following non-limiting examples, which are provided as exemplary embodiments of the application. The following examples are presented in order to more fully illustrate embodiments and should in no way be construed as limiting the scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1: Stimulation of Splenic Nerve to Modulate Immune System

In this example, splenic nerve stimulation was used as a method to reduce the inflammatory response to an acute immune challenge, triggered by intravenous infusion of lipopolysaccharides. Adult male and female Lewis rats, weighing approximately 250-400 grams, were sourced from Charles River Laboratories in Wilmington, MA. Rats were housed in pairs on a 12-hour light/dark cycle and fed ad libitum. All experiments were performed according to local Animal Care and Use Committee guidelines.

Animals were fully anesthetized with isoflurane gas mixed with pure oxygen using a digital vaporizer (Kent Scientific, Torrington, CT). Animals were placed in the supine position, a rectal thermometer was inserted to monitor core temperature and control an infrared heating pad, and a pulse oximeter (Kent Scientific, Torrington, CT) was clipped to the right front paw to monitor oxygen saturation. Fur around the left flank and abdomen was clipped. The left femoral artery and vein were catheterized using medical-grade micro-urethane tubing (Scientific Commodities, Inc., Lake Havasu City, AZ), and catheters were locked with a solution of 50 U/ml sodium heparin from porcine intestinal mucosa (Sigma-Aldrich, St. Louis, MO). The arterial line was connected to a pressure transducer (Stoelting, Wood Dale, IL) in order to capture the arterial pressure waveform, and the venous line was used as an infusion and withdrawal point in later steps.

A midline laparotomy was performed in order to gain access to the abdominal cavity. The splenic neurovascular bundle was identified, and a segment was chosen in between the proximal origin from the celiac artery and the distal point at which the artery branches before entering the hilum of the spleen. A roughly 3 mm section of artery along with its accompanying splenic nerve branches was gently isolated from the vein and surrounding tissue and placed into a nerve cuff containing 3×50 µm-wide platinum electrodes spaced 1 mm apart (Microprobes, Inc., Gaithersburg, MD). A custom-fabricated counter electrode, made from a 3 mm×3 mm square of 0.004" platinum sheet, was placed nearby in contact with the pancreatic tissue a few millimeters away from the cuff. Finally, Ag/Cl pellet ground electrode (WPI, Sarasota, FL) was placed in the abdominal cavity.

In order to verify that the nerve cuff electrodes were in electrical contact with the splenic nerves, the three electrodes of the cuff and the ground electrode were connected in pseudo-tripolar configuration to a differential amplifier (A-M systems, Sequim, WA). Signals were amplified 1000× and bandpass filtered between 100 Hz and 5 kHz, and viewed on a digital oscilloscope (Tektronix, Beaverton, OR). The presence of spontaneous sympathetic nerve activity was used as an indicator that the cuff was placed correctly and that the nerves had not been injured by the surgical procedure. Stable nerve activity was monitored for 15 minutes before continuing to the next phase of the procedure.

Following verification of proper electrode placement, the splenic nerve was stimulated using a constant-current isolated pulse stimulator (A-M Systems, Sequim, WA). The positive terminal of the stimulator was connected to the counter electrode, and the negative terminal was connected to the middle electrode of the nerve cuff. Pulses were monopolar, cathodal-first, biphasic, square-wave pulses with the following parameters: 300 µs pulse length (150 µs cathodal phase, 60 µs inter-phase interval, 150 µs anodal phase), pulse amplitudes between 1 and 1.8 mA, and at an average frequency of 5 Hz over a 20 min period. A total of 27 rats received the stimulatory pulses, and 24 rats received no stimulatory pulse (control).

In order to trigger an innate immune reaction, a sub-lethal dose of lipopolysaccharides (LPS) from *E. coli* (Sigma-Aldrich, St. Louis, MO) was infused at a concentration of 60 µg/kg in a 50011.1 bolus of saline through the venous catheter, 10 mins after the end of stimulation. LPS was prepared fresh daily from 1 mg/ml aliquots frozen at −20° C.

Approximately 200 µl of blood was drawn from the venous catheter at the following intervals: "baseline", which corresponded to the end of the 15-min spontaneous recording period and immediately prior to the onset of stimulation, and then 45, 90, 135, and 180 min after infusion of LPS. Blood was allowed to clot for 30 min at room temperature, and then centrifuged for 20 min, after which the serum was immediately extracted and frozen at −20° C. until further analysis.

Serum cytokine (TNF-α and IL-1β levels were determined using quantitative ELISA kits (R&D systems, Minneapolis, MN) according to manufacturer instructions. Fluorescence absorption was measured using a 96-well plate reader (Thermo-Fisher Scientific, Waltham, MA). A 4-parameter logistic regression curve was used to compute cytokine concentrations in samples by fitting the curve to known standard samples supplied by the manufacturer.

Figure 13A:
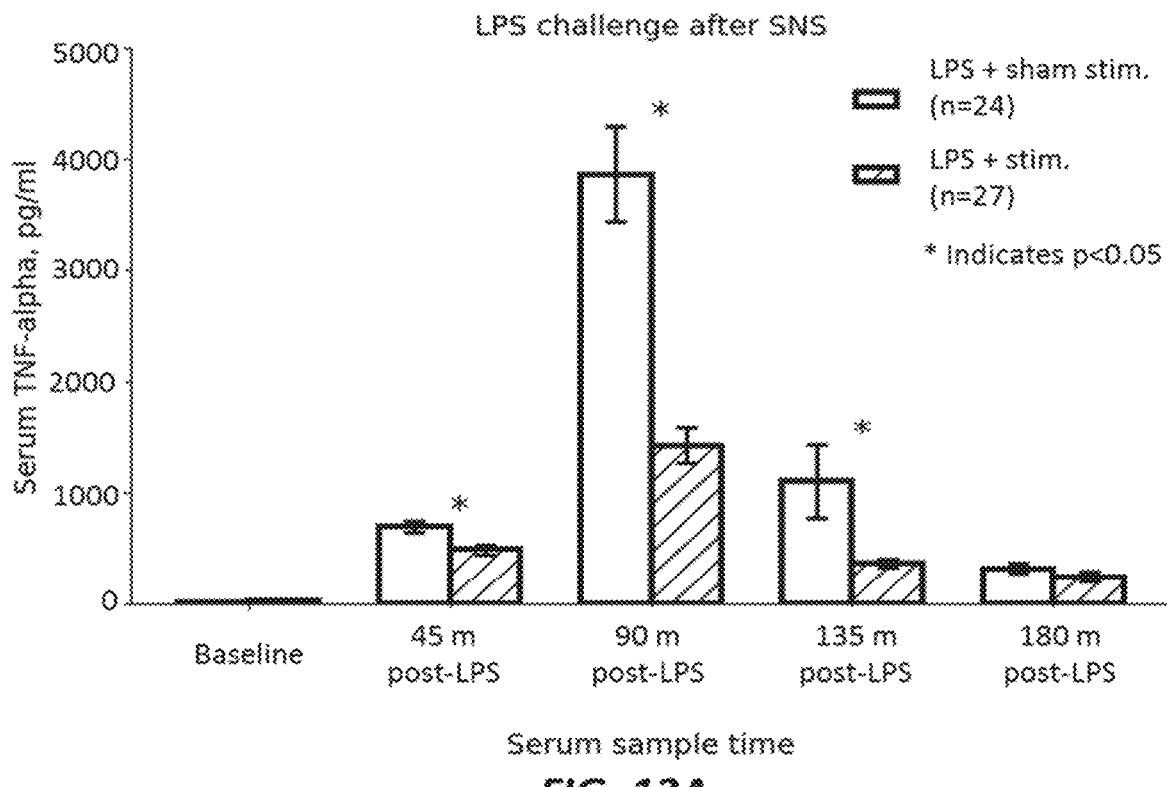
FIGS. 13A-13B shows the TNF-α (FIG. 13A) and IL-1β (FIG. 13B) serum concentration in rats with or without stimulation of the splenic nerve for 20 minutes using monopolar, cathodal-first, biphasic, square-wave pulses 300 μs in length (150 μs cathodal phase and 150 μs anodal phase, with a 60 μs inter-phase interval), 1.8 mA pulse amplitude, and with a 200 ms dwell time between the biphasic pulses.
Figure 13B:
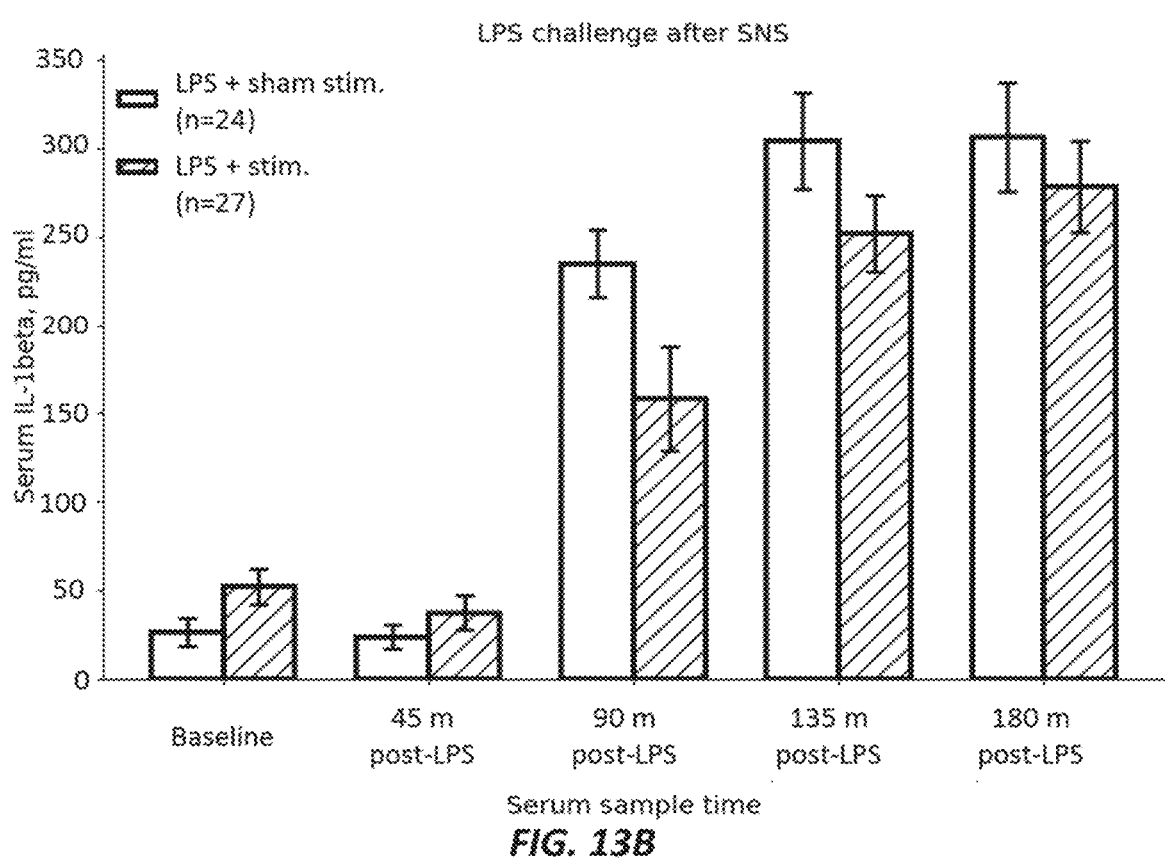

Serum concentration of TNF-α and IL-1β measured in each sample is shown relative to the onset of LPS infusion) in FIG. 13A and FIG. 13B, respectively. In FIG. 13B, only animals receiving tonic stimulation pulses between 1.5 mA and 1.8 mA are shown, as lower amplitude stimulation did not appear to influence IL-1β levels. TNF-α serum concentration in both cohorts peaked about 90 minutes following LPS administration. The immune suppressing nerve stimulation resulted in a substantial decrease of peak TNF-α serum concentration compared to the serum concentration in rats that did not receive the immune suppressing nerve stimulation (3872 pg/ml versus 1424 pg/ml, respectively). IL-1β serum concentration continued to increase during the 180 minutes experiment, although IL-1β serum concentration in rats that received the immune suppressing nerve stimulation was lower than the IL-1β serum concentration in rats that did not receive the immune suppressing nerve stimulation (292 pg/ml versus 296 pg/ml after 180 minutes, respectively).

Example 2: Splenic Nerve Stimulation-Response Curve and Stimulation Response Efficiency In order to test the efficacy of different stimulation pulse parameters for eliciting an evoked compound action potential (CAP) in the splenic nerve, the splenic neurovascular bundle was exposed and cuff electrodes were implanted for a cohort of rats as described in Example 1. Two approximately 3-mm lengths of nerve/artery complex were identified for electrode placement: A proximal location was chosen to be immediately distal to the branch point of the splenic nerve and artery from the celiac artery. A distal location was chosen to be immediately proximal to the point at which the splenic artery splits into several branches before entering the hilum of the spleen. This was done to maximize the distance between recording and stimulating electrodes in order to ensure that the neural response would not be obscured by the stimulus artifact. Typical separation between the proximal and distal locations was between 10 and 15 mm. A cuff electrode for stimulation was placed at the proximal location, while a cuff electrode for recording was placed at the distal location. Stimulation cathodal-first, biphasic, square-wave pulses of varying parameters (pulse length and/or amplitude) were delivered at the stimulating electrodes, and the evoked CAP was measured and recorded at the recording electrodes. For each set of parameters, we generated a recruitment curve by determining the minimum amplitude pulse (in mA) necessary to evoke a measurable CAP (in $\mu V$), and then increasing the amplitude in a stepwise manner until the peak-to-peak amplitude of the CAP no longer grew with increased pulse amplitude—the saturation point at which the stimulation pulses were activating all of the axons in the nerve. For each pulse amplitude level, the splenic nerve was stimulated with 100 pulses, and the average CAP of those 100 trials was used to compute the peak-to-peak response. A direct comparison of the efficiency of each set of parameters in terms of the amount of charge required to evoke a given amplitude CAP from the nerve can be compared in this manner, as the charge delivered by a square current pulse is the product of the amplitude and the duration.

Figure 14A:
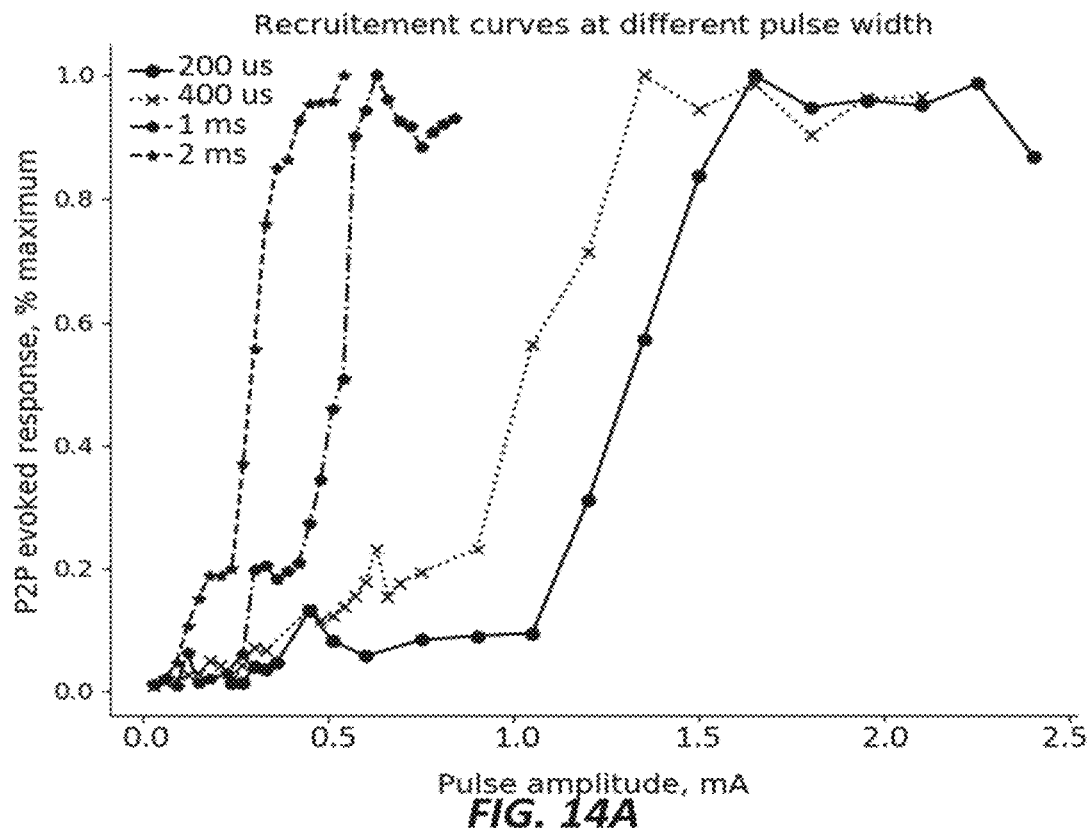
FIG. 14A shows evoked peak-to-peak (P2P) compound action potential (CAP) response upon stimulation of the splenic nerve for 2 ms, 1 ms, 400 μs, or 200 μs (split evenly between cathodal and anodal phases, with a 60 μs inter-phase interval) at various amplitude ranges (ranging from 50 μA to 2.5 mA) using cathodal-first, biphasic, square-wave pulses. Longer pulses required lower pulse amplitude to evoke the same peak-to-peak CAP response.
Figure 14B:
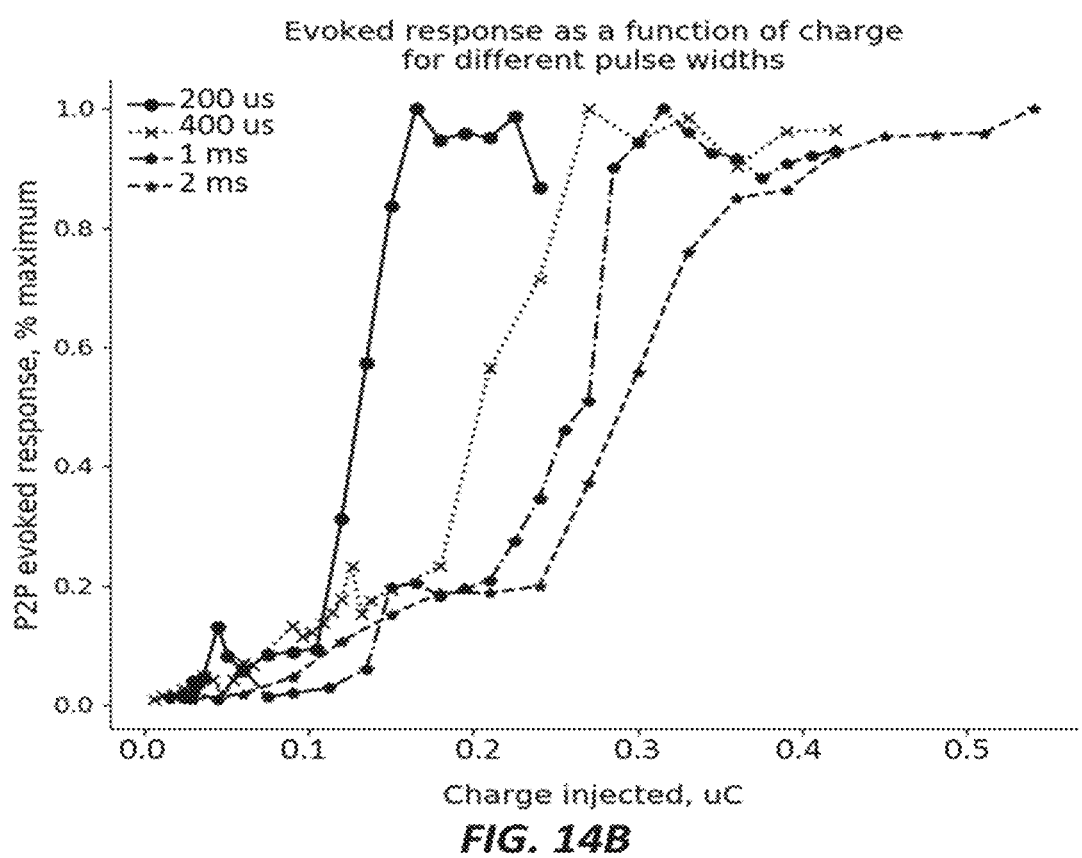
FIG. 14B shows the evokes peak-to-peak (P2P) compound action potential (CAP) response upon stimulation of the splenic nerve for 2 ms, 1 ms, 400 μs, or 200 μs (split evenly between cathodal and anodal phases, with a 60 μs inter-phase interval) at various charges (as determined by applied current amplitude and pulse length). This demonstrates the lower pulse length is more efficient when delivering a charge for a given CAP response.

In order to determine if different pulse widths had different charge efficiency, recruitment curves plotting the amplitude of evoked splenic nerve responses as a function of charge delivery for varying pulse widths were generated. It was found that for a given pulse amplitude, longer pulses elicited larger compound action potentials (CAPs) from the splenic nerve. Cathodal-first, biphasic, square-wave pulses of 200 μs, 400 μs, 1 ms, or 2 ms (split evenly between cathodal and anodal phases, with a 60 μs inter-phase interval) of varying amplitudes ranging from 50 μA to 2.5 mA were delivered at the stimulating electrodes, and the evoked CAP was measured and recorded at the recording electrodes. For a given pulse amplitude, longer pulses elicited larger CAPs from the splenic nerve (see FIG. 14A for exemplary results). However, by plotting the evoked response as a function of total charge injected at a given pulse, it can be seen that 200 μs pulses outperform longer pulse widths, as determined by the larger peak-to-peak evoked response in the detected signal. See FIG. 14B for exemplary results. Thus, delivery of a stimulatory pulse is more efficient using a shorter pulse width. The results shown in FIG. 14A and FIG. 14B were each taken from a single animal, although similar results were observed for different animals at different pulse lengths and/or amplitudes.

For stimulatory pulses with 200 μs pulse lengths, the pulse amplitude threshold for eliciting a splenic nerve response was around 1 mA and saturated around 1.8 mA, with larger amplitude pulses generating diminishing returns in terms of evoked responses.

Figure 15:
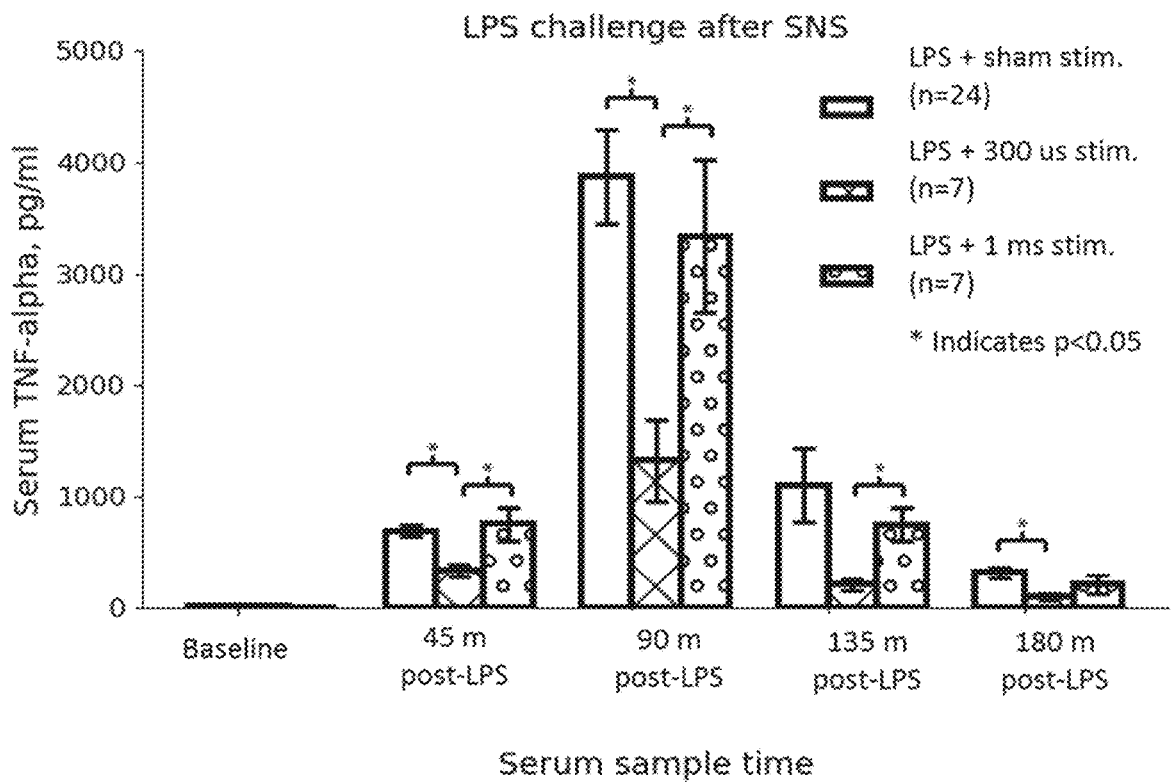
FIG. 15 shows serum TNF-α levels as a function of time after completion of 20 minutes of splenic nerve stimulation (followed by LPS infusion) using 1.8 mA pulses of 300 μs (n=7) or 1 ms (n=4) (split evenly between cathodal and anodal phases, with a 60 μs inter-phase interval), or unstimulated (n=24), applied to the splenic nerve at 5 Hz. The shorter pulse length was more effective at modulating the TNF-α level of the subject.

Example 3: Splenic Nerve Stimulation Pulse Lengths for Modulation of Cytokine Release In order to test how the splenic nerve stimulatory pulse length affects modulation of serum TNF-α level in subjects after stimulation of the splenic nerve, the splenic nerve was stimulated using a series of electrical pulses in a cohort of rats. The splenic neurovascular bundle was exposed and cuff electrodes were implanted for a cohort of rats as described in Example 1. The splenic nerve of the rats was stimulated for 20 minutes using a train of 1.8 mA cathodal-first, biphasic, square-wave pulses applied at 5 pulses per second (5 Hz) using 300 μs (n=7) or 1 ms pulse lengths (n=4) (pulse lengths split evenly between cathodal and anodal phases, with a 60 μs inter-phase interval), before a 10 minute rest followed by infusing the rats with 60 μg/kg LPS in a 500 μl bolus of saline through the venous catheter. A control cohort (n=24) was implanted with the electrodes and infused with LPS, but did not receive any stimulatory pulses. Serum TNF-α levels were measured as described in Example 1 at time points of 0 minutes, 45 minutes, 90 minutes, and 180 minutes following LPS infusion. Serum TNF-α levels as a function of time after LPS infusion and completion of stimulation is shown in FIG. 15. Stimulation with 1.8 mA pulse amplitudes was effective at reducing TNF-α release after LPS challenge when delivered with 200 μs pulse lengths, but not when 1 ms pulse lengths were used. Thus, pulse lengths were chosen in order to reduce the power needed to generate effective stimulation.

Figure 16:
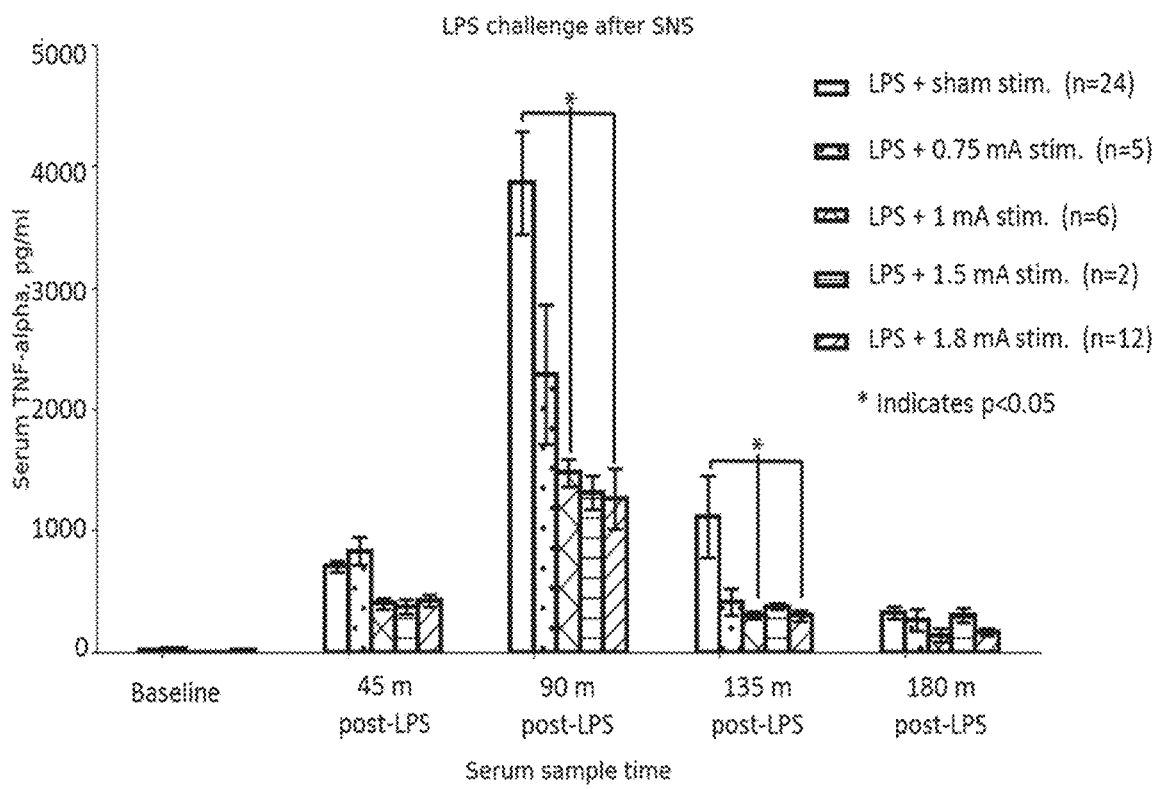
FIG. 16 shows serum TNF-α levels as a function of time after completion of 20 minutes of splenic nerve stimulation (followed by LPS infusion) using a train of 300 μs pulses (split evenly between cathodal and anodal phases, with a 60 μs inter-phase interval) applied at 5 pulses per second (5 Hz) using amplitudes of 750 μA (n=5), 1.0 mA (n=6), 1.5 mA (n=2) or 1.8 mA (n=12), or unstimulated (n=24). All amplitudes were effective at reducing serum TNF-α level.

Example 4: Splenic Nerve Stimulation Pulse Amplitude for Modulation of Cytokine Release In order to test how the splenic nerve stimulatory pulse amplitude affects modulation of serum TNF-α level in subjects after stimulation of the splenic nerve, the splenic nerve was stimulated using a series of electrical pulses in a cohort of rats. The splenic neurovascular bundle was exposed and cuff electrodes were implanted for a cohort of rats as described in Example 1. The splenic nerve of the rats was stimulated for 20 minutes using a train of 200 us cathodal-first, biphasic, square-wave pulses (split evenly between cathodal and anodal phases, with a 60 μs inter-phase interval) applied at 5 pulses per second (5 Hz) using amplitudes of 750 μA (n=5), 1.0 mA (n=4), 1.5 mA (n=2) or 1.8 mA (n=7) before a 10 minute rest followed by infusing the rats with 60 μg/kg LPS in a 500 μl bolus of saline through the venous catheter. A control cohort (n=24) was implanted with the electrodes and infused with LPS, but did not receive any stimulatory pulses. Serum TNF-α levels were measured as described in Example 1 at time points of 0 minutes, 45 minutes, 90 minutes, and 180 minutes following LPS infusion. Serum TNF-α levels as a function of time after LPS infusion and completion of stimulation is shown in FIG. 16.

All pulse amplitudes were effective in reducing the serum TNF-α levels after infusion, with currents of 1 mA or more producing the most effective TNF-α reduction.

Example 5: Splenic Nerve Stimulation for Increase of Cytokine Release

Figure 17:
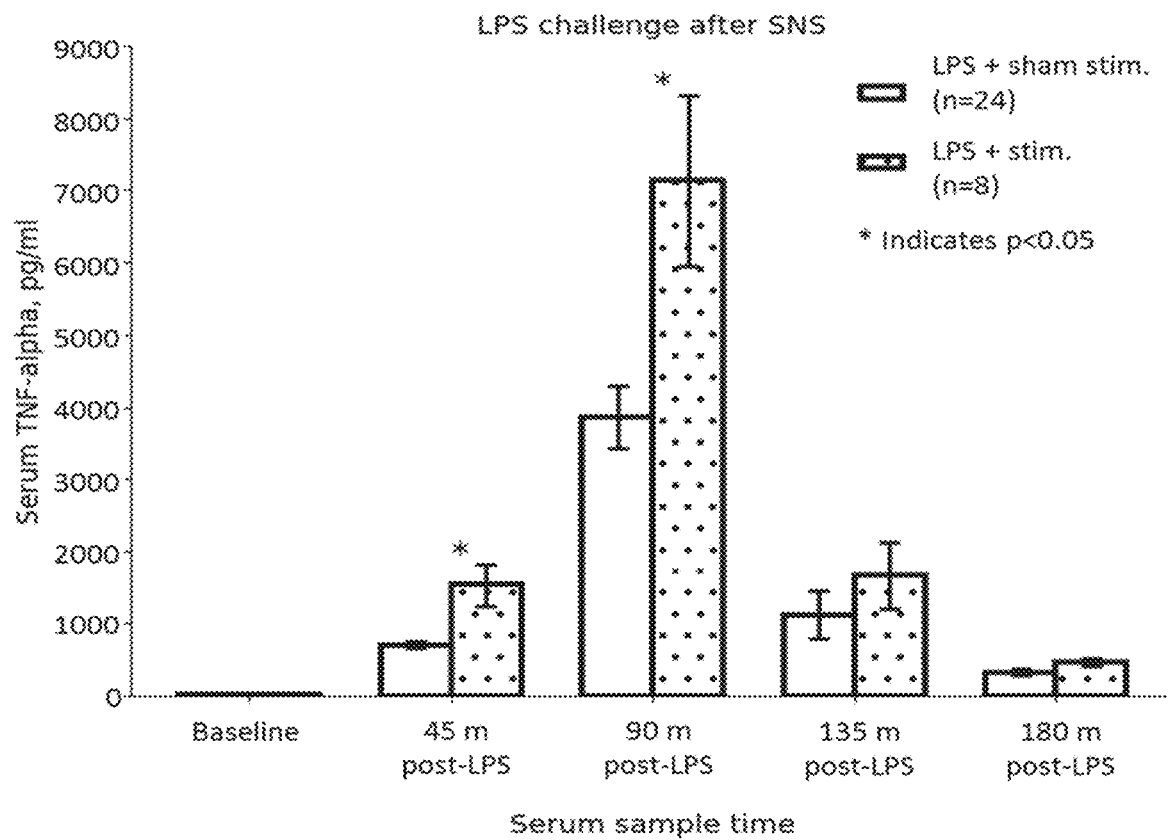
FIG. 17 shows serum TNF-α levels as a function of time starting immediately prior to the time of LPS infusion (baseline). After a 10 minute rest period following LPS administration, the splenic nerve was stimulated for 40 minutes using a train of 1.8 mA anodal-first, biphasic, square wave pulses at a rate of 30 per second (30 Hz), using a 300 μs (split evenly between cathodal and anodal phases, with a 60 μs inter-phase interval) pulse length (n=8), or unstimulated (n=24).

Experiments were also conducted to demonstrate cytokine levels (such as TNF-α levels) can also be increased by altering the stimulation parameters (e.g., pulse frequency and/or pulse polarity). In this experiment, splenic nerve stimulation was used as a method to increase the inflammatory response to an acute immune challenge triggered by IV infusion of LPS. A cohort of rats were implanted with splenic nerve stimulating electrode cuffs as described in Example 1, by placing the cuff around the splenic neurovascular bundle. The splenic nerve of the rats was stimulated for 40 minutes using a train of 1.8 mA anodal-first, biphasic, square wave pulses at a rate of 30 per second (30 Hz), using a 300 µs pulse length (n=8) (split evenly between cathodal and anodal phases, with a 60 µs inter-phase interval). The stimulation period began 10 minutes after infusing rats with 60 µg/kg LPS in a 500 µl bolus of saline through the venous catheter. A control cohort (n=24) was implanted with the electrodes and infused with LPS, but did not receive any stimulatory pulses. Serum TNF-α levels were measured as described in Example 1 at baseline (immediately before LPS administration), 45 minutes, 90 minutes, and 180 minutes following LPS infusion. Serum TNF-α levels as a function of time after LPS infusion and completion of stimulation is shown in FIG. 17. Rats receiving splenic nerve stimulation using these parameters had significantly higher TNF-α concentrations compared to the control animals at the 45-min timepoint (1536 pg/ml compared to 686 pg/ml, respectively), as well as the 90 min-timepoint (7123 pg/ml compared to 3869 pg/ml, respectively). These data demonstrate the potential of splenic nerve stimulation to augment immune responses.

Example 6: Splenic Nerve Stimulation Pulse Pattern for Modulation of Cytokine Release In order to test how the splenic nerve stimulatory pulse pattern affects modulation of serum TNF-α level in subjects after stimulation of the splenic nerve, the splenic nerve was stimulated using a series of electrical pulses in a cohort of rats with a dwell time (i.e., a quiescent period) between pulse trains. This was compared to a tonic stimulation paradigm, which delivered pulses at a steady frequency throughout the stimulation period. The total number of pulses delivered within a 2-second period was controlled between the study groups.

Figure 18:
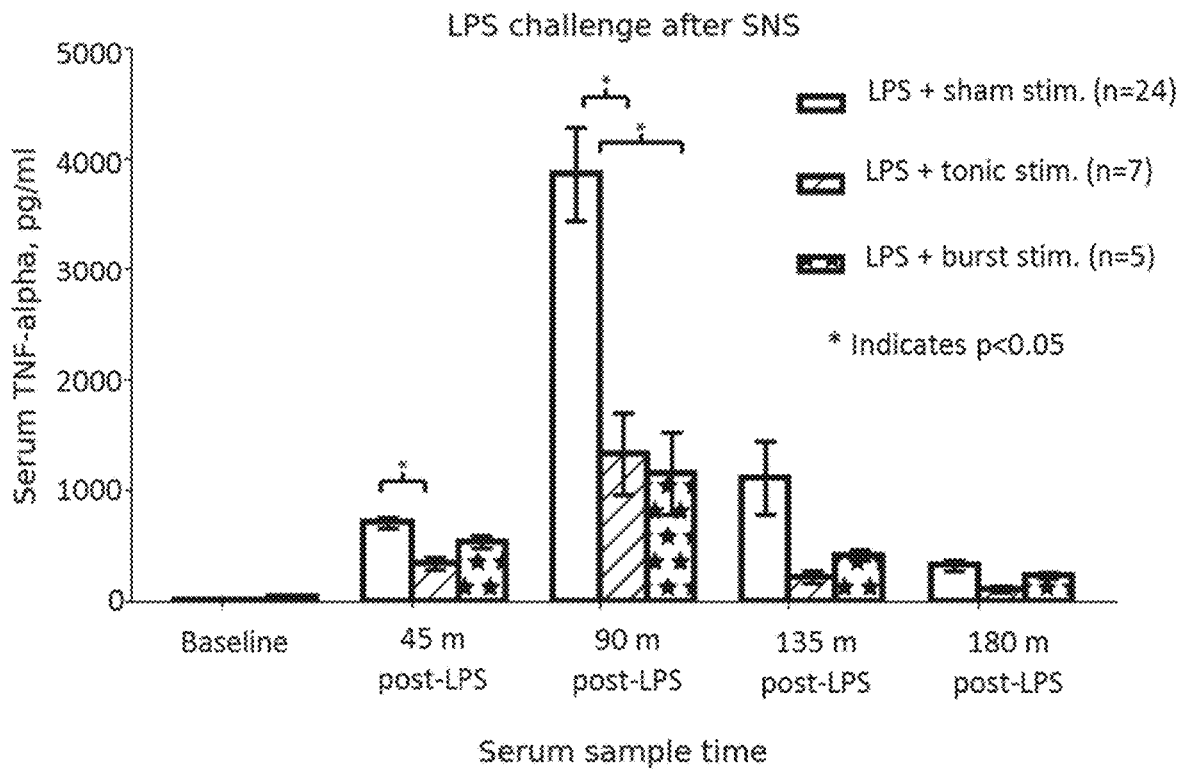
FIG. 18 shows serum TNF-α levels as a function of time starting after completion of 20 minutes of splenic nerve stimulation followed by 10 minutes rest and LPS infusion using either (1) regularly spaced pulses (5 Hz) of 1.8 mA (n=7); (2) a train of 10 pulses (20 Hz) for 500 ms, followed by a 1.5 second dwell time (n=5); or (3) unstimulated (n=24). The train of pulses followed by a dwell time was as effective as the regularly spaced pulses in modulating serum TNF-α level in the subject.

The splenic neurovascular bundle was exposed and cuff electrodes were implanted for a cohort of rats as described in Example 1. The splenic nerve was stimulated with a 1.8 mA "burst" pulse train (ten 300 µs pulses (split evenly between cathodal and anodal phases, with a 60 µs inter-phase interval) at 20 Hz for 500 ms, followed by a 1.5 second dwell time; n=5) or a 1.8 mA "tonic" pulse train (continuous 300 µs pulses (split evenly between cathodal and anodal phases, with a 60 µs inter-phase interval) at 5 Hz; n=7) for 20 minutes, before a 10 minute rest followed by infusing the rats with 60 µg/kg LPS in a 500 µl bolus of saline through the venous catheter. A control cohort (n=24) was implanted with the electrodes and infused with LPS, but did not receive any stimulatory pulses. Serum TNF-α levels were measured as described in Example 1 at time points of baseline, 45 minutes, 90 minutes, and 180 minutes following LPS infusion. Serum TNF-α levels as a function of time after LPS infusion and completion of stimulation is shown in FIG. 18 It was found that the burst pattern was equally effective for reducing TNF-α release compared to a tonic pattern, and thus may be an optimal method when delivering stimulation using a wirelessly-charged implanted device so that the device can charge during the dwell time.

Figure 19:
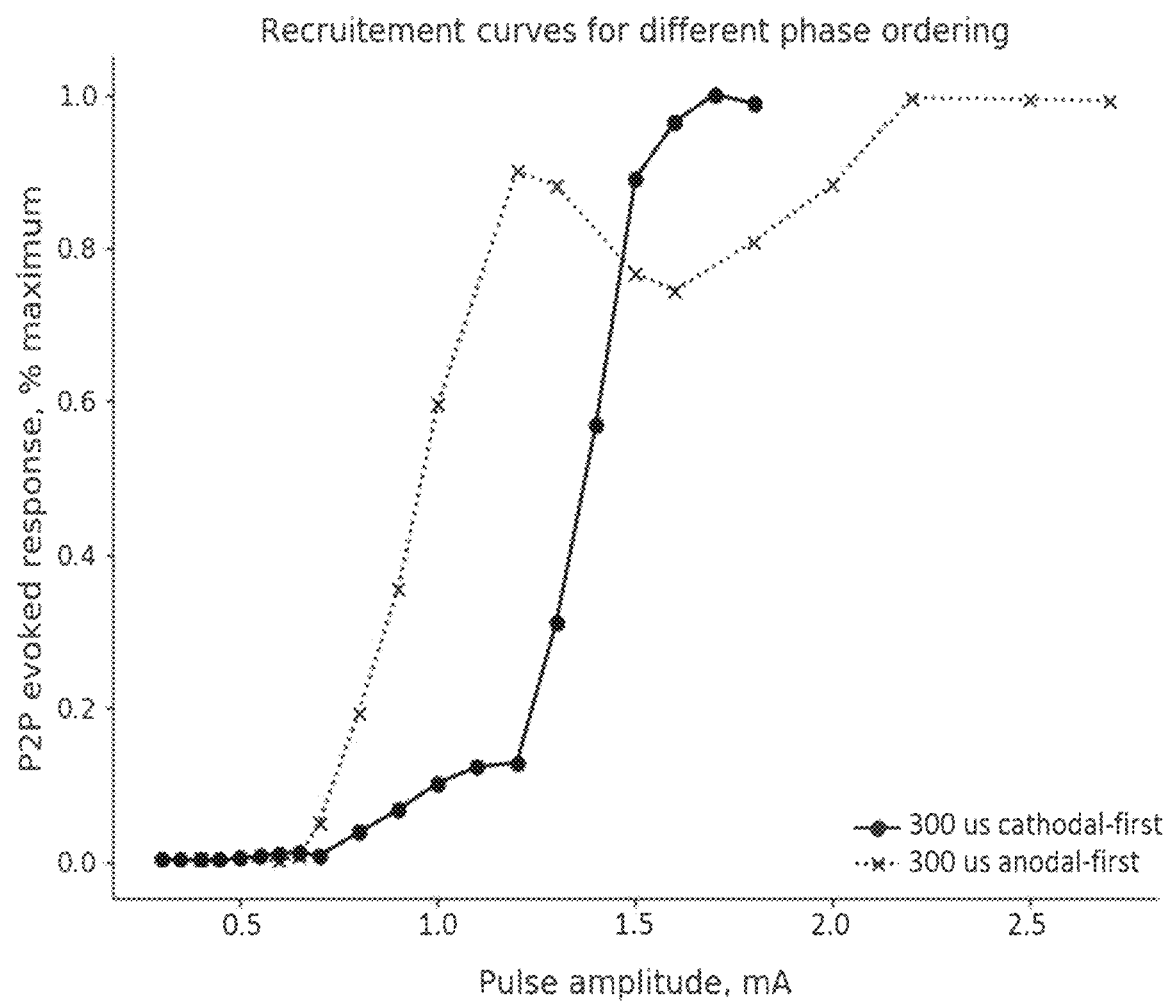
FIG. 19 shows peak-to-peak (P2) evoked response at various pulse amplitudes for biphasic, anodal-first 300 μs pulses or biphasic, cathodal-first 300 μs pulses (split evenly between cathodal and anodal phases, with a 60 μs inter-phase interval).

Example 7: Splenic Nerve Stimulation Pulse Polarity for Modulation of Splenic Nerve Activity In this example, the ordering of the biphasic pulses were varied in order to demonstrate the ability of anodal-first pulses to trigger splenic nerve responses at lower pulse amplitudes, thus improving energy efficiency. In a cohort of rats, the splenic neurovascular bundle was exposed and a pair of cuff electrodes was implanted on the nerve/artery complex as described in Example 2. Recruitment curves were generated for anodal- or cathodal-first, biphasic, square wave pulses of 300 µs in length (split evenly between cathodal and anodal phases, with a 60 µs inter-phase interval) of varying amplitudes ranging from 100 µA to 2.6 mA by delivering the stimulation to the proximal electrode and recording the CAP at the distal electrode. Data from a representative animal is shown in FIG. 19. Each point is the average of 100 evoked responses. The threshold for eliciting a CAP was lower for anodal-first pulses in the threshold and mid-range response zones, demonstrating that anodal-first pulses can trigger CAP responses with less current than cathodal-first pulses

What is claimed is:

1. A method of monitoring activity of immune system cells of a subject, comprising:
   receiving ultrasonic waves from an external ultrasonic transducer;
   converting energy from the ultrasonic waves into electrical energy that powers a fully implanted medical device in the subject, the device comprising two or more electrodes that contact the splenic nerve of the subject;
   detecting an electrical activity of the splenic nerve;
   emitting an ultrasonic backscatter encoding information related to the electrical activity of the splenic nerve; and
   monitoring a deviation in the electric activity relative to a baseline electrical activity that indicates a change in the activity of the immune cells of the subject.

2. The method of claim 1, wherein the method comprises monitoring inflammation in the subject, wherein a change in the electrical activity of the splenic nerve indicates a change in inflammation in the subject.

3. The method of claim 1, wherein the method comprises monitoring a therapy administered to the subject.

4. The method of claim 3, further comprising administering the therapy to the subject.

5. The method of claim 3, wherein the therapy is an anti-inflammatory therapy.

6. The method of claim 5, wherein the anti-inflammatory therapy is administered in response to a detected increase in inflammation.

7. The method of claim 1, wherein the implantable medical device does not comprise a battery.

8. The method of claim 1, wherein the implantable medical device does not comprise a radiofrequency communication system.

9. The method of claim 1, wherein the implanted medical device has a length of about 5 mm or less in the longest dimension.

10. The method of claim 1, wherein the implanted medical device has a volume of about 5 $mm^3$ or smaller.

11. The method of claim 1, wherein the subject is anti-cyclic citrullinated peptide (anti-CCP) positive or fails to respond to a disease-modifying anti-rheumatic drug (DMARD).

12. The method of claim 1, wherein the implantable medical device does not comprise a battery.

13. A method of adjusting a therapy administered to a subject, comprising:
- receiving ultrasonic waves from an external ultrasonic transducer;
- converting energy from the ultrasonic waves into electrical energy that powers a fully implanted medical device in the subject, the device comprising two or more electrodes that contact the splenic nerve of the subject;
- detecting an electrical activity of the splenic nerve;
- emitting an ultrasonic backscatter encoding the electric activity of the splenic nerve;
- receiving the ultrasonic backscatter at an external device;
- monitoring a deviation in the electrical activity of the splenic nerve compared to a baseline electrical activity of the splenic nerve, wherein the deviation indicates a change in immune cell activity of the subject; and
- adjusting the therapy based on the change in immune cell activity of the subject.

14. The method of claim 13, wherein the change in immune cell activity is a change in an inflammatory response.

15. The method of claim 13, further comprising administering the therapy to the subject.

16. The method of claim 13, wherein the therapy is an anti-inflammatory therapy.

17. The method of claim 16, wherein the anti-inflammatory therapy is adjusted if the anti-inflammatory therapy does not result in a desired effect or results in an undesired inflammatory response.

18. The method of claim 16, wherein the anti-inflammatory therapy is discontinued if the anti-inflammatory therapy obtains a desired effect.

19. The method of claim 7, wherein the implantable medical device does not comprise a battery.

20. The method of claim 7, wherein the implantable medical device does not comprise a radiofrequency communication system.

21. The method of claim 7, wherein the implanted medical device has a length of about 5 mm or less in the longest dimension.

22. The method of claim 7, wherein the implanted medical device has a volume of about 5 mm$^3$ or smaller.

23. The method of claim 7, wherein the subject is anti-cyclic citrullinated peptide (anti-CCP) positive or fails to respond to a disease-modifying anti-rheumatic drug (DMARD).

* * * * *